US008790898B2

(12) United States Patent
Hovanessian et al.

(10) Patent No.: US 8,790,898 B2
(45) Date of Patent: Jul. 29, 2014

(54) SYNTHETIC PEPTIDES CORRESPONDING TO OVERLAPPING NEUTRALIZING DETERMINANTS IN THE CBD1 EPITOPE INDUCE BROADLY NEUTRALIZING ANTIBODIES

(75) Inventors: Ara Hovanessian, El Metn (LB); Bernard Krust, Paris (FR)

(73) Assignee: Centre National de la Recherche Scientifique (CNRS), Paris Cedex 16 (FR)

( * ) Notice: Subject to any disclaimer, the term of this patent is extended or adjusted under 35 U.S.C. 154(b) by 422 days.

(21) Appl. No.: 13/061,035

(22) PCT Filed: Aug. 27, 2009

(86) PCT No.: PCT/EP2009/061083
§ 371 (c)(1),
(2), (4) Date: Feb. 25, 2011

(87) PCT Pub. No.: WO2010/023247
PCT Pub. Date: Mar. 4, 2010

(65) Prior Publication Data
US 2011/0217307 A1    Sep. 8, 2011

(30) Foreign Application Priority Data

Aug. 29, 2008 (EP) .................... 08290813

(51) Int. Cl.
*C12N 15/00* (2006.01)
*C07K 5/00* (2006.01)
*C12Q 1/70* (2006.01)

(52) U.S. Cl.
USPC ................. 435/69.7; 530/300; 424/208.1

(58) Field of Classification Search
None
See application file for complete search history.

(56) References Cited

U.S. PATENT DOCUMENTS

| 5,639,854 | A | 6/1997 | Sia et al. | |
|---|---|---|---|---|
| 7,153,509 | B2 * | 12/2006 | Haynes et al. | 424/192.1 |
| 7,364,744 | B2 * | 4/2008 | Hovanessian et al. | 424/208.1 |
| 8,173,767 | B2 * | 5/2012 | Hovanessian et al. | 530/300 |

FOREIGN PATENT DOCUMENTS

JP    2004535799 A    12/2004

OTHER PUBLICATIONS

Benferhat, R. et al., "The immunogenic CBD1 peptide corresponding to the caveolin-1 binding doman in HIV-1 envelope gp41 has the capacity to penetrate the cell membrane and bind caveolin-1," Molecular Immunology 45 (2008), pp. 1963-1975.
Hovanessian, A. et al., "The Caveolin-1 Binding Domain of HIV-1 Glycoprotein gp41 is an Efficient B Cell Epitope Vaccine Candidate Against Virus Infection," Immunity 21, Nov. 2004, pp. 617-627.
Bazhan, S., et al., "A synergistic effect of a combined bivalent DNA-protein anti-HIV-1 vaccine containing multiple T- and B-cell epitopes of HIV-1 proteins," Molecular Immunology 45, (2008), pp. 661-669.
Chianese-Bullock, K.A., et al., "A Multipeptide Vaccine is Safe and Elicits T-cell Responses in Participants With Advanced Stage Ovarian Cancer," Immunother 31:4, May 2008, pp. 420-430.
Search Report, European Application No. EP 08 29, 0813, Apr. 24, 2009.
International Search Report and Written Opinion, PCT Application No. EP2009/061083, Nov. 5, 2009.
Stephen J.D. Bell et al., "Definition of an Immunodominant T Cell Epitope Contained in the Envelope gp41 Sequence of HIV-1", Clinical and Experimental Immunology (1992), vol. 87, pp. 37-45.
Japanese Office Action (with English Translation) dated Feb. 6, 2014, issued in Japanese Application No. 2011-524382.
Slingluff et al., "Phase I Trial of a Melanoma Vaccine with gp 100 280-288 Peptide and Tetanus Helper Peptide in Adjuvant: Immunologic and Clinical Outcomes1", Clinical Cancer Research, vol. 7, pp. 3012-3024. (2001).
Rey-Cuiflé et al, "HIV-1 Neuralizing Antibodies Elicited by The Candidate CBD1 Epitoipe Vaccine React With The Conserved Caveolin-1 Binding Motif of Viral Glycoprotein gp41", Journal of Pharmacey and Pharmacology, vol. 58, pp. 759-767. (2006).

* cited by examiner

*Primary Examiner* — Agnieszka Boesen
(74) *Attorney, Agent, or Firm* — Venable LLP; Nancy J. Axelrod; Michael A. Gollin

(57) ABSTRACT

The present invention relates to chimeric peptides having a caveolin-1 binding domain of an HIV-1 gp41 (CBD1) peptide or a variant of said CBD1, fused to a T helper epitope. In one aspect, the T epitope is from a peptide selected from the group consisting of a tetanus toxin, an HIV-1 Gag p24 and an HIV-1 Env-gp120. Compositions containing these chimeric peptides and pharmaceutical and immunogenic compositions as well as vaccines comprising these chimeric peptides also are part of the present invention. Methods to induce neutralizing antibodies against HIV-1 activity and uses of the chimeric peptides to treat or to prevent HIV-1 infection are also disclosed.

12 Claims, 20 Drawing Sheets

T helper epitope

C18K: C-K-S-L-E-Q-I-W-N-N-M-T-W-M-Q-W-D-K ___ Immunogenic

C17K:     C-S-L-E-Q-I-W-N-N-M-T-W-M-Q-W-D-K ___ Immunogenic

C13K:                   C-I-W-N-N-M-T-W-M-Q-W-D-K ___ Not-immunogenic

B cell epitope

SYNTHETIC PEPTIDES CORRESPONDING TO OVERLAPPING NEUTRALIZING DETERMINANTS IN THE CBD1 EPITOPE INDUCE BROADLY NEUTRALIZING ANTIBODIES

FIELD OF THE INVENTION

The present invention relates to chimeric peptides having a caveolin-1 binding domain of an HIV-1 gp41 peptide fused to a T helper epitope of a peptide selected from the group consisting of a tetanus toxin, an HIV-1 Gag p24 and an HIV-1 Env-gp120. Compositions containing these chimeric peptides or proteins and pharmaceutical, immunogenic compositions and vaccines comprising these chimeric peptides or proteins also are part of the present invention. Methods of neutralizing HIV-1 activity and uses of the chimeric peptides to induce neutralizing antibodies against HIV-1 activity as well as methods of treating HIV-1 infection are also disclosed.

BACKGROUND OF THE INVENTION AND RELATED PRIOR ART

Ever since the discovery and isolation of LAV by Barre-Sinousi, Chermann and Montagnier in 1983 at the Pasteur Institute a search for effective treatment without major side effects and prevention of AIDS has been elusive.

Treating patients with AIDS with a combination of reverse transcriptase and drugs that target HIV's protease enzyme, known in the art as "highly active antiretroviral therapy," is effective to drive the viral load in blood to low levels.

Thus, since 1996, antiretroviral drugs such as zidovudine (AZT), ritonavir, saquinavir, lamivudine, amprenavir, abacavir, idinavir, nelfinavir and the like, were generally used in triple-drug therapy using two reverse transcriptase inhibitors and one protease inhibitor, to reduce the amount of HIV in patients. However, none of these drugs entirely eliminates the virus.

Moreover, there remains serious problems associate with the triple-drug therapy. Not only must an HIV-infected person take the drugs on a consistent schedule and for the duration of life, but these drugs are not only quite expensive ($10,000 annually or more), but toxic. Due to their toxic nature, anti-retroviral drugs have known side effects which include nausea, vomiting, diarrhea, anemia, lipodystrophy, diabetes-like problems, brittle bones, numbness, tingling or pain in the hands or feet, and heart disease. As a result of these side effects many AIDS patients stop taking their medication.

Besides their toxic effects, one of the major difficulties with highly active retroviral therapy is drug resistance. Since HIV is known to constantly mutate, billions of new HIV viruses are produced in the body every day. These mutations change parts of the virus often rendering the drugs ineffective. The alternative to antiretroviral drugs would be to develop an effective vaccine against HIV.

It is now widely believed that a successful HIV vaccine preparation should have components to stimulate T-cell responses and to elicit anti-HIV antibodies. Currently more than 25 HIV vaccines designed to stimulate T-cell responses are in clinical trials, whereas no vaccine that is capable of stimulating the production of broadly neutralizing antibodies and/or antibodies that inhibit infection by primary isolates of HIV-1 has yet been described. Thus the design of a vaccine capable of stimulating neutralizing antibodies that inhibit primary HIV isolates appears to be one of the highest priorities in the HIV vaccine research (McMichael, 2006; Zwick and Burton, 2007).

The external envelope glycoprotein gp120 has widely been investigated for the development of neutralizing antibodies. However such antibodies are isolate specific due to the sequence variability of gp120 and thus have a limited action; in particular they fail to neutralize primary isolates. Alternative strategies are now being evaluated for the stimulation of neutralizing antibodies against the receptor, coreceptor binding sites and also cryptic epitopes that may become exposed following the binding of gp120 to CD4 (Lin and Nara, 2007; McMichael and Hanke, 2003). In contrast to gp120, the transmembrane envelope glycoprotein gp41 provides a good alternative glycoprotein to explore by virtue of the conserved domains. However, the problem in this case is that the strategic epitopes might be covered by gp120 and/or are thought to be cryptic epitopes (Wyatt and Sodroski, 1998). An exception is the C-terminal half of the gp41 ectodomain harboring the epitopes of neutralizing human antibodies 2F5 and 4E10. Subunits of gp41 have been considered as candidates for a vaccine; however, antibodies raised against the N-HR and C-HR regions were shown to be non-neutralizing under physiological conditions. Similarly, all attempts to induce neutralizing antibodies against the epitope of neutralizing human monoclonal antibodies 2F5 and 4E10 have failed (Lin and Nara, 2007; Zwick and Burton, 2007).

A strategic epitope in the HIV-1 transmembrane envelope glycoprotein gp41 that is conserved in every single HIV-isolate has been identified (Hovanessian et al., 2003, 2004a; Hovanessian et al., 2004b). Synthetic peptides corresponding to this epitope (named the CBD1 epitope) were then shown to elicit reproducibly in rabbits the production of antibodies that inhibit HIV-1 infection of primary CD4$^+$ T lymphocytes by various T lymphocyte and macrophage-tropic HIV-1 isolates and as well as primary isolates of clades A to G. Viral particles preincubated with the immune sera loose their infectivity, while addition of the immune sera to virus producing cultures results in the production of defective virus particles (Hovanessian et al., 2004b). The caveolin-binding domain therefore is exposed on HIV particles and also on virus-infected cells. The anti-CBD1 antibodies act on two distinct steps on the HIV-infectious cycle: 1) they prevent infection of cells by HIV particles; and 2) they cause aggregation of gp41 at the plasma membrane in HIV-producing cells leading to the production of virus particles deficient in the gp120-gp41 complex.

A highly conserved B cell-epitope, the CBD1 epitope, in the ectodomain of HIV-1 gp41, and the capacity of peptides corresponding to this epitope to elicit the production of antibodies that inhibit various HIV-1 isolates, provided promising perspectives for the development of synthetic universal B-cell epitope vaccine candidate for HIV/AIDS (Hovanessian et al., 2003, 2004a; Hovanessian et at., 2004b).

However, improved HIV-1 vaccines that provide better immunogenic protection is still needed.

Thus it is an object of the present invention to provide a composition and more specifically an immunogenic composition that induces broadly neutralizing activities and/or antibodies that inhibit infection by primary isolates of HIV-1.

It is another object of the present invention to provide a universal B-cell epitope vaccine capable of eliciting in a mammal the induction of HIV-specific broadly reactive neutralizing antibodies.

It is yet another object of the present invention to provide vaccines which contain highly purified peptides that can be made in larger quantities and at lower costs.

Yet another object of the present invention provides immunogenic compositions with fewer side effects that broadly elicit neutralizing antibodies because of their conserved nature among various HIV-1 isolates and clades.

Still yet another object of the present invention is to provide immunogenic compositions or vaccine preparations that have application as a therapeutic vaccine in HIV-infected individuals, since HIV-infected individuals appear to lack the capacity to produce naturally anti-CBD1 antibodies.

Another object of the present invention is to provide a chimeric peptide or chimeric proteins that can be used in compositions, pharmaceutical compositions, immunogenic compositions and as vaccines.

Antibodies and especially monoclonal antibodies directed to the described peptides and chimeric peptides is another object of the invention.

Still another object of the present invention is to provide a method of neutralizing HIV-1, said method comprising administering to a mammal in need of such treatment at least one chimeric peptide of the present invention. Also disclosed is at least one chimeric peptide of the invention for use in neutralizing HIV-1.

Yet another object of the present invention is a method to induce antibodies able to neutralize HIV-1, said method comprising administering to a mammal in need of such treatment at least one peptide of the present invention with at least one peptide containing a T helper epitope.

Use of at least one chimeric peptide described in the present invention for the manufacture of a medicament to induce neutralizing antibodies against HIV-1 is yet another object of the invention.

Yet another object of the present invention is the use of at least one chimeric peptide for prophylaxis for HIV-1 infection.

These and other aspects and objects are achieved by the present invention as evidenced by the summary of the invention, description of the preferred embodiments and the claims.

SUMMARY OF THE PRESENT INVENTION

The present invention thus relates to a chimeric peptide comprising a caveolin-1 binding domain (CBD1) of an HIV-1 gp41 peptide or a variant of CBD1, fused to a T helper epitope peptide. In another aspect, the invention relates to a chimeric peptide comprising a caveolin-1 binding domain of an HIV-1 gp41 peptide or a variant of CBD1 fused to a T helper epitope peptide selected from the group consisting of a tetanus toxin, an HIV-1 Gag-p24 and an HIV-1 Env-gp 120.

In another aspect of the invention, the caveolin-1 binding domain of an HIV-1 gp41 peptide in the chimeric peptide consists of or consists essentially of SLEQIWNNMTWMQWDK (SEQ ID No: 1).

In yet another aspect, the T helper epitope peptides in the chimeric protein are a tetanus toxin $Tet_{830}$ peptide consisting of or consisting essentially of the sequence AQYIKANSKFIGITEL (SEQ ID No: 2), an HIV-1 $gp120_{421-436}$ peptide consisting of or consisting essentially of the sequence KQIINMWQVVGKAMYA (SEQ ID No: 3) or an HIV-1 $Gag_{298-312}$ peptide consisting of or consisting essentially of the sequence KRWIILGLNKIVRMY (SEQ ID No: 4).

The chimeric peptide of the present invention has a dilysine linker (KK) or a glycine proline linker having the sequence of amino acid residues 16 to 20 of SEQ ID NO: 16 (GPGPG), which links the caveolin-1 binding domain gp41 peptide to the T helper epitope.

In still another aspect, the present invention provides chimeric peptides selected from the group of: A-Q-Y-I-K-A-N-S-K-F-I-G-I-T-E-L-K-K-C-K-S-L-E-Q-I-W-N-N-M-T-W-M-Q-W-D-K (SEQ ID No: 5), A-Q-Y-I-K-A-N-S-K-F-I-G-I-T-E-L-K-K-C-S-L-E-Q-I-W-N-N-M-T-W-M-Q-W-D-K (SEQ ID No:6), K-Q-I-I-N-M-W-Q-V-V-G-K-A-M-Y-A-K-K-C-K-S-L-E-Q-I-W-N-N-M-T-W-M-Q-W-D-K (SEQ ID No: 7), K-R-W-I-I-L-G-L-N-K-I-V-R-M-Y-K-K-C-K-S-L-E-Q-I-W-N-N-M-T-W-M-Q-W-D-K (SEQ ID No: 8), A-Q-Y-I-K-A-N-S-K-F-I-G-I-T-E-L-K-K-I-W-N-N-M-T-W-M-Q-W-D-K (SEQ ID No: 9), K-R-W-I-I-L-G-L-N-K-I-V-R-M-Y-K-K-I-W-N-N-M-T-W-M-Q-W-D-K (SEQ ID No: 10), K-Q-M-N-M-W-Q-V-V-G-K-A-M-Y-A-K-K-I-W-N-N-M-T-W-M-Q-W-D-K (SEQ ID No: 11), K-R-W-I-I-L-G-L-N-K-I-V-R-M-Y-K-K-I-W-N-N-M-T-W-M-Q-W (SEQ ID No: 12), K-R-W-M-L-G-L-N-K-I-V-R-M-Y-K-K-I-W-N-N-M-T-W (SEQ ID No: 13), K-R-W-I-I-L-G-L-N-K-I-V-R-M-Y-K-K-C-S-L-E-Q-I-W-N-N-M (SEQ ID No: 14), K-R-W-I-I-L-G-L-N-K-I-V-R-M-Y-K-K-C-I-W-N-N-M (SEQ ID No: 15), K-R-W-I-I-L-G-L-N-K-I-V-R-M-Y-G-P-G-P-G-I-W-N-N-M-T-W-M-Q-W (SEQ ID No: 16), K-R-V-V-I-I-L-G-L-N-K-I-V-R-M-Y-G-P-G-P-G-I-W-N-N-M-T-W (SEQ ID No: 17), K-R-W-I-I-L-G-L-N-K-I-V-R-M-Y-K-K-I-W-D-N-M-T-W-M-E-W-E-R (SEQ ID No: 18), K-R-W-I-I-L-G-L-N-K-I-V-R-M-Y-K-K-I-W-D-N-M-T-W-M-E-W (SEQ ID No: 19), R-G-D-A-Q-Y-I-K-A-N-S-K-F-I-G-I-T-E-L-K-K-I-W-N-N-M-T-W-M-Q-W-D-K (SEQ ID No: 20), R-G-D-K-R-W-I-I-L-G-L-N-K-I-V-R-M-Y-K-K-I-W-N-N-M-T-W-M-Q-W-D-K (SEQ ID No: 21), R-G-D-K-R-W-I-I-L-G-L-N-K-I-V-R-M-Y-K-K-I-W-N-N-M-T-W-M-Q-W (SEQ ID No: 22), C-I-W-N-N-M-T-W-M-Q-W-D-K (SEQ ID No: 33), K-R-W-I-I-L-G-L-N-K-I-V-R-M-Y-K-K-I-W-N-N-M-T-W-M-Q-W-D-K (SEQ ID No: 34), K-R-W-I-I-L-G-L-N-K-I-V-R-M-Y-K-K-I-W-N-N-M-T-W (SEQ ID No: 35), K-R-W-I-I-L-G-L-N-K-I-V-R-M-Y-K-K-I-W-N-N-M (SEQ ID No: 36), K-R-W-I-I-L-G-L-N-K-I-V-R-M-Y-G-P-G-P-G-I-W-N-N-M-T-W-M-Q-W (SEQ ID No: 37), K-R-W-I-I-L-G-L-N-K-I-V-R-M-Y-G-P-G-P-G-I-W-N-N-M-T-W (SEQ ID No: 38), and mixtures thereof, as well as A-Q-Y-I-K-A-N-S-K-F-I-G-I-T-E-L-K-K-I-W-N-N-M-T-W-M-Q-W (SEQ ID NO:52), A-Q-Y-I-K-A-N-S-K-F-I-G-I-T-E-L-K-K-I-W-N-N-M-T-W (SEQ ID NO:53), A-Q-Y-I-K-A-N-S-K-F-I-G-I-T-E-L-G-P-G-P-G-I-W-N-N-M-T-W-M-Q-W (SEQ ID NO:54), A-Q-Y-I-K-A-N-S-K-F-I-G-I-T-E-L-G-P-G-P-G-I-W-N-N-M-T-W (SEQ ID NO:55), K-Q-I-I-N-M-W-Q-V-V-G-K-A-M-Y-A-K-K-I-W-N-N-M-T-W-M-Q-W (SEQ ID NO:56), K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58) and K-Q-I-I-N-M-W-Q-V-V-G-K-A-M-Y-A-G-P-G-P-G-I-W-N-N-M-T-W (SEQ ID NO:59), and mixtures thereof, and the mixtures of any of the above-mentioned peptides. The invention also concerns the following peptides: C-S-L-E-Q-I-W-N-N-M-T-W-M-Q-W-D-K (SEQ ID No: 31), C-S-L-E-Q-I-W-N-N-M (SEQ ID No: 32) and C-S-L-E-Q-I-A-N-N-M-T-A-M-Q-A-D-K (SEQ ID No: 39).

Antibodies, in particular monoclonal antibodies, directed against at least one of the chimeric peptides of SEQ ID Nos. 5 to 25, of SEQ ID Nos. 31 to 38 and 52 to 59 and of SEQ ID No. 39 and the peptides of SEQ ID Nos. 22 to 24 or the peptides of at least one of SEQ ID Nos. 1, 26 to 30 fused to at least one of SEQ ID Nos. 2 to 4 and mixtures thereof also form another aspect of the invention.

A composition comprising at least one chimeric peptide, preferably one chimeric peptide or the chimeric peptides described herein, or antibodies or monoclonal antibodies described herein and a physiologically acceptable diluent also is yet another aspect of the invention.

In yet another aspect an immunogenic composition or a pharmaceutical composition comprising at least one chimeric peptide, preferably one chimeric peptide or the described herein chimeric peptides or the described herein antibodies, particularly monoclonal antibodies, and a pharmaceutically acceptable carrier is provided.

A vaccine comprising at least one chimeric peptide, preferably one chimeric peptide or the chimeric peptides as described herein or the antibodies, particularly monoclonal antibodies, as described herein and a pharmaceutically acceptable carrier forms yet another aspect of the present invention.

A method for treating HIV-1 infection or neutralizing HIV-1 activity, comprising administering to a mammal in need of such treatment at least one chimeric peptide, preferably one chimeric peptide or the chimeric peptides as described herein and mixtures thereof, then further administering a T helper epitope or vice versa is yet another aspect of the present invention.

The chimeric peptide or chimeric peptides as described herein or the antibodies, particularly monoclonal antibodies, described herein for the use as a medicament or for use in the neutralization of HIV-1 or for the use in the treatment of AIDS and symptoms of HIV-1 infection, is another aspect of the present invention.

Use of at least one chimeric peptide or preferably one chimeric peptide, or the chimeric peptides as described herein or the antibodies, particularly monoclonal antibodies, as described herein for the manufacture of a medicament to neutralize or to treat HIV-1 or as a prophylaxis for HIV-1 infection is yet another aspect of the present invention.

BRIEF DESCRIPTION OF THE DRAWINGS

FIG. 3 are sequences of three CBD1 or CBD1-based peptides illustrating that part of the sequence, which contains T helper and B cell epitopes, which are immunogenic compared to the non-immunogenic counterpart.

FIGS. 10 A and 10 B are graphs showing anti-CBD1 antibody titer in serum of macaques immunized with the CBD1 (C18K) peptide. Macaques were immunized at week 0, 4, 8, 12, and 16 with the CBD1 peptide (200 μg) via the intradermal (i.d.) or intramuscular (i.m.) route with adjuvant [MF59+MDP-Lys(L18)]. Vertical arrows indicate the days of vaccination. Immune sera from bleedings recovered at a two week interval for a period of 24 weeks were assayed by ELISA against the CBD1 (C18K) peptide. The titers correspond to the dilution of anti-CBD1 peptide antibodies giving OD value ≥0.1. No reactivity with the CBD1 (C18K) peptide was observed with the sera from the control macaques injected with the adjuvant alone (not shown). * Macaque M13284 and M11321 generated a T cell response against the CBD1 peptide (presented in FIG. 9).

FIGS. 11A and 11 B are graphs showing anti-CBD1 antibody titer in the serum of macaques immunized with the CBD1 (C18K) peptide. This set of immunizations started four months after the fifth injection of macaques of the first study. Both groups of macaques were immunized subcutaneously with the free CBD1 (C18K) and Tet peptide (200 μg+150 μg) or Tet-KK-CBD1 (350 μg) using as adjuvant the mixture [CpG+Montanide ISA 51]. Macaques were immunized at day 0, 28, and 57 (indicated by the arrows). Sera at day 0, 15, 28, 43, 57, 71, 86 and 98, were titrated by ELISA against the CBD1 (C18K) and the Tet peptide. The titers correspond to the dilution of anti-CBD1 peptide antibodies giving OD value ≥0.1 in ELISA.

FIGS. 15A and 15 B are graphs showing the kinetics of anti-CBD1 and anti-C13K peptide antibodies in macaques immunized with the CBD1 peptide, free or fused with the Tet peptide. Immune sera at different days from macaque M11635 and M13284 immunized with the free [CBD1+Tet] and TT-KK-CBD1 peptide, respectively, were tested by ELISA against the CBD1 and the C13K peptide. The ordinates give the titers of anti-CBD1 (dark histograms) and anti-C13K (light histograms) antibodies corresponding to the dilution of immune sera giving OD value ≥0.1.

PREFERRED EMBODIMENTS OF THE INVENTION

Figure 1:
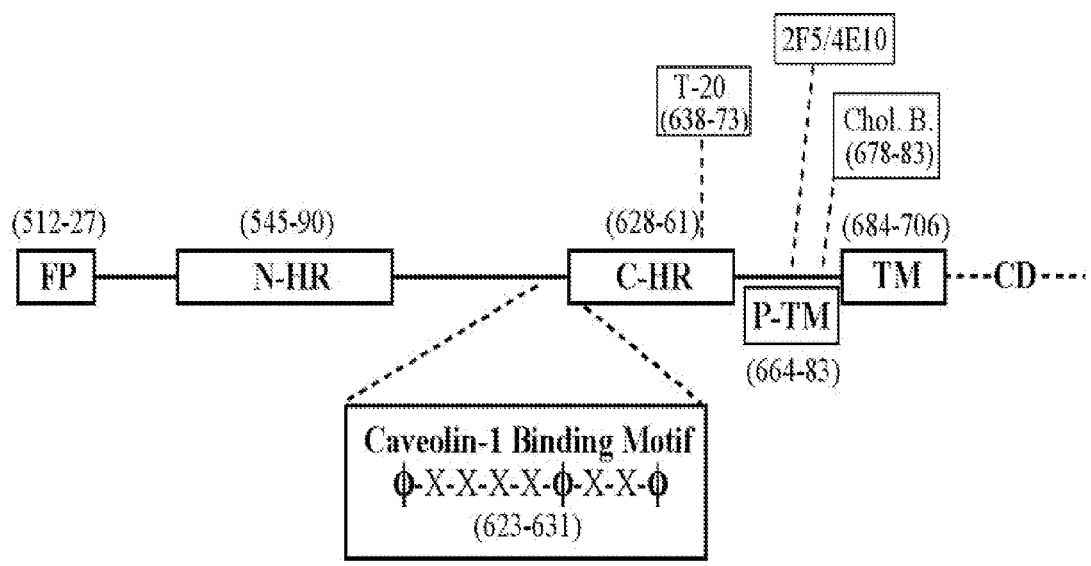
FIG. 1 is a schematic drawing of HIV-1 gp41 showing the location of the conserved caveolin-binding motif (WXXXX-WXXW; SEQ ID No: 41). The important functional domains of gp41 ectodomain are: the fusion peptide (FP) that becomes inserted into the membrane of HIV-target cells; the transmembrane region (TM) responsible for anchorage in the plasma membrane, the two hydrophobic heptad repeat domains characteristic of coiled-coils (N-HR and C-HR), the conserved tryptophan-rich domain adjacent to TM (P-TM) that appears to cooperate with FP. The last five amino acids of P-TM (LWYIK) bind cholesterol. The P-TM also contains the core representative ELDKWA and NWFDIT epitope of the two broadly neutralizing human monoclonal antibodies (2F5 and mAb 4E10, respectively). The synthetic peptide T-20 is used in clinic as an inhibitor of gp41-mediated fusion process. CD stands for the cytoplasmic domain. For references see (Rey-Cuillé et al., 2006).

As used herein, a "chimeric peptide" or a "fusion protein" are used interchangeably and means that this peptide or protein is created by joining two or more peptides sequences, which are naturally not joined together. The chimeric peptide has a size of no more than 50 amino acids, or no more than 40 amino acids, or no more than 30 amino acids, or no more than 25 amino acids or no more than 20 amino acids. Generally, the chimeric peptide has between 50 to 50 amino acid residues or 5 to 40 amino acid residues or 5 to 30 amino acid residues or 5 to 20 amino acid residues or 10 to 50 amino acid residues or 10 to 40 amino acid residues or 10 to 30 amino acid residues or 10 to 20 amino acid residues.

In an embodiment, the chimeric peptide of the invention is chemically synthesized. Therefore, the chimeric peptide of the invention does not bear posttranslational modifications, in particular its amino acid residues are not modified by glycosylation. In another aspect, the NTX motif (residues 625 to 627 of the peptide of FIG. 2) is not glycosylated.

Several chimeric peptides are those described herein. "Several" means 1 to 20, 1 to 10, 1 to 8 or 1 to 5 chimeric peptides.

As used herein the term "fused" means joined such that the two peptides are joined to form a single peptide. The peptides can be joined or fused either chemically through various bonds or genetically by peptide bonds.

The term "prophylaxis" as used herein means prevention of or protective treatment for HIV-1 or against HIV infection.

As used herein the term "treat" means to diminish the HIV-1 virus. In this regard, the amount of HIV-1 virus is decreased more than 50% as compared to the absence of treatment. In another aspect, the amount of HIV-1 virus is decreased more than 75% as compared to the absence of treatment. In yet another aspect, the amount of HIV-1 virus is decreased 100% as compared to the absence of treatment.

The term "neutralizing antibody" as used herein means an antibody, either monoclonal or polyclonal, that influences the HIV-1 particle in such a way that the replicative cycle of the virus becomes inhibited at an early phase of the virus infection or that the virus release is blocked, or that causes the production of defective virus particles that are not infectious.

The term "epitope and "determinant" will be used interchangeably, to define the portion of an antigenic molecule (e.g., a peptide), that is specifically bound by the antibody combining site of an antibody. The term epitope encompasses both a linear epitope for which the consecutive amino acids are recognized by the antibody as well as a conformational epitope for which the antibodies recognize amino acids to the extent they adopt a proper configuration or conformation. Consequently, in some epitopes, the conformation (three dimensional structure) is as important as the amino acid sequence (primary structure).

As used herein the term "specifically" when referring to antibody recognition of an antigen means that no cross-reaction occurs, with unrelated peptides i.e., peptides not related to or derived from the CBD1 domain.

As used herein "mammal" means any of various warm-blooded vertebrate animals of the class Mammalia, including humans, characterized by a covering of hair on the skin and, in the female, milk-producing mammary glands for nourishing the young.

The term "passive vaccine" means a vaccine conferring temporary protection against HIV infection upon administration to an individual.

Figure 2:
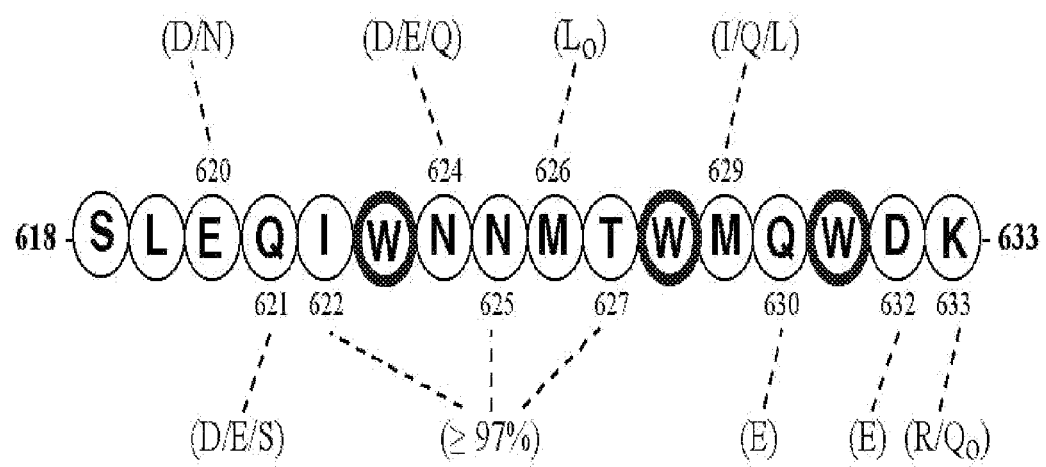
FIG. 2 is the conserved sequence of CBD1 domain in the ectodomain of gp41, from various HIV-1 isolates. The sequence of the CBD1 peptide corresponds to amino acids: Ser-Leu-Glu-Gln-Ile-Trp-Asn-Asn-Met-Thr-Trp-Met-Gln-Trp-Asp-Lys. CBD1 is located at amino acid residues 618-633 in the consensus sequence in the gp41 ectodomain. The three-tryptophan residues (W in bold) in the caveolin-binding motif are conserved among more than 850 isolates of HIV-1. The percent conservation is given in brackets for some amino acid residues while for others the most frequent amino acid is given in brackets. The $^{625}NMT^{627}$ sequence is highly conserved most probably due to the presence of a N-linked glycosylation site (N-X-T), which is one of the N-linked glycosylation sites in the gp41 ectodomain. The other residues in the CBD1 peptide, $S^{618}/M^{629}/Q^{630}/D^{632}$ are 90-97% conserved, whereas $E^{620}/Q^{621}/N^{624}/K^{633}$ are slightly variable but their variation is mostly semi-conservative. The relatively conserved $M^{626}$ residue is L in HIV-1 type O.

As used herein "caveolin-1 binding domain of an HIV-1 gp41 peptide" or "CBD1" means a peptide, consisting from amino acid residues 618 to 633 of the consensus sequence in the gp41 ectodomain, as defined in SEQ ID No: 1 (Ser-Leu-Glu-Gln-Ilo-Trp-Asn-Asn-Met-Thr-Trp-Met-Gln-Trp-Asp-Lys) and presented in FIG. 2. A peptide comprising or consisting essentially of a CBD1 domain or of a CBD1 variant excludes the full length gp41 peptide, as well as the full length HIV-1 envelope (gp160).

As used herein "a peptide variant" means a peptide that has been modified by addition of amino acid residues at one or both ends, and/or that has been modified by substitution of amino acids residues, in particular semi-conservative substitution. Therefore, a variant is a peptide whose the specific consecutive sequence [defined in the sequence identification number (SEQ ID No.)] can include 1 to 6 additional amino acids (1, 2, 3, 4, 5 or 6 residues) at either end or at both ends of the specific sequence identified by its SEQ ID No. provided that these additional amino acids do not affect the capacity to induce neutralizing antibodies against HIV-1 activity. Such addition of residues is encompassed by the term "consisting essentially of" with respect to the sequence of a peptide. A peptide variant, alternatively to or in combination with the previous definition, also means a peptide whose 1 to 6 amino acids (1, 2, 3, 4, 5 or 6) have been replaced by other semi-conservative amino acid residues, provided that these amino acid substitutions do not affect the capacity to induce neutralizing antibodies against HIV-1 activity. For example, nonpolar hydrophobic) amino acid residues include alanine (Ala or A), leucine (Leu or L), isoleucine (Ile or I), valine (Val or V), proline (Pro or P), phenylalanine (Phe or F), tryptophan (Trp or W) and methionine (Met or M); polar neutral amino acid residues include glycine (Gly or G), serine (Ser or S), threonine (Thr or T), cysteine (Cys or C), tyrosine (Tyr or Y), asparagine (Asn or N) and glutamine (Gln or Q); positively charged (i.e., basic) amino acid residues include arginine (Arg or R), lysine (Lys or K) and histidine (His or H); and negatively charged (i.e., acidic) amino acid residues include aspartic acid (Asp or D) and glutamic acid (Glu or E).

As used herein, the terms "a CBD1 variant", "a peptide derived from CBD1" and "a CBD1-based peptide" are used interchangeably, and mean a variant of CBD1, as defined in the previous paragraph. An example of such CBD1 variant includes a peptide whose sequence consists of $X_n$SLEQIWN-NMTWMQWDKX$_m$ (SEQ ID No. 25), where X is any amino acid and n and m are independently integers of 0 to 6, provided that n does not exceed 6 additional amino acids. Another example of CBD1 variant includes a peptide whose sequence corresponds to SEQ ID No: 1 in which 1 to 6 amino acid residues (1, 2, 3, 4, 5 or 6) among the positions of the following Table have been substituted. It is excluded that the tryptophan residues in positions 623, 628 and 631 be substituted (FIG. 2).

|  | Position | | | | | | | |
| --- | --- | --- | --- | --- | --- | --- | --- | --- |
|  | 620 | 621 | 624 | 626 | 629 | 630 | 632 | 633 |
| Residue found in CBD1 (FIG. 2) | E | Q | N | M | M | Q | D | K |
| Semi-conservative residue(s) | D/N | D/E/S | D/E/Q | L | I/Q/L | E | E | R/Q |

More specifically, the present invention relates to chimeric peptides comprising or consisting essentially of or consisting of a caveolin-1 binding domain of an HIV-1 gp41 peptide fused to a T helper epitope.

The caveolin-1 binding domain of an HIV-1 gp41 (CBD1) peptide is well known in this art and is described in EP 1 466 924. The synthetic peptide of this binding domain has the amino acid sequence of SLEQIWNNMTWMQWDK (SEQ ID No: 1), corresponding to the region in gp41 of HIV-1 from amino acid positions 618 to 633 (Hovanessian et al 2004). The distinct binding motif of WNNMTWMQW (SEQ ID No. 26) is conserved in every single virus isolate (Hovanessian et al, supra).

Thus the chimeric peptides of the present invention contain the CBD1 peptide and also CBD1 variants. These peptide variants retain all or part of the distinct binding motif of WNNMTWMQW (SEQ ID No. 26), in which one to three of the tryptophan residues is retained. Thus one of the variants of the present invention has the amino acid sequence $X_n$WNNM (SEQ ID NO: 27) where X is any amino acid and n is a number from 1 to 6 (1, 2, 3, 4, 5 or 6). In another embodiment, the variant of the invention has the sequence: $X_n$WNNMTW (SEQ ID No: 28) where X is any amino acid and n is a number from 1 to 3. In yet another aspect, the variant of the invention has the sequence: $X_n$WNNMTWMQWZ$_p$ (SEQ ID No: 29) where X and Z are any amino acid, n is a number from 1 to 6 and p is a number from 0 to 3, preferably 1 to 3.

In another embodiment, the present invention relates to a chimeric protein in which the CBD1 peptide variant has the amino acid $X_n$WNNMTWMQWZ (SEQ ID No: 30) where X is any amino acid, n is a number from 1 to 6 and Z is D-K (i.e, Asp-Lys).

The chimeric protein of the present invention has the CBD1 peptide or CBD1 variant, as described above, fused to a T helper epitope peptide. This fusion can be via chemical fusion in which the chimeric peptide is synthesized using standard methods known in the art such as by using Fmoc chemistry or it can be genetically fused whereas the peptide is recombinantly produced and the fusion is by peptidic bonds.

Any T helper epitope peptide can be used in the chimeric protein, as long as the T helper ensures the induction of antibodies able to recognize the CBD1 domain and able to neutralize HIV-1 activity. Such T helper epitopes could be from any protein of human, animal, plant, bacterial or viral origin. In a particular embodiment, T helper epitopes are non-natural (i.e. synthetic). As examples of T helper epitopes that can be used in the present invention are:

the OVAp$_{323-336}$ (ISQAVHAAHAEINE), a strong T helper epitope from ovalbumin, the PADRE peptide aKXVAAWTLKAAaZC (X=L-cyclohexylalanine, Z=aminocaproic acid), a nonnatural pan HLA DR-binding Epitope; or epitopes from HIV-1 proteins including the Gag, gp120, gp41 and polymerase proteins.

In a particular embodiment, the chimeric peptide of the invention comprises or consists essentially of or consists of a caveolin-1 binding domain of an HIV-1 gp41 peptide fused to a T helper epitope of a peptide selected from the group consisting of a tetanus toxin, an HIV-1 Gag-p24 and an HIV-1 Env-gp120.

In one embodiment the T helper epitope peptides that form part of the chimeric protein of the present invention are selected from a tetanus toxin peptide, an HIV-1 Gag p24 peptide or an HIV-1 Env-gp120 peptide. In one embodiment, the T helper epitope proteins are a tetanus toxin Tet$_{830}$ peptide comprising or consisting of or consisting essentially of the sequence AQYIKANSKFIGITEL (SEQ ID No: 2), an HIV-1 gp120$_{421-436}$ peptide comprising or consisting of or consisting essentially of the sequence KQIINMWQVVGKAMYA (SEQ ID No: 3) or an HIV-1 Gag$_{298-312}$ peptide comprising or consisting of or consisting essentially of the sequence KRWIILGLNKIVRMY (SEQ ID No: 4).

In yet another embodiment, the T helper epitope peptides are variants of SEQ ID Nos. 2, 3 or 4, which have 1 to 3 additional amino acids (1, 2 or 3), on the N- or C-terminal of these sequences.

The CBD1 peptide or the CBD1 peptide variants can be fused to the T helper epitopes through a linker. Any linker can be used in the present invention such as peptide having the sequence KK, GPGPG, GG, GGG, GGGG, GGA, GA, GD, GSGGGG, GSGGGGS, GS, GPSL, RS, RR, KKK, KKAA, VE, and AAY. In one aspect, the linker used to connect the CBD1 peptide or CBD1 peptide variant to the T helper epitope is a dilysine linker (KK) or a glycine proline linker (GPGPG). Chimeric peptides could also be designed by using as spacers, beta-, gamma- and delta-amino acids; such as delta-aminovaleric acid, gamma-aminobutyric acid and epsilon-aminocaproic acid.

The present invention thus relates to antibodies directed against chimeric peptides comprising or consisting essentially of or consisting of a caveolin-1 binding domain (or variants) of an HIV-1 peptide fused to a T helper epitope, in particular a T helper epitope of a peptide selected from a tetanus toxin peptide, an HIV-1 Gag-p24 peptide or an HIV-1 Env-gp 120 peptide. These antibodies recognize the CBD1 moiety of the chimeric peptide. These antibodies can be polyclonal, monoclonal or oligoclonal. In another aspect, these antibodies are neutralizing antibodies. In a further aspect, the antibodies are monoclonal (mAb) and able to neutralize HIV-1. The antibodies can be directed towards at least one chimeric peptide of SEQ ID Nos. 5 to 25, of SEQ ID Nos 31 to 38 and 52 to 59 or of SEQ ID No 39, at least one peptide of SEQ ID Nos. 1 or 26 to 30 or at least one of peptides SEQ ID Nos. 1 or 26 to 30 fused to at least one of SEQ ID Nos. 2 to 4. In a particular aspect, the antibodies are directed to and recognize:

- a determinant located in the CBD1 moiety of a chimeric peptide of SEQ ID Nos. 5 to 25, of SEQ ID Nos 31 to 38 and 52 to 59 or of SEQ ID No 39;
- a determinant of a peptide of SEQ ID Nos. 1 or 26 to 30;
- a determinant located in a peptide as defined in SEQ ID Nos. 1 or 26 to 30, said peptide being fused to a T helper epitope;
- a determinant located in a peptide as defined in SEQ ID Nos. 1 or 26 to 30, said peptide being fused to a T helper epitope selected from the group consisting of a tetanus toxin, an HIV-1 Gag-p24 and an HIV-1 Env-gp120;
- a determinant located in a peptide as defined in SEQ ID Nos. 1 or 26 to 30, said peptide being fused to at least one peptide of SEQ ID Nos. 2 to 4;

In another aspect, monoclonal antibodies are provided against at least one of SEQ ID Nos. 22 to 24.

The antibodies of the invention have the capacity to recognize the gp41 protein, and in particular at least one epitope or determinant of the CBD1 peptide, both on the free virus and on HIV-1-infected cells. The effect of the antibodies of the invention on the neutralization of HIV-1 can thus be obtained:

- by neutralizing the HIV-1 free viruses, and preventing the infection of new healthy cells; and
- by recruiting effector cells or molecules involved in the ADCC (Antibody dependent cell mediated cytotoxicity) and CDC (complement dependent cytotoxicity) mechanisms, to lead to a cytotoxic effect and destruction of the infected cells.

These antibodies can be made by conventional methods known in the art and can be further purified by known methods. In one aspect, the antibodies and monoclonal antibodies of the invention are obtained by administrating to a mammal, in particular to a human, the chimeric peptides of the invention. The antibodies obtained following the administration have the capacity to recognize the CBD1 moiety of the chimeric peptide, and in particular at least one determinant(s) of the CBD1 moiety of this chimeric peptide. It should be understood that a single chimeric peptide can induce the production of different antibodies that recognize different determinants on the same chimeric peptide (see for example C17K, in Tables 10 and 11, inducing 3 different monoclonal antibodies, each recognizing a different determinant). Such determinants consist essentially of or consist of a determinant disclosed in the last column of Table 11 (SEQ ID Nos 48 to 51) or are comprised in or consist essentially of or consist of the following sequences:

| | | |
|---|---|---|
| CBD1: | SLEQIWNNMTWMQWDK | (SEQ ID No: 1) |
| A36K: | Tet-KKCKSLEQIWNNMTWMQWDK | (SEQ ID No: 5) |
| A35K: | Tet-KKCSLEQIWNNMTWMQWDK | (SEQ ID No: 6) |
| A30K: | Tet-KKIWNNMTWMQWDK | (SEQ ID No: 9) |
| K30K: | gp120-KKIWNNMTWMQWDK | (SEQ ID No: 11) |
| K27W: | Gag-KK-IWNNMTWMQW | (SEQ ID No: 12) |
| K27M: | Gag-KK C-SLEQIWNNM | (SEQ ID No: 14) |
| R33K: | R-G-D-Tet-KKIWNNMTWMQWDK | (SEQ ID No: 20) |

-continued

| | | |
|---|---|---|
| p62: | ASWSNKSLDDIWNNM | (SEQ ID No: 24) |
| C17K: | CSLEQIWNNMTWMQWDK | (SEQ ID No: 31) |
| C10M: | CSLEQIWNNM | (SEQ ID No: 32) |
| C13K: | CIWNNMTWMQWDK | (SEQ ID No: 33) |
| K29K: | Gag-KK-IWNNMTWMQWDK | (SEQ ID No: 34) |
| K24W: | Gag-KK-IWNNMTW | (SEQ ID No: 35) |
| K23M: | Gag-K-K-IWNNM | (SEQ ID No: 36) |
| K30W(G): | Gag-GPGPG-IWNNMTWMQW | (SEQ ID No: 16) |
| K27W(G): | Gag-GPGPG-IWNNMTW | (SEQ ID No: 38) |
| CBD2: | CSLTPDWNNMTWQEWER | (SEQ ID No: 40) |
| CBD2: | SLTPDWNNMTWQEWER | (SEQ ID No: 43) |

The invention also concerns a method to produce antibodies and monoclonal antibodies neutralizing HIV-1, comprising (a) administrating at least one chimeric peptide(s) of the invention to a mammal; and (b) recovering the antibodies or monoclonal antibodies having the specificity against the desired determinants. The recovering of the antibodies may be carried out by putting in contact a sample (e.g., blood) from the mammal to which the at least one chimeric peptide(s) was administrated, with various peptides containing the desired determinants, and eluting the antibodies. In one aspect, the sample is put in contact with a complex to which the peptides containing the desired determinants are fixed. In one aspect, the determinants used to recover the antibodies are a determinant disclosed in the last column of Table 11 (SEQ ID Nos 48 to 51) or a determinant comprised in or consisting essentially of or consisting of SEQ ID NO: 1, 5, 6, 9, 11, 12, 14, 20, 23, 24, 31-38, 52 to 59, 40 or 43.

In a further aspect, the invention also concerns a method to check that the administration of at least one chimeric peptide(s) to a mammal, such as a human, has lead to the induction of antibodies able to neutralize HIV-1. Said method comprises (a) providing a sample from a patient administrated with at least one chimeric peptide(s) of the invention; (b) putting in contact said sample with peptides containing CBD1 determinants in conditions enabling the binding of the antibodies to the peptides; and (c) if possible, identifying for each peptide the formation of an antibody/peptide complex. In one aspect, the determinants used to check the induction of neutralizing antibodies are a determinant disclosed in the last column of Table 11 (SEQ ID Nos 48 to 51) or a determinant comprised in or consisting essentially of or consisting of SEQ ID NO: 1, 5, 6, 9, 11, 12, 14, 20, 23, 24, 31-38, 52 to 59, 40 or 43.

The antibodies and monoclonal antibodies of the invention can be used in immunotherapy to treat or to prevent HIV-1 and/or HIV-1 infection. The antibodies can thus be used in immunotherapy either alone or coupled to a solid particulate matrix. The antibodies whether polyclonal, monoclonal or oligoclonal antibodies, antibodies with a restricted specificity and/or neutralizing antibodies can be administered with a pharmaceutically acceptable vehicle.

A composition or a pharmaceutical composition comprising at least one, preferably one chimeric peptide, several chimeric peptides or chimeric peptide variants as described above, or the antibodies as described above and a physiologically acceptable diluent is another embodiment of the present invention. Thus a composition or a pharmaceutical composition comprising or consisting essentially of or consisting of a chimeric peptide or several chimeric peptides comprising or consisting essentially of or consisting of a caveolin-1 binding domain of an HIV-1 gp41 peptide (or variants) fused to a T helper epitope, in particular a T helper epitope of a peptide selected from the group consisting of a tetanus toxin, an HIV-1 Gag p24 and an HIV-1 Env-gp120, and a physiologically acceptable diluent or a pharmaceutically acceptable vehicle is provided.

More specifically, the compositions of the present invention comprise or consist essentially of or consist of a chimeric peptide or several chimeric peptides of the formulas:
- T helper tetanus toxin epitope-WNNMTWMQW (SEQ ID No. 26);
- T helper epitope of an HIV-1 Gag p24 peptide-WNNMTWMQW (SEQ ID No. 26); or
- T helper HIV-1 epitope HIV-1 Env-gp120 peptide-WNNMTWMQW (SEQ ID No. 26);

and a physiologically acceptable diluent or pharmaceutically acceptable vehicle.

In another embodiment, the present invention relates to compositions or pharmaceutical compositions comprising or consisting essentially of or consisting of variant chimeric peptides of the formulas:
- T helper tetanus toxin epitope-$X_n$WNNM (SEQ ID NO: 27) where X is any amino acid and n is a number from 1 to 6;
- T helper epitope of an HIV-1 Gag p24 peptide-$X_n$WNNM (SEQ ID NO: 27) where X is any amino acid and n is a number from 1 to 6;
- T helper HIV-1 epitope HIV-1 Env-gp120 peptide-$X_n$-WNNM (SEQ ID NO: 27) where X is any amino acid and n is a number from 1 to 6; or
- mixtures thereof or mixtures with the chimeric peptides of SEQ ID No: 26, disclosed above, and a physiologically acceptable diluent or pharmaceutically acceptable vehicle.

In another aspect the present invention relates to pharmaceutical compositions or compositions comprising or consisting essentially of or consisting of variant chimeric peptides of the formulas:
- T helper tetanus toxin epitope-$X_n$WNNMTW (SEQ ID No: 28) where X is any amino acid and n is a number from 1 to 3; T helper epitope of an HIV-1 Gag p24 peptide-$X_n$WNNMTW (SEQ ID No: 28) where X is any amino acid and n is a number from 1 to 3;
- T helper HIV-1 epitope HIV-1 Env-gp120 peptide-XnWNNMTW (SEQ ID No: 28) where X is any amino acid and n is a number from 1 to 3; or
- mixtures thereof or mixtures with the chimeric peptides of SEQ ID No: 26 and or SEQ ID No. 27, disclosed above, and a physiologically acceptable diluent or pharmaceutically acceptable vehicle.

In yet another aspect, the compositions or pharmaceutical compositions comprising or consisting essentially of or consisting of variant chimeric peptides of the invention have the formula:
- T helper tetanus toxin epitope-$X_n$WNNMTWMQWZ$_p$ (SEQ ID No: 29) where X and Z are any amino acid, n is a number from 1 to 6 and p is a number from 0 to 3 preferably 1 to 3;
- T helper epitope of an HIV-1 Gag p24 peptide-$X_n$WNNMTWMQWZ$_p$ (SEQ ID No: 29) where X and Z are any amino acid, n is a number from 1 to 6 and p is a number from 0 to 3, preferably 1 to 3;
- T helper HIV-1 epitope HIV-1 Env-gp120 peptide-$X_n$WNNMTWMQWZ$_p$ (SEQ ID No: 29) where X and Z are any amino acid, n is a number from 1 to 6 and p is a number from 0 to 3, preferably 1 to 3;
- mixtures thereof or mixtures with at least one chimeric peptide of SEQ ID No: 26 to 28, disclosed above, and a physiologically acceptable diluent or pharmaceutically acceptable vehicle.

In yet another embodiment, the compositions or pharmaceutical compositions comprising or consisting essentially of or consisting of variant chimeric peptides of the invention having the formula:
- T helper tetanus toxin epitope-$X_n$WNNMTWMQWZ (SEQ ID No: 30) where X is any amino acid, n is a number from 1 to 6 and Z is D-K;
- T helper epitope of an HIV-1 Gag p24 peptide-$X_n$WNNMTWMQWZ (SEQ ID No: 30) where X is any amino acid, n is a number from 1 to 6 and Z is D-K;
- T helper HIV-1 epitope HIV-1 Env-gp120 peptide-$X_n$WNNMTWMQWZ (SEQ ID No: 30) where X is any amino acid, n is a number from 1 to 6 and Z is D-K; or
- mixtures thereof or mixtures with at least one chimeric peptide of SEQ ID No: 26 to 29, disclosed above, and a physiologically acceptable diluent or pharmaceutically acceptable vehicle.

It should be noted that the symbol "-" in the above chimeric peptide formulas means that the peptides are fused.

A particular mixture comprising various chimeric peptides of the invention (as defined above), usable in compositions, pharmaceutical or immunogenic compositions or vaccines, are the ones consisting of SEQ ID NO: 12 (K27W), SEQ ID NO:35 (K24W), SEQ ID NO:16 (K30W(G)) and SEQ ID NO:38 (K27W(G)), and optionally SEQ ID NO:31 (C17K).

The compositions or pharmaceutical compositions comprising or consisting essentially of or consisting of a chimeric peptide selected from the group of: A-Q-Y-I-K-A-N-S-K-F-I-G-I-T-E-L-K-K-C-K-S-L-E-Q-I-W-N-N-M-T-W-M-Q-W-D-K (SEQ ID No: 5), A-Q-Y-I-K-A-N-S-K-F-I-G-I-T-E-L-K-K-C-S-L-E-Q-I-W-N-N-M-T-W-M-Q-W-D-K (SEQ ID No:6), K-Q-I-I-N-M-W-Q-V-V-G-K-A-M-Y-A-K-K-C-K-S-L-E-Q-I-W-N-N-M-T-W-M-Q-W-D-K (SEQ ID No: 7), K-R-W-I-I-L-G-L-N-K-I-V-R-M-Y-K-K-C-K-S-L-E-Q-I-W-N-N-M-T-W-M-Q-W-D-K (SEQ ID No: 8), A-Q-Y-I-K-A-N-S-K-F-I-G-I-T-E-L-K-K-W-N-N-M-T-W-M-Q-W-D-K (SEQ ID No: 9), K-R-W-I-I-L-G-L-N-K-I-V-R-M-Y-K-K-I-W-N-N-M-T-W-M-Q-W-D-K (SEQ ID No: 10), K-Q-M-N-M-W-Q-V-V-G-K-A-M-Y-A-K-K-I-W-N-N-M-T-W-M-Q-W-D-K (SEQ ID No: 11), K-R-W-I-I-L-G-L-N-K-I-V-R-M-Y-K-K-I-W-N-N-M-T-W-M-Q-W (SEQ ID No: 12), K-R-W-M-L-G-L-N-K-I-V-R-M-Y-K-K-I-W-N-N-M-T-W (SEQ ID No: 13), K-R-W-I-I-L-G-L-N-K-I-V-R-M-Y-K-K-C-S-L-E-Q-I-W-N-N-M (SEQ ID No: 14), K-R-W-I-I-L-G-L-N-K-I-V-R-M-Y-K-K-C-I-W-N-N-M (SEQ ID No: 15), K-R-W-I-I-L-G-L-N-K-I-V-R-M-Y-G-P-G-P-G-I-W-N-N-M-T-W-M-Q-W (SEQ ID No: 16), K-R-V-V-I-I-L-G-L-N-K-I-V-R-M-Y-G-P-G-P-G-I-W-N-N-M-T-W (SEQ ID No: 17), K-R-W-I-I-L-G-L-N-K-I-V-R-M-Y-K-K-I-W-D-N-M-T-W-M-E-W-E-R (SEQ ID No: 18), K-R-W-I-I-L-G-L-N-K-I-V-R-M-Y-K-K-I-W-D-N-M-T-W-M-E-W (SEQ ID No: 19), R-G-D-A-Q-Y-I-K-A-N-S-K-F-I-G-I-T-E-L-K-K-I-W-N-N-M-T-W-M-Q-W-D-K (SEQ ID No: 20), R-G-D-K-R-W-I-I-L-G-L-N-K-I-V-R-M-Y-K-K-I-W-N-N-M-T-W-M-Q-W-D-K (SEQ ID No: 21), R-G-D-K-R-W-I-I-L-G-L-N-K-I-V-R-M-Y-K-K-I-W-N-N-M-T-W-M-Q-W (SEQ ID No: 22), C-I-W-N-N-M-T-W-M-Q-W-D-K (SEQ ID No: 33), K-R-W-I-I-L-G-L-N-K-I-V-R-M-Y-K-K-I-W-N-N-M-T-W-M-Q-W-D-K (SEQ ID No: 34), K-R-W-I-I-L-G-L-N-K-I-V-R-M-Y-K-K-I-W-N-N-M-T-W (SEQ ID No: 35), K-R-W-I-I-L-G-L-N-K-I-V-R-M-Y-K-K-I-W-N-N-M (SEQ ID No: 36), K-R-

W-I-I-L-G-L-N-K-I-V-R-M-Y-G-P-G-P-G-I-W-N-N-M-T-W-M-Q-W (SEQ ID No: 37), K-R-W-I-I-L-G-L-N-K-I-V-R-M-Y-G-P-G-P-G-I-W-N-N-M-T-W (SEQ ID No: 38), and mixtures thereof, as well as A-Q-Y-I-K-A-N-S-K-F-I-G-I-T-E-L-K-K-I-W-N-N-M-T-W-M-Q-W (SEQ ID NO:52), A-Q-Y-I-K-A-N-S-K-F-I-G-I-T-E-L-K-K-I-W-N-N-M-T-W (SEQ ID NO:53), A-Q-Y-I-K-A-N-S-K-F-I-G-I-T-E-L-G-P-G-P-G-I-W-N-N-M-T-W-M-Q-W (SEQ ID NO:54), A-Q-Y-I-K-A-N-S-K-F-I-G-I-T-E-L-G-P-G-P-G-I-W-N-N-M-T-W (SEQ ID NO:55), K-Q-I-I-N-M-W-Q-V-V-G-K-A-M-Y-A-K-K-I-W-N-N-M-T-W-M-Q-W (SEQ ID NO:56), K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58) and K-Q-I-I-N-M-W-Q-V-V-G-K-A-M-Y-A-G-P-G-P-G-I-W-N-N-M-T-W (SEQ ID NO:59) and mixtures thereof, and mixtures of any of the above-mentioned peptides; and a physiologically acceptable diluent or pharmaceutically acceptable vehicle, is another aspect of the invention.

These compositions or pharmaceutical compositions may also further comprise the C18K peptide (SEQ ID NO: 42), the peptide as defined in SEQ ID No: 31 (C17K), the peptide as defined in SEQ ID No: 32 (C10M) and/or the peptide as defined in SEQ ID No: 39 (CBD1/A), together with one or several of the mentioned chimeric peptide(s).

Compositions or pharmaceutical compositions comprising or consisting essentially of or consisting of antibodies such as polyclonal antibodies, monoclonal antibodies, oligoclonal antibodies, antibodies with a restricted specificity and/or neutralizing antibodies raised against the chimeric peptides or chimeric peptide variants as disclosed above are also part of an embodiment of the invention. In another aspect antibodies directed against the peptides SLEQIWNNMTWMQWDK (SEQ ID No: 1), IWNNMTWMQWDK (SEQ ID No: 23), (p62) ASWSNKSLDDIWNNM (SEQ ID No: 24), the chimeric peptides and chimeric peptide variants as described above and mixtures thereof are another aspect of the present invention. In yet another aspect monoclonal antibodies directed against the peptides SLEQIWNNMTWMQWDK (SEQ ID No: 1), IWNNMTWMQWDK (SEQ ID No: 23), (p62) ASWSNKSLDDIWNNM (SEQ ID No: 24), the chimeric peptides and chimeric peptide variants as described above and mixtures thereof, and a physiologically acceptable diluent or pharmaceutically acceptable vehicle are part of the invention.

The physiologically acceptable diluent or pharmaceutically acceptable vehicle can be buffering agents, saline, phosphate buffered saline, dextrose, glycerol, water, ethanol and the like and combinations thereof.

In addition, adjuvants can comprise part of the composition or pharmaceutical composition. Various adjuvants are known in the art and include Complete Freund's Adjuvant (CFA), Incomplete Freund's Adjuvant (IFA), montanide ISA (incompletre seppic adjuvant), muramyl peptides such as muramyl dipeptide (MDP) MDP-Lys (L18) (N$^\alpha$-acetylemuramyl-L-alanyl-D-isoglutaminyl-N$^\epsilon$-steoroyl-L-lysine), aluminum hydroxide (alum), CpG oligodeoxynucleotides (CPG ODN) such as CPG ODN 1826 and CPG ODN 2007, and MF59, which is a detergent stabilized oil-in water emulsion containing 5% squalene (w/v), 0.5% Tween® 80 (w/v) and 0.5% Span (w/v) in water.

An immunogenic composition comprising the chimeric peptide or chimeric peptide variants as described above or the antibodies as described above and a physiologically acceptable diluent is another embodiment of the present invention. An immunogenic composition comprising or consisting essentially of or consisting of a chimeric peptide comprising or consisting essentially of or consisting of a caveolin-1 binding domain of an HIV-1 gp41 peptide fused to a T helper epitope, in particular a T helper epitope of a of a peptide selected from the group consisting of a tetanus toxin, an HIV-1 Gag p24 and an HIV-1 Env-gp120, is another aspect of the invention.

More specifically, the compositions of the present invention comprise or consist essentially of or consist of a chimeric peptide of the formulas:
  T helper tetanus toxin epitope-WNNMTWMQW (SEQ ID No. 26);
  T helper epitope of an HIV-1 Gag p24 peptide-WNNMTWMQW (SEQ ID No. 26); or
  T helper HIV-1 epitope HIV-1 Env-gp120 peptide-WNNMTWMQW (SEQ ID No. 26); and a physiologically acceptable diluent or pharmaceutically acceptable vehicle.

In another embodiment, the present invention relates to immunogenic compositions comprising or consisting essentially of or consisting of variant chimeric peptides of the formulas:
  T helper tetanus toxin epitope-$X_n$WNNM (SEQ ID NO: 27) where X is any amino acid and n is a number from 1 to 6;
  T helper epitope of an HIV-1 Gag p24 peptide-$X_n$WNNM (SEQ ID NO: 27) where X is any amino acid and n is a number from 1 to 6;
  T helper HIV-1 epitope HIV-1 Env-gp120 peptide-$X_n$-WNNM (SEQ ID NO: 27) where X is any amino acid and n is a number from 1 to 6; or
  mixtures thereof or mixtures with the chimeric peptides of SEQ ID No: 26, disclosed above,
and a physiologically acceptable diluent or pharmaceutically acceptable vehicle.

In another aspect the present invention relates to immunogenic compositions comprising or consisting essentially of or consisting of variant chimeric peptides of the formulas:
  T helper tetanus toxin epitope-$X_n$WNNMTW (SEQ ID No: 28) where X is any amino acid and n is a number from 1 to 3;
  T helper epitope of an HIV-1 Gag p24 peptide-$X_n$WNNMTW (SEQ ID No: 28) where X is any amino acid and n is a number from 1 to 3;
  T helper HIV-1 epitope HIV-1 Env-gp120 peptide-$X_n$WNNMTW (SEQ ID No: 28) where X is any amino acid and n is a number from 1 to 3; or
  mixtures thereof or mixtures with the chimeric peptides of SEQ ID No: 26 and/or SEQ ID No. 27, disclosed above,
and a physiologically acceptable diluent or pharmaceutically acceptable vehicle.

In yet another aspect the to immunogenic compositions comprising or consisting essentially of or consisting of variant chimeric peptides of the invention have the formula:
  T helper tetanus toxin epitope-$X_n$WNNMTWMQW$Z_p$ (SEQ ID No: 29) where X and Z are any amino acid, n is a number from 1 to 6 and p is a number from 1 to 3;
  T helper epitope of an HIV-1 Gag p24 peptide-$X_n$WNNMTWMQW$Z_p$ (SEQ ID No: 29) where X and Z are any amino acid, n is a number from 1 to 6 and p is a number from 1 to 3;
  T helper HIV-1 epitope HIV-1 Env-gp120 peptide-$X_n$WNNMTWMQW$Z_p$ (SEQ ID No: 29) where X and Z are any amino acid, n is a number from 1 to 6 and p is a number from 1 to 3; or
  mixtures thereof or mixtures with at least one chimeric peptide of SEQ ID No: 26 to 28, disclosed above, and a physiologically acceptable diluent or pharmaceutically acceptable vehicle.

In yet another embodiment the immunogenic compositions comprising or consisting essentially of or consisting of variant chimeric peptides of the invention having the formula:

T helper tetanus toxin epitope-$X_n$WNNMTWMQWZ (SEQ ID No: 30) where X is any amino acid, n is a number from 1 to 6 and Z is D-K;

T helper epitope of an HIV-1 Gag p24 peptide-$X_n$WNNMTWMQWZ (SEQ ID No: 30) where X is any amino acid, n is a number from 1 to 6 and Z is D-K;

T helper HIV-1 epitope HIV-1 Env-gp120 peptide-$X_n$WNNMTWMQWZ (SEQ ID No: 30) where X is any amino acid, n is a number from 1 to 6 and Z is D-K; or mixtures thereof or mixtures with at least one chimeric peptide of SEQ ID No: 26 to 29, disclosed above, and a physiologically acceptable diluent or pharmaceutically acceptable vehicle.

It should be noted that the symbol "-" in the above chimeric peptide formulas means that the peptides are fused.

The immunogenic compositions comprising or consisting essentially of or consisting of a chimeric peptide selected from the group of: A-Q-Y-I-K-A-N-S-K-F-I-G-I-T-E-L-K-K-C-K-S-L-E-Q-I-W-N-N-M-T-W-M-Q-W-D-K (SEQ ID No: 5), A-Q-Y-I-K-A-N-S-K-F-I-G-I-T-E-L-K-K-C-S-L-E-Q-I-W-N-N-M-T-W-M-Q-W-D-K (SEQ ID No:6), K-Q-I-I-N-M-W-Q-V-V-G-K-A-M-Y-A-K-K-C-K-S-L-E-Q-I-W-N-N-M-T-W-M-Q-W-D-K (SEQ ID No: 7), K-R-W-I-I-L-G-L-N-K-I-V-R-M-Y-K-K-C-K-S-L-E-Q-I-W-N-N-M-T-W-M-Q-W-D-K (SEQ ID No: 8), A-Q-Y-I-K-A-N-S-K-F-I-G-I-T-E-L-K-K-I-W-N-N-M-T-W-M-Q-W-D-K (SEQ ID No: 9), K-R-W-I-I-L-G-L-N-K-I-V-R-M-Y-K-K-I-W-N-N-M-T-W-M-Q-W-D-K (SEQ ID No: 10), K-Q-M-N-M-W-Q-V-V-G-K-A-M-Y-A-K-K-I-W-N-N-M-T-W-M-Q-W-D-K (SEQ ID No: 11), K-R-W-I-I-L-G-L-N-K-I-V-R-M-Y-K-K-I-W-N-N-M-T-W-M-Q-W (SEQ ID No: 12), K-R-W-M-L-G-L-N-K-I-V-R-M-Y-K-K-I-W-N-N-M-T-W (SEQ ID No: 13), K-R-W-I-I-L-G-L-N-K-I-V-R-M-Y-K-K-C-S-L-E-Q-I-W-N-N-M (SEQ ID No: 14), K-R-W-I-I-L-G-L-N-K-I-V-R-M-Y-K-K-C-I-W-N-N-M (SEQ ID No: 15), K-R-W-I-I-L-G-L-N-K-I-V-R-M-Y-G-P-G-P-G-I-W-N-N-M-T-W-M-Q-W (SEQ ID No: 16), K-R-V-V-I-I-L-G-L-N-K-I-V-R-M-Y-G-P-G-P-G-I-W-N-N-M-T-W (SEQ ID No: 17), K-R-W-I-I-L-G-L-N-K-I-V-R-M-Y-K-K-I-W-D-N-M-T-W-M-E-W-E-R (SEQ ID No: 18), K-R-W-I-I-L-G-L-N-K-I-V-R-M-Y-K-K-I-W-D-N-M-T-W-M-E-W (SEQ ID No: 19), R-G-D-A-Q-Y-I-K-A-N-S-K-F-I-G-I-T-E-L-K-K-I-W-N-N-M-T-W-M-Q-W-D-K (SEQ ID No: 20), R-G-D-K-R-W-I-I-L-G-L-N-K-I-V-R-M-Y-K-K-I-W-N-N-M-T-W-M-Q-W-D-K (SEQ ID No: 21), R-G-D-K-R-W-I-I-L-G-L-N-K-I-V-R-M-Y-K-K-I-W-N-N-M-T-W-M-Q-W (SEQ ID No: 22), C-I-W-N-N-M-T-W-M-Q-W-D-K (SEQ ID No: 33), K-R-W-I-I-L-G-L-N-K-I-V-R-M-Y-K-K-I-W-N-N-M-T-W-M-Q-W-D-K (SEQ ID No: 34), K-R-W-I-I-L-G-L-N-K-I-V-R-M-Y-K-K-I-W-N-N-M-T-W (SEQ ID No: 35), K-R-W-I-I-L-G-L-N-K-I-V-R-M-Y-K-K-I-W-N-N-M (SEQ ID No: 36), K-R-W-I-I-L-G-L-N-K-I-V-R-M-Y-G-P-G-P-G-I-W-N-N-M-T-W-M-Q-W (SEQ ID No: 37), K-R-W-I-I-L-G-L-N-K-I-V-R-M-Y-G-P-G-P-G-I-W-N-N-M-T-W (SEQ ID No: 38), and mixtures thereof as well as A-Q-Y-I-K-A-N-S-K-F-I-G-I-T-E-L-K-K-I-W-N-N-M-T-W-M-Q-W (SEQ ID NO:52), A-Q-Y-I-K-A-N-S-K-F-G-I-T-E-L-K-K-I-W-N-N-M-T-W (SEQ ID NO:53), A-Q-Y-I-K-A-N-S-K-F-I-G-I-T-E-L-G-P-G-P-G-I-W-N-N-M-T-W-M-Q-W (SEQ ID NO:54), A-Q-Y-I-K-A-N-S-K-F-I-G-I-T-E-L-G-P-G-P-G-I-W-N-N-M-T-W (SEQ ID NO:55), K-Q-I-I-N-M-W-Q-V-V-G-K-A-M-Y-A-K-K-I-W-N-N-M-T-W-M-Q-W (SEQ ID NO:56), K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58) and K-Q-I-I-N-M-W-Q-V-V-G-K-A-M-Y-A-G-P-G-P-G-I-W-N-N-M-T-W (SEQ ID NO:59) and mixtures thereof, and the mixtures of any of the above-mentioned peptides; and a physiologically acceptable diluent or pharmaceutically acceptable vehicle is another aspect of the invention.

These immunogenic compositions may also further comprise the C18K peptide (SEQ ID NO:42), the peptide as defined in SEQ ID No: 31 (C17K), the peptide as defined in SEQ ID No: 32 (C10M) and/or the peptide as defined in SEQ ID No: 39 (CBD1/A), together with one or several of the mentioned chimeric peptide(s).

Immunogenic compositions comprising or consisting essentially of or consisting of antibodies such as polyclonal antibodies, monoclonal antibodies, oligoclonal antibodies, antibodies with a restricted specificity and/or neutralizing antibodies raised against the chimeric peptides or chimeric peptide variants as disclosed above are also part of an embodiment of the invention. In another aspect antibodies directed against at least one of the peptides SLEQIWNNMTWMQWDK (SEQ ID No: 1), IWNNMTWMQWDK, (SEQ ID No: 23), (p62) ASWSNKSLDDIWNNM (SEQ ID No: 24), the chimeric peptides and chimeric peptide variants as described above and mixtures thereof are another aspect of the present invention. In yet another aspect monoclonal antibodies directed against at least one of the peptides SLEQIWNNMTWMQWDK (SEQ ID No: 1), IWNNMTWMQWDK (SEQ ID No: 23), (p62) ASWSNKSLDDIWNNM (SEQ ID No: 24), the chimeric peptides and chimeric peptide variants as described above and mixtures thereof, and a physiologically acceptable diluent or pharmaceutically acceptable vehicle are part of the invention.

The physiologically acceptable diluent or pharmaceutically acceptable vehicle can be buffering agents, saline, dextrose, glycerol, water, ethanol and the like and combinations thereof.

In addition adjuvants can comprise part of the composition or pharmaceutical composition. Various adjuvants are known in the art and include Complete Freund's Adjuvant (CFA), Incomplete Freund's Adjuvant (IFA), montanide ISA (incompletre seppic adjuvant), muramyl peptides such as muramyl dipeptide (MDP) MDP-Lys (L18) ($N^\alpha$-acetylemuramyl-L-alanyl-D-isoglutaminyl-$N^\epsilon$-steoroyl-L-lysine), aluminum hydroxide (alum), CpG oligodeoxynucleotides(CPG ODN) such as CPG ODN 1826 and CPG ODN 2007, and MF59, which is a detergent stabilized oil-in water emulsion containing 5\% squalene (w/v), 0.5% Tween® 80 (w/v) and 0.5% Span (w/v) in water.

In yet another embodiment the present invention relates to vaccines comprising the chimeric peptide or chimeric peptide variants as described above or the antibodies as described above, and a physiologically acceptable diluent is another embodiment of the present invention. The vaccine comprises or consists essentially of or consists of a chimeric peptide comprising or consisting essentially of or consisting of a caveolin-1 binding domain of an HIV-1 gp41 peptide fused to a T helper epitope, in particular a T helper epitope of a peptide selected from the group consisting of a tetanus toxin, an HIV-1 Gag p24 and an HIV-1 Env-gp120.

More specifically, the compositions of the present invention comprise or consist essentially of or consist of a chimeric peptide of the formulas:

T helper tetanus toxin epitope-WNNMTWMQW (SEQ ID No. 26);

T helper epitope of an HIV-1 Gag p24 peptide-WN-NMTWMQW (SEQ ID No. 26); or

T helper HIV-1 epitope HIV-1 Env-gp120 peptide-WN-NMTWMQW (SEQ ID No. 26), and a physiologically acceptable diluent or pharmaceutically acceptable vehicle.

In another embodiment, the present invention relates to a vaccine comprising or consisting essentially of or consisting of variant chimeric peptides of the formulas:

T helper tetanus toxin epitope-$X_n$WNNM (SEQ ID NO: 27) where X is any amino acid and n is a number from 1 to 6;

T helper epitope of an HIV-1 Gag p24 peptide-$X_n$WNNM (SEQ ID NO: 27) where X is any amino acid and n is a number from 1 to 6;

T helper HIV-1 epitope HIV-1 Env-gp120 peptide-$X_n$-WNNM (SEQ ID NO: 27) where X is any amino acid and n is a number from 1 to 6; or mixtures thereof or mixtures with the chimeric peptides of SEQ ID No: 26, disclosed above, and a physiologically acceptable diluent or pharmaceutically acceptable vehicle.

In another aspect, the present invention relates to a vaccine comprising or consisting essentially of or consisting of variant chimeric peptides of the formulas:

T helper tetanus toxin epitope-$X_n$WNNMTW (SEQ ID No: 28) where X is any amino acid and n is a number from 1 to 3;

T helper epitope of an HIV-1 Gag p24 peptide-$X_n$WN-NMTW (SEQ ID No: 28) where X is any amino acid and n is a number from 1 to 3;

T helper HIV-1 epitope HIV-1 Env-gp120 peptide-$X_n$WN-NMTW (SEQ ID No: 28) where X is any amino acid and n is a number from 1 to 3; or mixtures thereof or mixtures with the chimeric peptides of SEQ ID No: 26 and/or SEQ ID No. 27 disclosed above, and a physiologically acceptable diluent or pharmaceutically acceptable vehicle.

In yet another aspect, the vaccines of the invention comprises or consists essentially of or consists of variant chimeric peptides of the invention having the formula:

T helper tetanus toxin epitope-$X_n$WNNMTWMQWZ$_p$ (SEQ ID No: 29) where X and Z are any amino acid, n is a number from 1 to 6 and p is a number from 1 to 3;

T helper epitope of an HIV-1 Gag p24 peptide-$X_n$WN-NMTWMQWZ$_p$ (SEQ ID No: 29) where X and Z are any amino acid, n is a number from 1 to 6 and p is a number from 1 to 3;

T helper HIV-1 epitope HIV-1 Env-gp120 peptide-$X_n$WN-NMTWMQWZ$_p$ (SEQ ID No: 29) where X and Z are any amino acid, n is a number from 1 to 6 and p is a number from 1 to 3; or mixtures thereof or mixtures with at least one chimeric peptide of SEQ ID Nos: 26 to 28, disclosed above, and a physiologically acceptable diluent or pharmaceutically acceptable vehicle.

In yet another embodiment the vaccines comprising or consisting essentially of or consisting of variant chimeric peptides of the invention having the formula:

T helper tetanus toxin epitope-$X_n$WNNMTWMQWZ (SEQ ID No: 30) where X is any amino acid, n is a number from 1 to 6 and Z is D-K;

T helper epitope of an HIV-1 Gag p24 peptide-$X_n$WN-NMTWMQWZ (SEQ ID No: 30) where X is any amino acid, n is a number from 1 to 6 and Z is D-K;

T helper HIV-1 epitope HIV-1 Env-gp120 peptide-$X_n$WN-NMTWMQWZ (SEQ ID No: 30) where X is any amino acid, n is a number from 1 to 6 and Z is D-K; or mixtures thereof or mixtures with at least one chimeric peptide of SEQ ID Nos: 26 to 29, disclosed above, and a physiologically acceptable diluent or pharmaceutically acceptable vehicle.

It should be noted that the symbol "-" in the above chimeric peptide formulas means that the peptides are fused.

The vaccines (also called cocktail or cocktail vaccines) comprising or consisting essentially of or consisting of a chimeric peptide selected from the group A-Q-Y-I-K-A-N-S-K-F-I-G-I-T-E-L-K-K-C-K-S-L-E-Q-I-W-N-N-M-T-W-M-Q-W-D-K (SEQ ID No: 5), A-Q-Y-I-K-A-N-S-K-F-I-G-I-T-E-L-K-K-C-S-L-E-Q-I-W-N-N-M-T-W-M-Q-W-D-K (SEQ ID No:6), K-Q-I-I-N-M-W-Q-V-V-G-K-A-M-Y-A-K-K-C-K-S-L-E-Q-I-W-N-N-MT-W-M-Q-W-D-K (SEQ ID No: 7), K-R-W-I-I-L-G-L-N-K-I-V-R-M-Y-K-K-C-K-S-L-E-Q-I-W-N-N-M-T-W-M-Q-W-D-K (SEQ ID No: 8), A-Q-Y-I-K-A-N-S-K-F-I-G-I-T-E-L-K-K-I-W-N-N-M-T-W-M-Q-W-D-K (SEQ ID No: 9), K-R-W-I-I-L-G-L-N-K-I-V-R-M-Y-K-K-I-W-N-N-M-T-W-M-Q-W-D-K (SEQ ID No: 10), K-Q-M-N-M-W-Q-V-V-G-K-A-M-Y-A-K-K-I-W-N-N-M-T-W-M-Q-W-D-K (SEQ ID No: 11), K-R-W-I-I-L-G-L-N-K-I-V-R-M-Y-K-K-I-W-N-N-M-T-W-M-Q-W (SEQ ID No: 12), K-R-W-M-L-G-L-N-K-I-V-R-M-Y-K-K-I-W-N-N-M-T-W (SEQ ID No: 13), K-R-W-I-I-L-G-L-N-K-I-V-R-M-Y-K-K-C-S-L-E-Q-I-W-N-N-M (SEQ ID No: 14), K-R-W-I-I-L-G-L-N-K-I-V-R-M-Y-K-K-C-I-W-N-N-M (SEQ ID No: 15), K-R-W-I-I-L-G-L-N-K-I-V-R-M-Y-G-P-G-P-G-I-W-N-N-M-T-W-M-Q-W (SEQ ID No: 16), K-R-V-V-I-I-L-G-L-N-K-I-V-R-M-Y-G-P-G-P-G-I-W-N-N-M-T-W (SEQ ID No: 17), K-R-W-I-I-L-G-L-N-K-I-V-R-M-Y-K-K-I-W-D-N-M-T-W-M-E-W-E-R (SEQ ID No: 18), K-R-W-I-I-L-G-L-N-K-I-V-R-M-Y-K-K-I-W-D-N-M-T-W-M-E-W (SEQ ID No: 19), R-G-D-A-Q-Y-I-K-A-N-S-K-F-I-G-I-T-E-L-K-K-I-W-N-N-M-T-W-M-Q-W-D-K (SEQ ID No: 20), R-G-D-K-R-W-I-I-L-G-L-N-K-I-V-R-M-Y-K-K-I-W-N-N-M-T-W-M-Q-W-D-K (SEQ ID No: 21), R-G-D-K-R-W-I-I-L-G-L-N-K-I-V-R-M-Y-K-K-I-W-N-N-M-T-W-M-Q-W (SEQ ID No: 22), C-I-W-N-N-M-T-W-M-Q-W-D-K (SEQ ID No: 33), K-R-W-I-I-L-G-L-N-K-I-V-R-M-Y-K-K-I-W-N-N-M-T-W-M-Q-W-D-K (SEQ ID No: 34), K-R-W-I-I-L-G-L-N-K-I-V-R-M-Y-K-K-I-W-N-N-M-T-W (SEQ ID No: 35), K-R-W-I-I-L-G-L-N-K-I-V-R-M-Y-K-K-I-W-N-N-M (SEQ ID No: 36), K-R-W-I-I-L-G-L-N-K-I-V-R-M-Y-G-P-G-P-G-I-W-N-N-M-T-W-M-Q-W (SEQ ID No: 37), K-R-W-I-I-L-G-L-N-K-I-V-R-M-Y-G-P-G-P-G-I-W-N-N-M-T-W (SEQ ID No: 38), and mixtures thereof as well as A-Q-Y-I-K-A-N-S-K-F-I-G-I-T-E-L-K-K-I-W-N-N-M-T-W-M-Q-W (SEQ ID NO:52), A-Q-Y-I-K-A-N-S-K-F-I-G-I-T-E-L-K-K-I-W-N-N-M-T-W (SEQ ID NO:53), A-Q-Y-I-K-A-N-S-K-F-I-G-I-T-E-L-G-P-G-P-G-I-W-N-N-M-T-W-M-Q-W (SEQ ID NO:54), A-Q-Y-I-K-A-N-S-K-F-I-G-I-T-E-L-G-P-G-P-G-I-W-N-N-M-T-W (SEQ ID NO:55), K-Q-I-I-N-M-W-Q-V-V-G-K-A-M-Y-A-K-K-I-W-N-N-M-T-W-M-Q-W (SEQ ID NO:56), K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58) and K-Q-I-I-N-M-W-Q-V-V-G-K-A-M-Y-A-G-P-G-P-G-I-W-N-N-M-T-W (SEQ ID NO:59) and mixtures thereof, and the mixtures of any of the above-mentioned peptides; and a physiologically acceptable diluent or pharmaceutically acceptable vehicle is another aspect of the invention.

These vaccines may also further comprise the C18K peptide (SEQ ID NO:42), the peptide as defined in SEQ ID No: 31 (C17K), the peptide as defined in SEQ ID No: 32 (C10M)

and/or the peptide as defined in SEQ ID No: 39 (CBD1/A), together with one or several of the mentioned chimeric peptide(s).

Vaccines comprising or consisting essentially of or consisting of antibodies such as polyclonal antibodies, monoclonal antibodies, oligoclonal antibodies, antibodies with a restricted specificity and/or neutralizing antibodies raised against the chimeric peptides or chimeric peptide variants as disclosed above are also part of an embodiment of the invention. In another aspect, antibodies, directed against at least one of the peptides SLEQIWNNMTWMQWDK (SEQ ID No: 1), IWNNMTWMQWDK (SEQ ID No: 23), (p62) ASWSNKSLDDIWNNM (SEQ ID No: 24), the chimeric peptides and chimeric peptide variants as described above and mixtures thereof, are another aspect of the present invention. In yet another aspect, monoclonal antibodies, directed against at least one of the peptides SLEQIWNNMTWMQWDK (SEQ ID No: 1), IWNNMTWMQWDK (SEQ ID No: 23), (p62) ASWSNKSLDDIWNNM (SEQ ID No: 24), the chimeric peptides and chimeric peptide variants as described above and mixtures thereof and a physiologically acceptable diluent or pharmaceutically acceptable vehicle, are part of the invention.

The physiologically acceptable diluent or pharmaceutically acceptable vehicle can be buffering agents, saline, dextrose, glycerol, water, ethanol and the like and combinations thereof.

In addition, adjuvants can comprise part of the composition or pharmaceutical composition. Various adjuvants are known in the art and include Complete Freund's Adjuvant (CFA), Incomplete Freund's Adjuvant (IFA), montanide ISA (incompletre seppic adjuvant), muramyl peptides such as muramyl dipeptide (MDP) MDP-Lys (L18) (N$^\alpha$-acetylemuramyl-L-alanyl-D-isoglutaminyl-N$^\epsilon$steoroyl-L-lysine), aluminum hydroxide (alum), CpG oligodeoxynucleotides(CPG ODN) such as CPG ODN 1826 and CPG ODN 2007, and MF59. which is a detergent stabilized oil-in water emulsion containing 5% squalene (w/v), 0.5% Tween® 80 (w/v) and 0.5% Span (w/v) in water.

The present invention also relates to a method for treating or neutralizing an HIV-1 infection, said method comprising administering to a mammal in need of such treatment the chimeric peptides or chimeric peptide variants as described above or the antibodies as described above in a physiological acceptable vehicle. In this regard, any of the chimeric peptides comprising, consisting essentially of or consisting of at least one of SEQ ID Nos. 5 to 25 or at least one of SEQ ID Nos. 31 to 39 and 52 to 59 and mixtures thereof, or SEQ ID No. 1, or at least one of SEQ ID Nos. 26 to 30 fused to at least one T helper peptide of SEQ ID Nos. 2 to 4 and mixture thereof can be used in the method for treating HIV-1 infection.

The present invention also encompasses methods for treating HIV-1 infection by administering to a mammal in need of such treatment the antibodies described in the present invention. In this regard the antibodies can be polyclonal, monoclonal, oligoclonal, antibodies with a restricted specificity and/or neutralizing antibodies The invention also concerns a method for neutralizing HIV-1 activity, said method comprising administering to a mammal in need of such treatment a chimeric peptide comprising, consisting essentially of or consisting of at least one chimeric peptides of SEQ ID Nos. 5 to 25, or at least one of SEQ ID Nos. 31 to 39 and 52 to 59, or SEQ ID No. 1 or at least one of SEQ ID Nos. 26 to 30 fused to at least one T helper epitope peptide of SEQ ID Nos. 2 to 4 and mixtures thereof, then further administering a T helper epitope.

As set forth above, in an aspect, the T helper epitope can be from a tetanus toxin peptide, an HIV-1 gp120 peptide and an HIV-1 Gag peptide. More specifically, these peptides are a tetanus toxin Tet$_{830}$ peptide comprising or consisting of or consisting essentially of the sequence AQYIKANSKFIGITEL (SEQ ID No: 2), an HIV-1 gp120$_{421-436}$ peptide comprising or consisting of or consisting essentially of the sequence KQIINMWQVVGKAMYA (SEQ ID No: 3) or an HIV-1 Gag$_{298-312}$ peptide comprising or consisting of or consisting essentially of the sequence KRWIILGLNKIVRMY (SEQ ID No: 4).

The chimeric peptides comprising or consisting essentially of or consisting of a caveolin-1 binding domain of an HIV-1 gp41 peptide fused to a T helper epitope of a peptide, in particular a T helper epitope of a peptide selected from the group of a tetanus toxin, an HIV-1 Gag-p24 and an HIV-1 Env-gp120, can be used as a medicament, for neutralization of HIV-1 or for the treatment of HIV-1 or AIDS or HIV infections or as a prophylaxis for HIV-1. More specifically, the chimeric peptides or peptide variants of at least one of SEQ ID Nos. 5 to 25 or at least one of SEQ ID Nos. 31 to 39 and 52 to 59 or SEQ ID No. 1, or at least one of SEQ ID Nos. 26 to 30 fused to at least one T helper epitope peptides of SEQ ID Nos. 2 to 4 can be used as a medicament, for neutralization of HIV-1 or for the treatment of HIV-1 or AIDS or HIV infections or as a prophylaxis for HIV-1 or the antibodies, especially monoclonal antibodies as described herein and directed against the peptides of SEQ ID Nos. 22 to 24 or directed against the chimeric peptides or chimeric peptide variants of at least one of SEQ ID Nos. 5 to 25, or at least one of SEQ ID Nos. 31 to 38 and 52 to 59, or SEQ ID No 39 or SEQ ID No. 1 or at least one of SEQ ID Nos. 26 to 30 fused to at least one T helper epitope peptide of SEQ ID Nos. 2 to 4 and mixtures thereof can be used as a medicament, for neutralization of HIV-1 or for the treatment of HIV-1 or AIDS or HIV infections or as a prophylaxis for HIV-1.

The chimeric peptides comprising or consisting essentially of or consisting of a caveolin-1 binding domain of an HIV-1 gp41 peptide fused to a T helper epitope, in particular a T helper epitope of a peptide selected from the group of a tetanus toxin, an HIV-1 Gag-p24 and an HIV-1 Env-gp120, can be used for the manufacture of a medicament, for neutralization of HIV-1 or for the treatment of HIV-1 or AIDS or HIV infections or for prophylaxis for HIV-1. More specifically, the chimeric peptides or peptide variants of at least one of SEQ ID Nos. 5 to 25 or at least one of SEQ ID Nos. 31 to 39 and 52 to 59 or SEQ ID No. 1 or at least one of SEQ ID Nos. 26 to 30 fused to at least one T helper epitope peptides of SEQ ID Nos. 2 to 4 can be used in the manufacture of a medicament, for neutralization of HIV-1 or for the treatment of HIV-1 or AIDS or HIV infections or for prophylaxis for HIV-1 or the antibodies, especially monoclonal antibodies as described herein and directed against the peptides of SEQ ID Nos. 22 to 24 or directed against the chimeric peptides or chimeric peptide variants of at least one of SEQ ID Nos. 5 to 25, or at least one SEQ ID Nos. 31 to 38 and 52 to 59 or SEQ ID No: 39 or SEQ ID No. 1 or at least one of SEQ ID Nos. 26 to 30 fused to at least one T helper epitope peptide of SEQ ID Nos. 2 to 4 and mixtures thereof can be used in the manufacture of a medicament, for neutralization of HIV-1 or for the treatment of HIV-1 or AIDS or HIV infections or for prophylaxis for HIV-1.

A number of embodiments of the invention have been described. Nevertheless, it will be understood that various modifications may be made without departing from the spirit and scope of the invention.

EXAMPLES

Materials and Methods

The following materials and methods were used throughout the examples.

1. Materials

Keyhole Limpet hemocyanin (KLH), squalene, Tween 80 and Span 85 (w/v) were purchased from Sigma. Imject® Maleimide Activated KLH (mcKLH; Pierce Biotechnology) was tested as a carrier protein for the CBD1 peptide. Overlapping peptides from the sequence of the HIV-1 MN gp41 at the region of the CBD1 epitope were obtained from AIDS Research and Reference Program/NIAID, NIH (AIDS/NIH). The HIV-1 gp41 recombinant fragment 586-682 produced in *Pichia pastoris* was purchased from Viral Therapeutics, Inc.

Peptides

All peptides at immunograde purity (80-90% pure) were synthesized by NeoMPS, Strasbourg, France. The CBD1 peptide is at amino acid positions 618 to 633 of gp41: SLE-QIWNNMTWMQWDK (SEQ ID No: 1) (Hovanessian et al., 2004). A cysteine residue at the N-terminal end of the CBD1 peptide (C17K) was added in order to couple it to Imject® Activated keyhole limpet hemocyanin (KLH) purchased from Pierce Biotechnology. The amino acid sequence of the T helper epitope peptides are the following: (1) tetanus toxin $Tet_{830}$ peptide, AQYIKANSKFIGITEL (SEQ ID No: 2), (2) HIV-1 $gp120_{421\text{-}436}$ peptide, KQIINMWQVVGKAMYA (SEQ ID No: 3) and (3) HIV-1 $Gag_{298\text{-}312}$ peptide, KRWI-ILGLNKIVRMY (SEQ ID No: 4).

The sequence of CBD1 and CBD1-based peptides are given below with the conserved tryptophan residues in bold letters. The chimeric peptides were synthesized using the dilysine linker (KK) or the glycine-proline (GPGPG) spacer (Lennon-Duménill et al., 2002; Livingston et al., 2002).

```
CBD2:
                                            (SEQ ID No: 40)
C-S-L-T-P-I-W-N-N-M-T-W-Q-E-W-E-R

C17K(CBD1):
                                            (SEQ ID No: 31)
C-S-L-E-Q-I-W-N-N-M-T-W-M-Q-W-D-K

A35K:
                                            (SEQ ID No: 6)
Tet-K-K-C-S-L-E-Q-I-W-N-N-M-T-W-M-Q-W-D-K

K27M:
                                            (SEQ ID No: 14)
Gag-K-K-C-S-L-E-Q-I-W-N-N-M

C10M:
                                            (SEQ ID No: 32)
C-S-L-E-Q-I-W-N-N-M

C13K:
                                            (SEQ ID No: 33)
C-I-W-N-N-M-T-W-M-Q-W-D-K

A30K:
                                            (SEQ ID No: 9)
Tet-K-K-I-W-N-N-M-T-W-M-Q-W-D-K

K29K:
                                            (SEQ ID No: 34)
Gag-K-K-I-W-N-N-M-T-W-M-Q-W-D-K

K30K:
                                            (SEQ ID No: 11)
gp120-K-K-I-W-N-N-M-T-W-M-Q-W-D-K

R33K:
                                            (SEQ ID No: 20)
R-G-D-Tet-K-K-I-W-N-N-M-T-W-M-Q-W-D-K
```

The sequences of the caveolin-1 binding motif-based peptides are the following:

```
K27W:
Gag-K-K-I-W-N-N-M-T-W-M-Q-W          (SEQ ID No: 12)

K24W:
Gag-K-K-I-W-N-N-M-T-W                (SEQ ID No: 35)

K23M:
Gag-K-K-I-W-N-N-M                    (SEQ ID No: 36)

K30W(G):
Gag-G-P-G-P-G-I-W-N-N-M-T-W-M-Q-W    (SEQ ID No: 16)

K27W(G):
Gag-G-P-G-P-G-I-W-N-N-M-T-W          (SEQ ID No: 38)
```

Cysteinyl CBD1 peptide was coupled to mcKLH according to the instructions of the supplier (Pierce Biotechnology).

Adjuvants

Complete and incomplete Freund's adjuvant (CFA and IFA), Muramyl dipeptide referred to as MDP (N-acetyl-muramyl-L-alanyl-D-isoglutamine hydrate), the MDP derivative referred to as MDP-Lys(L18) ($N^{\alpha}$-acetyl muramyl-L-alanyl-D-isoglutaminyl-$N^{e}$-stearoyl-L-lysine) and aluminum hydroxide (alum) were purchased from Sigma. CpG oligodeoxynucleotides (CpG ODN 1826 for mice; CpG ODN 2007 for rabbits and guinea pigs; CpG ODN 10103 for macaques) were purchased from Coley Pharmaceutical Group, USA. The detergent-stabilized oil-in-water emulsion MF59 was prepared in the laboratory. It consisted of 5% squalene (w/v), 0.5% Tween 80 (w/v) and 0.5% Span 85 (w/v) in water (O'Hagan and Rappuoli, 2004). Montanide ISA 51 was generously provided by SEPPIC, France.

2. Methods 2.1 Immunization of Animals and ELISA

Rabbits (Fauves de Bourgogne, 6-week-old) and Guinea pigs (350-400 g) were purchased from Animal Production Center (Olivet, France). BALB/c mice (6-8 week-old) were purchased from Charles River Laboratories (France). Animals were immunized at about 2-3 weeks interval for 5 times, with the CBD1 or CBD1-derived peptides using CFA and IFA (for the experimental data presented here) or the other adjuvants (data not presented). Such suspensions were administered at an equal antigen/adjuvant proportion (1V/1V) in a total volume of 150 µl, 300 µl, and 500 µl in mice, guinea pigs, and rabbits, respectively.

Rabbits were immunized intradermally using CFA for the five injections, guinea pigs were immunized intramuscularly for the first three immunizations followed by two intraperitoneal injections using CFA, whereas mice were immunized subcutaneously for the first immunization using CFA followed by intraperitoneal injections using CFA and IFA as indicated.

The immune sera were titrated by ELISA using 96 well plates (Maxisorp, Dynatech) coated with 2 µM of the various peptides (as indicated) and incubated for 60 min at 37° C. The immune sera were added in serial dilutions and incubated for 60 min at 37° C. After washing, a mouse anti-rabbit (Sigma) or goat anti-guinea pig (Sigma) or sheep anti-mouse (Amersham) immunoglobulin conjugated with horseradish peroxidase (HRP) was added. Following incubation and washing, o-Phenylenediamine dihydrochloride (OPD) substrate was added to the wells as described (Hovanessian et al., 2004; Rey-Cuillé et al., 2006). Following color development the reaction was quantitated at 450 nm. The antibody titers correspond to the reciprocal dilution of the respective rabbit serum giving an OD value equal to 0.1 (measured at 450 nm). The proportion of IgG1 and IgG2 subclass antibodies in the immune sera of mice and guinea pigs was determined using goat anti-mouse IgG1 and IgG2a antibodies (Sigma) and goat anti-guinea pig IgG1 and IgG2 (Nordic Immunology) antibodies, respectively. These goat antibodies were then revealed by HRP-conjugated rabbit anti-goat IgG (Sigma).

2.2. Immunization of Macaques and ELISA

Adult male cynomolgus macaques (*Macaca fascicularis*) weighing 4-6 kg, imported from the Mauritius breeding colony, were maintained and handled in accordance with European guidelines for non-human primate care (EEC Directive N 86-609, 24 Nov. 1986). The animals were sedated with ketamine chlorhydrate (10-15 mg/kg) for immunizations and blood sample collections. In the first set of immunization, animals were immunized with the cysteinyl CBD1 peptide (200 µg) via the intradermal (i.d.) or intramuscular (i.m.) route using as adjuvant [MF59+MDP-Lys(L18)]. The control macaques were injected with the adjuvant alone. In the second set of immunization, animals were immunized subcutaneously with Tet-KK-CBD1 (400 µg) or with CBD1+ $Tet_{4830}$ peptide (200 µg+150 µg) using as adjuvant the mixture composed of [CpG+Montanide ISA 51]. For each immunization, 500 µl consisting of one volume of immunogen with one volume of adjuvant mixture were administered. In general, animals were bled 15 days after each immunization in order to monitor the immune response.

The immune sera were titrated by ELISA using 96 well plates (Maxisorp, Dynatech) coated with 2 µM of the various peptides (as indicated) and incubated for 60 min at 37° C. The immune sera were added in serial dilutions and incubated for 60 min at 37° C. After washing, sheep anti-human IgG conjugated with horseradish peroxidase (GE Healthcare, UK Limited) was added. (It should be noted that the detection of monkey IgG with anti-monkey antibodies give higher background levels compared to anti-human antibodies.) Following incubation and washing, o-Phenylenediamine dihydrochloride (OPD) substrate was added to the wells as described (Hovanessian et al., 2004; Rey-Cuillé et al., 2006). Following color development the reaction was quantitated at 450 nm. The antibody titers correspond to the reciprocal dilution of the respective rabbit serum giving an OD value equal to 0.1 (measured at 450 nm).

2.3. Assay of HIV Infection in Primary T Lymphocytes $CD4^+$ T lymphocytes were propagated in RPMI-1640 containing 10% heat inactivated fetal-calf serum and 50 IU/ml penicillin-streptomycin. $CD4^+$ lymphocytes were prepared from PBMC after depletion of $CD8^+$ cells using Dynabeads M-450 CD8 (Dynal® Invitrogen). After 3 days stimulation with PHA, cells were suspended in fresh culture medium containing IL-2 and infected after 72 hours with the primary HIV-1 isolate BZ167 (Hovanessian et al., 2004; Rey-Cuillé et al., 2006). The inhibitory activity of anti-CBD1 immune sera against HIV infection was assayed by preincubation (37° C., 20 min) of a given HIV isolate with various dilutions of the immune serum before incubation (37° C., 90 min) with permissive cells. The maximum peak of virus production in such primary $CD4^+$ cells occurs at 4-5 days post-infection. Cells were passaged on day 3 and virus production was monitored in culture supernatants by ELISA to measure the concentration of the HIV major core protein p24 (HIV-1 p24 ELISA kit, Perkin-Elmer). The values obtained in different experiments are the mean±SD in ng/ml of triplicate samples.

2.4. Single-Round HIV-1 Infectivity Assay

For the assay of HIV infectivity, culture supernatants at serial dilutions were used to infect HeLa P4 cells containing the LacZ gene under the control of HIV-1 long terminal repeat (LTR). HIV-1 entry and replication result in the activation of the HIV-1 LTR, leading to the expression of β-galactosidase. At 48 hours post-infection, cells are washed and the β-galactosidase activity is measured using a 570-nm wavelength filter as described (Nisole et al., 2000).

2.5. IFN-γ ELISPOT Assays

Cellular immune response against the CBD1 peptide in macaques immunized either intradermally (i.d.) or intramuscularly (i.m.). The responses were obtained by stimulating the PBMC, sampled at the indicated day, with CBD1 peptide in IFN-γ ELISPOT assays. MultiScreen 96-well filtration plates (Millipore, Guyancourt, France) were wet with ethanol 35% in water for 30 seconds then washed 3 times with sterile apyrogenic water followed by an additional wash with PBS. The plates were then coated by incubation overnight with monoclonal antibody against monkey IFN-γ (clone GZ-4, Mabtech AB, Sophia Antipolis, France) at the concentration of 10 µg/ml in PBS, at 4° C. Plates were washed 6 times with PBS then blocked by incubation for 2 h at 37° C. in Roswell Park Memorial Institute (RPMI) 1640 medium with glutamax-1 (Invitrogen) supplemented with 10% heat-inactivated fetal calf serum (FCS, Laboratoires Eurobio; culture medium). Peripheral blood mononuclear cells (PBMC) were recovered by density gradient centrifugation and $2 \times 10^5$ cells were added to each well. Peptides were then added in triplicate to a final concentration of 1 µM in culture medium. Phorbol 12-myristate 13-acetate (PMA) (Sigma-Aldrich, Saint-Quentin Fallavier, France) plus ionomycine (Sigma-Aldrich), at a final concentration of 0.1 µM and 1 µM, respectively, was used as positive control. Culture medium alone was used as negative control. Plates were incubated for 18 h at 37° C. in an atmosphere containing 5% $CO_2$. They were then washed 5 times with PBS and incubated overnight at 4° C. with biotinylated anti-IFN-γ antibody (clone 7-B6-1, Mabtech AB) at a concentration of 1 µg/mL in PBS containing 0.5% FCS. Plates were washed 5 times with PBS, incubated with 0.25 µg/mL alkaline phosphatase-streptavidin conjugate (Sigma-Aldrich) for 1 h at 37° C., and washed 5 times with PBS. Spots were developed by adding 80 µl/well of NBT/BCIP substrate (Sigma-Aldrich). The spots were counted with an Automated Elispot Reader System with KS software (Carl Zeiss, Le Pecq, France). The results are expressed as mean of IFN-γ spot-forming cells per $10^6$ PBMC (IFN-γ SFC/million PBMC) of triplicate wells. The background was calculated as twice the mean number of IFN-γ SFC/million PBMC in non-stimulated samples. Samples yielding more than 50 IFN-γ SFC/million PBMC after removal of the background were scored as positive.

Example 1

Generating the Peptide Sequences

All peptides in the following examples were synthesized by NeoMPS Strasbourg, France using methods known in the art. All peptides were at immunograde purity of 80%-90%.

Unless otherwise indicated, in examples 2, 3, 4, 5, 6, 8, 10 and 11 (and FIGS. 4, 5, 7, 16 and 17), the term "CBD1" refers to the CBD1-based peptide C17K (SEQ ID NO:31). In example 9 (and FIGS. 9-15), the term "CBD1" refers to the CBD1-based peptide C18K (SEQ ID NO:42).

Example 2

Comparison of the Immunogenicity of the CBD1 Peptides Adjuvanted with CFA as a Free Peptide or Conjugated to Carrier Proteins A series of experiments were performed in rabbits to compare the immunogenicity of the CBD1 peptide adjuvanted with Complete Freund's Adjuvant (CFA), either as free peptide or conjugated to carrier proteins, such as streptavidin and ovalbumin.

The inhibitory activity of immune sera was assayed at different dilutions against infection of primary $CD4^+$ T lymphocytes with the primary HIV-1 BZ 167 isolate as described by Hovanessian et al., 2004b.

In order to evaluate the efficacy of KLH as a carrier protein for the CBD1 peptide, rabbits were injected either with the cysteinyl-CBD1 peptide or the cysteinyl-CBD1 peptide conjugated to KLH using CFA as adjuvant. The KLH coupled CBD1 peptide was found to be a very poor immunogen (Table 1). The lack of reactivity of the KLH-coupled CBD1 peptide might be due to the loss of its structure when coupled to KLH, since in an ELISA assay and -CBD1 antibodies react poorly with the KLH-CBD1 construct. Whatever is the case, the cysteinyl CBD1 peptides (C17K and C18K) were shown to be highly immunogenic as they elicited the production of neutralizing antibodies. Consequently, in further immunization experiments free cysteinyl-CBD1-based peptides, i.e. without a carrier protein were used.

The cysteinyl-CBD1 peptides (C17K, C18K) are highly immunogenic, whereas when coupled to ovalbumin their immunogenicity is reduced by 50%. On the other hand the free biotinyl-CBD1 peptide is not immunogenic, whereas when coupled to streptavidin its immunogenicity is comparable to that of the cysteinyl-CBD1 peptides (Hovanessian et al., 2004b). Immune serum from rabbits immunized with the cysteinyl-CBD1 peptide and the biotinyl-CBD1 peptide coupled to streptavidin has the capacity to inhibit HIV-1 infection (Table 1).

TABLE 1

Relative neutralizing activity of the immune serum collected 2 weeks after the 5th immunization (bleeds S5) of rabbits.

| Peptide | Amino acid sequence | Relative HIV neutralizing Activity |
|---|---|---|
| *C17K(CBD1) | CSLEQIWNNMTWMQWDK | ++++ |
| *OVA-C17K | Ovalbumin-CSLEQIWNNMTWMQWDK | ++ |
| *C18K(CBD1) | CKSLEQIWNNMTWMQWDK | ++++ |
| *Biotin-C18K | Biot-KSLEQIWNNMTWMQWDK | − |
| *Strep-Biotin-C18K | Strep-Biot-KSLEQIWNNMTWMQWDK | ++++ |
| *KLH-C17K | KLH-CSLEQIWNNMTWMQWDK | − |

In another series of experiments in rabbits, the immunogenicity of the cysteinyl-CBD1 peptides (C17K, C18K) using various adjuvants: CFA, ALUM, MDP (Muramyl Dipeptide), MDP-Lys(L18), and MF-59 (oil in water emulsion developed by Chiron; see Ott et al 2000 p. 211-228) was investigated. Besides ALUM, all the other adjuvants stimulated efficiently the immune response for the development of specific antibodies against the CBD1 epitope. The best adjuvancy was observed using a mixture of MDP-Lys(L18), and MF-59 (data not shown).

Example 3

The Immunogenicity of the Cysteinyl-CBD1 Peptides in Mice Using Various Adjuvants The purpose of these experiments was to monitor humoral and cellular immune responses to the CBD1 peptide in mice using adjuvants that are compatible in humans, MF-59, CpG oligodeoxynucleotide (ODN) and MDP-Lys. Six animals per group were immunized 4 times at 2 or 3 weeks intervals by intramuscular injection bilaterally into tibialis anterior muscle with 50 μg of the CBD1 peptide formulated in MF-59, [MF-59+CpG ODN], or [MF-59+MDP-Lys]. Groups of 6 mice were injected intramuscularly with the CBD1 peptide (C17K) formulated in either [MF59+MDP-Lys] or [MF59+CpG]. The control animals of each group were injected with the adjuvant preparation alone as negative controls. The different groups of mice were bled via cardiac puncture 10 days after the final injection, and the spleens were removed to perform the ELISPOT assay and cytokines secretion evaluation. Ten days after the fifth immunization, immune serum was tested by ELISA against the CBD1 peptide (C17K). The mean OD value±s.d. corresponds to the mean of the immune sera at 1/8000 dilution of each group. The results are shown in Table 2.

TABLE 2

Anti-CBD1 antibody liter in the sera of mice immunized with the CBD1 peptide

| Five Intramuscular injections | ELISA (OD: 450 nm) |
|---|---|
| CBD1 + [MF59 + MDP-Lys] | 0.42 ± 0.32 |
| CBD1 + [MF59 + CpG] | 1.84 ± 0.75 |

These studies indicated that no significant immune cellular response is initiated in response to immunization with the CBD1 peptide (not shown). However, immunized mice developed CBD1 peptide specific antibodies that were increased following each booster injection. More importantly, these experiments pointed out that CpG ODN is a much more immunopotentiating adjuvant than MDP-Lys. Indeed, mice immunized with the CBD1 peptide adjuvanted with [MF-59+CpG ODN] elicited several fold higher anti-CBD1 antibody titers compared to mice immunized with the CBD1 peptide adjuvanted in [MF59+MDP-Lys] (Table 2).

Example 4

The Immunogenicity of the CBD1 Peptide Adjuvanted with CFA in Guinea Pigs

The immunogenicity of the CBD1 peptide adjuvanted with CFA was investigated in guinea pigs in parallel with the CBD2 peptide, the CBD1/A peptide (in which the three conserved aromatic tryptophan residues are changed to alanine), and the C13K peptide containing the last 12 amino acid residues of the CBD1 peptide (Table 3).

Groups of two guinea pigs were immunized with peptides (75 μg per immunization): CBD1 (C17K), C13K, CBD1/A, or CBD1 coupled to KLH (CBD1-KLH). Ten days after the 5th immunization (bleeds 5), the immune sera were tested by ELISA against CBD1, C13K, CBD1/A and C10M peptides and the CBD1-KLH Construct. The titer of the anti-CBD1 antibody corresponds to the reciprocal dilution of the immune serum giving an OD450 nm value equal to 0.1. The immune sera were assayed for their capacity to inhibit HIV-1 BZ 167 infection of primary CD4⁺ T lymphocytes (Hovanessian et al., 2004; Rey-Cuillé et al., 2006). HIV-1 production was monitored by measuring the concentration of p24 in the culture supernatants of primary CD4⁺ T lymphocytes at 5 days post infection. The percent inhibition of HIV infection occurring at 50-fold dilution of the immune sera is presented in the Table 3.

TABLE 3

The immunogenicity of the CBD1 peptide in Guinea pigs compared to C13K, CBD1/A and CBD1 coupled to KLH. The ELISA titers are presented for the immune sera two weeks after the 5$^{th}$ injection (bleeds S5).

| Peptide Immunogen | ELISA CBD1 | ELISA C13K | ELISA CBD1/A | ELISA KLH | ELISA C10M | Inhibition of HIV-infection |
|---|---|---|---|---|---|---|
| CBD1 (A2) | 128,000 | 128,000 | 16,000 | <200 | 12,000 | 66% |
| CBD1 (F16) | 128,000 | 128,000 | 12,000 | <200 | 12,000 | 57% |
| C13K (H3) | <200 | 400 | <200 | <200 | <200 | No Effect |
| C13K (H4) | <200 | 200 | <200 | <200 | <200 | No Effect |
| CBD1/A (D7) | 20,000 | 2,000 | 128,000 | <200 | 16,000 | No Effect |
| CBD1/A (D8) | 16,000 | 1,000 | 128,000 | <200 | 16,000 | No Effect |
| CBD1-KLH (C1) | <200 | <200 | <200 | <200 | <200 | No Effect |
| CBD1-KLH (C4) | <200 | <200 | <200 | <200 | <200 | No Effect |

CBD1 (C17K): C-S-L-E-Q-I-W-N-N-M-T-W-M-Q-W-D-K
C13K:                   C-I-W-N-N-M-T-W-M-Q-W-D-K
CBD1/A:     C-S-L-E-Q-I-A-N-N-M-T-A-M-Q-A-D-K
C10M:       C-S-L-E-Q-I-W-N-N-M

The capacity of the CBD1 peptide (CSLEQIWNNMTW-MQWDK) to elicit a strong antibody response in various animals indicates that this 17 amino acid peptide should contain an immunodominant B-cell epitope and also overlaps with a major histocompatibility complex class II T cell epitope recognized by CD4⁺ cells (Hovanessian et al., 2004; Rey-Cuillé et al., 2006). Interestingly, the C13K peptide (CI-WNNMTWMQWDK) containing the caveolin-1 binding motif at the last 12 amino acids of the CBD1 peptide is not at all immunogenic in guinea pigs (Table 3), mice and rabbits (data not shown). This loss of immunogenicity suggests that the N-terminal portion of the CBD1 peptide could serve as a T helper epitope.

The immunogenicity of the CBD1 peptide adjuvanted with CFA was investigated in guinea pigs in parallel with the CBD1/A peptide in which the three conserved aromatic tryptophan residues are changed to alanine (Table 3). The CBD1 peptide elicited high-titered antibodies that react equally well with the C13K peptide, thus indicating that the C-terminal portion of the CBD1 peptide containing the three conserved tryptophan residues is an immunodominant B-cell epitope. Besides the C13K peptide, anti-CBD1 immune sera cross-reacted slightly with the CBD1/A peptide, which appears to be due to recognition of the N-terminal 10 amino acid residues of the CBD1 peptide in view of a similar cross-reactivity with the C10M peptide (CSLEQIWNNM). The CBD1/A peptide was also immunogenic in guinea pigs (Table 3) and in rabbits (not presented) as it elicited high titered antibodies against CBD1/A peptide. In contrast to the anti-CBD1 immune sera however, the reactivity of anti-CBD1/A immune sera with the C13K peptide was very poor. The slight cross-reactivity of anti-CBD1/A immune sera with the CBD1 peptide should be due to recognition of the N-terminal portion as illustrated by its reactivity with the C10M peptide. These observations indicate that the N-terminal portion of the CBD1 peptide provides an additional B-cell epitope.

The immunogenicity of peptides is often improved when coupled to a carrier protein. For this purpose, the efficacy of KLH as a carrier protein for the CBD1 peptide using CFA as adjuvant was investigated. However, even after five immunizations at 2-3 weeks interval, the CBD1 peptide coupled to KLH was found not to be immunogenic both in guinea pigs (Table 3) and rabbits (not shown). It was recently reported that because of its structure, the CBD1 peptide has the capacity to penetrate into the cell membrane, interact with interfacial caveolin-1, and be immunogenic (Benferhat et al., 2008). Consequently, the CBD1 peptide when coupled to KLH might loose its structure and immunogenicity. In favor with this, anti-CBD1 antibodies raised against the free CBD1 peptide do not recognize the KLH coupled CBD1 peptide, which was used as an immunogen (Table 3).

Various immune sera raised in guinea pigs (bleeds S5) were tested for their capacity to inhibit HIV-1 BZ 167 infection of human CD4⁺ T lymphocytes. At 50-fold dilution, anti-CBD1 immune serum from the two guinea pigs inhibited HIV infection by 66% and 57%. However, anti-CBD1/A immune sera had no apparent neutralizing activity. This latter points out the importance of the conserved W residues in the caveolin-1 binding motif for the development of HIV-neutralizing antibodies.

Example 5

The Immunogenicity of the CBD1 Peptide and Fine Epitope Mapping of the Immune Sera Raised in Rabbits, Guinea Pigs and in Mice Against the CBD1 Peptide Groups of 2 animals (rabbits, guinea pigs and mice) were immunized with the CBD1 peptide (C17K; 150, 75, and 50 μg/injection in rabbits, guinea pigs and mice, respectively) at 2-3 weeks interval using CFA. Ten days after the 5th immunization, the immune sera were tested by ELISA against the CBD1 peptide. The proportion of IgG1 and IgG2 subclass antibodies in the immune sera of guinea pigs and mice was monitored by specific antibodies. The titer corresponds to the reciprocal dilution of the immune serum giving an $OD_{450nm}$ value equal to 0.1 HIV-1 neutralizing activity (monitored as in Table 1) is expressed as $ID_{50}$ (Inhibitory dilution$_{50}$), which refers to the dilution of the immune serum resulting 50% inhibition of HIV-1 infection.

TABLE 4

The immunogenicity of the CBD1 peptide in rabbits, guinea pigs, and mice.

| Animal | Titer (ELISA) | IgG2/IgG1 ratio | HIV Inhibition ($ID_{50}$) |
|---|---|---|---|
| Rabbit 1 | 768,000 | N.D. | 250 |
| Rabbit 2 | 640,000 | N.D. | 200 |
| Guinea pig 1 | 128,000 | 4.10 | 50 |
| Guinea pig 2 | 96,000 | 3.75 | <50 |
| Mouse 1 | 256,000 | 0.96 | 250 |
| Mouse 2 | 384,000 | 1.15 | 300 |

Figure 8:
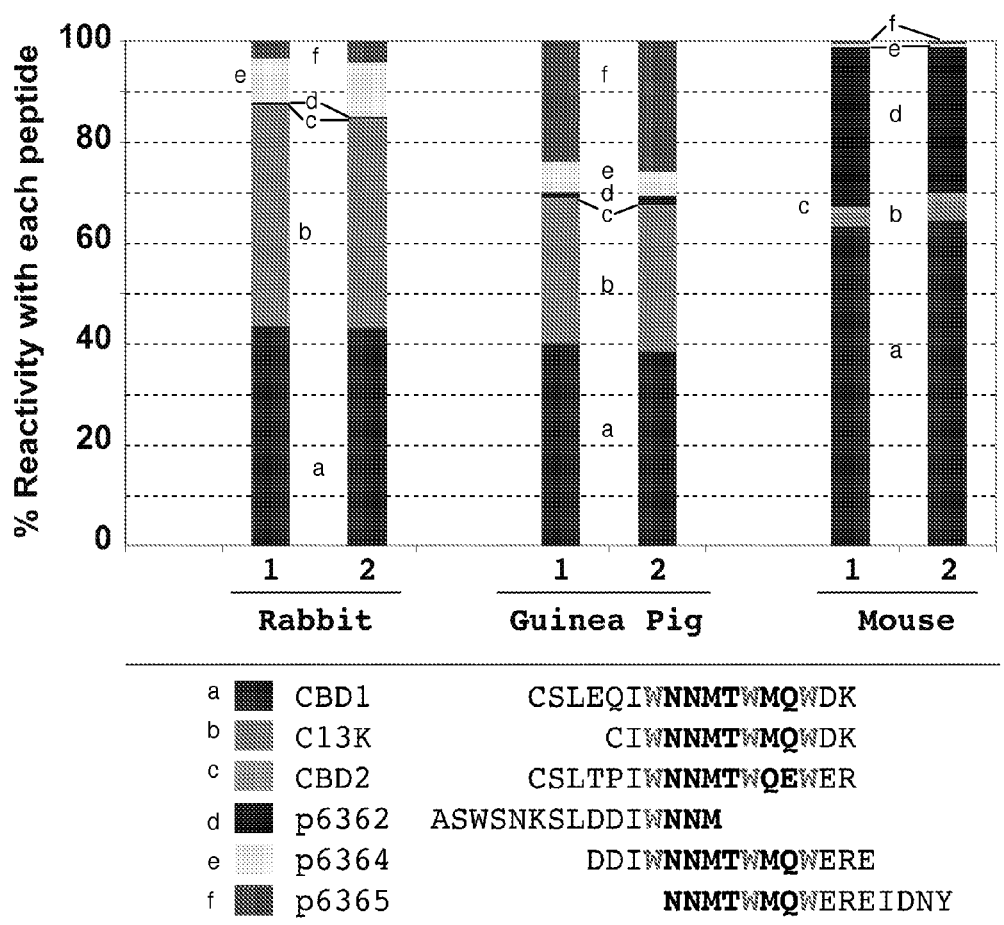
FIG. 8 is a graph showing the fine epitope mapping of immune sera raised in rabbits, guinea pigs and in mice against the CBD1 (C17K) peptide. Groups of 2 animals were immunized with the CBD1 peptides as described in the legends. Ten days after the fifth immunization the immune sera were tested by ELISA against CBD1 (C17K), C13K, CBD2, p6362 (also referred to as p62), p6364 and p6365 peptides. The percent reactivity with each peptide in respect to the reactivity with the CBD1 peptide is given taking into consideration the O.D. values observed at 16,000-fold dilution of the immune sera against the various peptides.

Groups of 2 animals (rabbits, guinea pigs and mice) were immunized with the CBD1 peptide as described above. Ten days after the 5th immunization, the immune sera were tested by ELISA against CBD1, C13K, CBD2, p6362, p6364, and p6365 peptide (shown in FIG. 8) described below. The % reactivity with each peptide in respect to the reactivity with the CBD1 peptide is given by taking into consideration the O.D. values observed at 16,000-fold dilution of the immune sera against the various peptides. The results are shown in FIG. 8.

Under similar immunization conditions using the CBD1 peptide and CFA as adjuvant, HIV-neutralizing activity of anti-CBD1 immune sera from guinea pigs was found to be several-fold lower compared to those from rabbits and mice immunized with the CBD1 peptide (Table 4). For this purpose, fine epitope mapping of anti-CBD1 immune sera was carried out by ELISA using the CBD1, C13K, CBD2, and three overlapping peptides (p6362, p6364, and p6365) containing various segments of the caveolin-1 binding motif, WNNMTWMQW (FIG. 8). Anti-CBD1 immune sera from rabbits and guinea pigs can be distinguished from mice immune sera by a strong cross-reactivity with the C13K peptide that contains the caveolin-1 binding motif, along with a distinct cross-reactivity with the p6364 peptide that contains the caveolin-1 binding motif but within N- and C-terminally modified amino acid residues. On the other hand, anti-CBD1 immune sera from mice can be distinguished from rabbits and guinea pigs by a strong cross-reactivity with the p6362 peptide that contains the N-terminal portion of the motif. Of particular interest is the strong cross-reactivity of anti-CBD1 guinea pig immune sera with the p6365 peptide that contains the C-terminal portion of the motif (FIG. 8), since the guinea pig immune sera consistently manifested reduced HIV-1 neutralizing activity compared to rabbit and mouse anti-CBD1 immune sera (Table 4).

These results demonstrate that there are significant differences in the cross-reactivity profile of anti-CBD1 immune sera from rabbits, guinea pigs, and mice in respect to a given CBD1-based peptide. Such differences probably reflect variations in the intrinsic immune response of these animals to the CBD1 peptide immunogen. For example the processing of the CBD1 peptide might slightly be different in various animals thus generating alternative HLA class II agretopes. Differences were also observed in the IgG subclass distribution of anti-CBD1 reactive antibodies in the immune sera from guinea pigs compared to mice. Indeed, analysis of serum IgG1 and IgG2 levels showed that the IgG2 antibodies are more predominant than IgG1 antibodies in guinea pigs compared to mice, with IgG2/IgG1 ratios from 3.75 to 4.10 and from 0.96 to 1.15 respectively (Table 4).

The cross-reactivity of various anti-CBD1 immune sera with the CBD2 peptide is almost negligible in spite of the fact that CBD1 and CBD2 share a homologous caveolin-1 binding motif. This lack of cross-reactivity of anti-CBD1 immune sera with the CBD2 peptide further confirms the existence of conformational differences between the CBD1 and CBD2 peptide as reported previously (Benferhat et al., 2008; Rey-Cuillé et al., 2006).

Example 6

Inhibition of HIV-1 BZ 162 Infection of Human $CD4^+$ T Lymphocytes

The immune sera of guinea pigs (bleeds S5) were then tested for their capacity to inhibit HIV-1 BZ 162 infection of human $CD4^+$ T lymphocytes. At 100 fold dilution, the immune serum from the guinea pig A2 and F16 immunized with the CBD1 peptide inhibited HIV infection by 66% and 57%, respectively. Although, the CBD1/A peptide was as immunogenic as the CBD1 peptide, immune serum from the guinea pig D7 and D8 immunized with the CBD1/A peptide did not inhibit HIV-1 infection at 100-fold dilution (see Table 3). This latter points out the importance of the conserved W residues in the caveolin-1 binding motif for the development of neutralizing antibodies.

Example 7

The Construction of Chimeric Peptides Containing T Helper Epitope(s) Fused to the CBD1 or CBD1-Based Peptides The fact that the CBD1 peptide, C17K and C18K, by itself is capable of eliciting a strong antibody response in various animals (mice, guinea pigs, rabbits) indicates that it contains a B-cell epitope along with a T cell epitope. On the other hand, the C13K peptide corresponding to the last 12 amino acids is not at all immunogenic in mice, guinea pigs, and rabbits. This loss of immunogenicity in the absence of the N-terminal 5-6 amino acid residues indicates that this portion of the CBD1 peptide serves as a T helper epitope, while the portion containing the conserved CBM serves as a B-cell epitope as set forth in FIG. 3.

In order to enhance the immunogenicity of the CBD1 peptide and make the C13K peptide immunogenic, several constructs with T helper epitopes were generated. For this purpose, three known T helper epitopes fused to the $NH_2$-terminus of the C17K/C18K and the last 12 amino acid residues of the CBD1 peptide, I-W-N-N-M-T-W-M-Q-W-D-K were used.
The three T helper epitopes that were used in this example were:
1) $Tet_{830}$: AQYIKANSKFIGITEL (SEQ ID No: 2). This is the 'promiscuous' T cell epitope from tetanus toxin that associate with a large number of MHC class II molecules (Slingluff et al., 2001).
2) $gp120_{421-436}$: KQIINMWQWGKAMYA (SEQ ID No: 3). This is the fourth constant domain in HIV-1 gp120 that manifests T helper cell epitope function in man, mouse, and macaques (Egan et al., 2004).

3) $Gag_{298-312}$: KRWIILGLNKIVRMY (SEQ ID No: 4). This is the HIV-Gag human DR super motif (located at the CNterminal core protein p24) that binds thirteen human HLA-DR alleles (Wilson et al., 2001).

Co-linear T helper epitope with the CBD1-based peptides were synthesized using a di-lysine (-KK-) linker, which is the target sequence of the lysozomal protease cathepsin B; one of the important proteases for antigen processing in the context of MHC-II antigen presentation (Lennon-Dumenill et al., 2002). Also peptides using the GPGPG spacer were synthesized, which on one hand could prevent the formation of potential junctional epitopes (Livingston et al., 2002) and on the other hand preserve the conformation of the B cell epitope in the chimeric peptide by virtue of glycine and proline residues that promote extended 3-strand formation (Liu et al., 2005).

For the purpose to generate a peptide chimera that could provide a candidate vaccine for the induction of mucosal immunity, the R33K peptide containing the integrin-binding motif RGD (Yano et al., 2005; Yano et al., 2003) fused to the N-terminal end of the A30K peptide chimera composed of the C13K peptide sequence and the tetanus peptide was constructed. The addition of the RGD motif to peptide antigens enhances markedly their immunogenic potential and particularly enables nasal immunization without adjuvants (Yano et al., 2005).

The Sequence of the Various Chimeric Constructs is:

A36K: $Tet_{A830}$ + C18K (linker underlined)
(SEQ ID No: 5)
A-Q-Y-I-K-A-N-S-K-F-I-G-I-T-E-L-<u>K-K</u>-C-K-S-L-E-Q-I-W-N-N-M-T-W-M-Q-W-D-K;

A35K: $Tet_{A830}$ + C17K (linker underlined)
(SEQ ID No: 6)
A-Q-Y-I-K-A-N-S-K-F-I-G-I-T-E-L-<u>K-K</u>-C-S-L-E-Q-I-W-N-N-M-T-W-M-Q-W-D-K;

K36K: $gp120_{421-436}$ + C18K (linker underlined)
(SEQ ID No: 7)
K-Q-I-I-N-M-W-Q-V-V-G-K-A-M-Y-A-<u>K-K</u>-C-K-S-L-E-Q-I-W-N-N-M-T-W-M-Q-W-D-K;

K35K: $Gag_{298-312}$ + C18K (linker underlined)
(SEQ ID No: 8)
K-R-W-I-I-L-G-L-N-K-I-V-R-M-Y-<u>K-K</u>-C-K-S-L-E-Q-I-W-N-N-M-T-W-M-Q-W-D-K;

A30K: $Tet_{A830}$ + I-W-N-N-M-T-W-M-Q-W-D-K (linker underlined)
(SEQ ID No: 9)
A-Q-Y-I-K-A-N-S-K-F-I-G-I-T-E-L-<u>K-K</u>-I-W-N-N-M-T-W-M-Q-W-D-K;

K29K: $Gag_{298-312}$ + I-W-N-N-M-T-W-M-Q-W-D-K (linker underlined)
(SEQ ID No: 34)
K-R-W-I-I-L-G-L-N-K-I-V-R-M-Y-<u>K-K</u>-I-W-N-N-M-T-W-M-Q-W-D-K;

K30K: $gp120_{421-436}$ + I-W-N-N-M-T-W-M-Q-W-D-K (linker underlined)
(SEQ ID No: 11)
K-Q-M-N-M-W-Q-V-V-G-KA-M-Y-A-<u>K-K</u>-I-W-N-N-M-T-W-M-Q-W-D-K;

K27W: $Gag_{298-312}$ + I-W-N-N-M-T-W-M-Q-W (linker underlined)
(SEQ ID No: 12)
K-R-W-I-I-L-G-L-N-K-I-V-R-M-Y-<u>K-K</u>-I-W-N-N-M-T-W-M-Q-W;

K24W: $Gag_{298-312}$ + I-W-N-N-M-T-W (linker underlined)
(SEQ ID No: 35)
K-R-W-I-I-L-G-L-N-K-I-V-R-M-Y-<u>K-K</u>-I-W-N-N-M-T-W;

K27M: $Gag_{293-312}$ + C-S-L-E-Q-I-W-N-N-M (linker underlined)
(SEQ ID No: 14)
K-R-W-I-I-L-G-L-N-K-I-V-R-M-Y-<u>K-K</u>-C-S-L-E-Q-I-W-N-N-M;

K23M: $Gag_{298-312}$ + C-I-W-N-N-M (linker underlined)
(SEQ ID No: 36)
K-R-W-I-I-L-G-L-N-K-I-V-R-M-Y-<u>K-K</u>-I-W-N-N-M;

K30W(G):
$Gag_{298-312}$ + I-W-N-N-M-T-W-M-Q-W (linker underlined)
(SEQ ID No: 16)
K-R-W-I-I-L-G-L-N-K-I-V-R-M-Y-<u>G-P-G-P-G</u>-I-W-N-N-M-T-W-M-Q-W;

K27W(G): $Gag_{298-312}$ + I-W-N-N-M-T-W (linker underlined)
(SEQ ID No: 38)
K-R-W-I-I-L-G-L-N-K-I-V-R-M-Y-<u>G-P-G-P-G</u>-I-W-N-N-M-T-W;

K29R-2: $Gag_{298-312}$ + I-W-D-N-M-T-W-M-E-W-E-R (Consensus 2) (linker underlined)
(SEQ ID No: 18)
K-R-W-I-I-L-G-L-N-K-I-V-R-M-Y-<u>K-K</u>-I-W-D-N-M-T-W-M-E-W-E-R;

K27W-2: $Gag_{298-312}$ + I-W-D-N-M-T-W-M-E-W (Consensus 2) (linker underlined)
(SEQ ID No: 19)
K-R-W-I-I-L-G-L-N-K-I-V-R-M-Y-<u>K-K</u>-I-W-D-N-M-T-W-M-E-W;

R33K: RGD + $Tet_{A830}$ + I-W-N-N-M-T-W-M-Q-W-D-K (mucosal immunity) (linker underlined)
(SEQ ID No: 20)
R-G-D-A-Q-Y-I-K-A-N-S-K-F-I-G-I-T-E-L-<u>K-K</u>-I-W-N-N-M-T-W-M-Q-W-D-K;

R32K: RGD + $Gag_{298-312}$ + I-W-N-N-M-T-W-M-Q-W-D-K (mucosal immunity) (linker underlined)
(SEQ ID No: 21)
R-G-D-K-R-W-I-I-L-G-L-N-K-I-V-R-M-Y-<u>K-K</u>-I-W-N-N-M-T-W-M-Q-W-D-K;

R30W: RGD + $Gag_{298-312}$, + I-W-N-N-M-T-W-M-Q-W (mucosal immunity) (linker underlined)
(SEQ ID No: 22)
R-G-D-K-R-W-I-I-L-G-L-N-K-I-V-R-M-Y-<u>K-K</u>-I-W-N-N-M-T-W-M-Q-W.

All peptides were synthesized using Fmoc chemistry, by NeoMPS SA, Strasbourg.

Example 8

The Immunogenicity and HIV-1 Neutralizing Activity of CBD1, CBD1- and CBM-Based Peptides Fused with a T Helper Epitope The immunogenicity of CBD1, CBD1- and CBM-derived peptides fused with a T helper epitope in mice, and the capacity of the elicited antibodies to inhibit HIV-1 infection was investigated in two sets of experiments.

Example 8A

Figure 4:
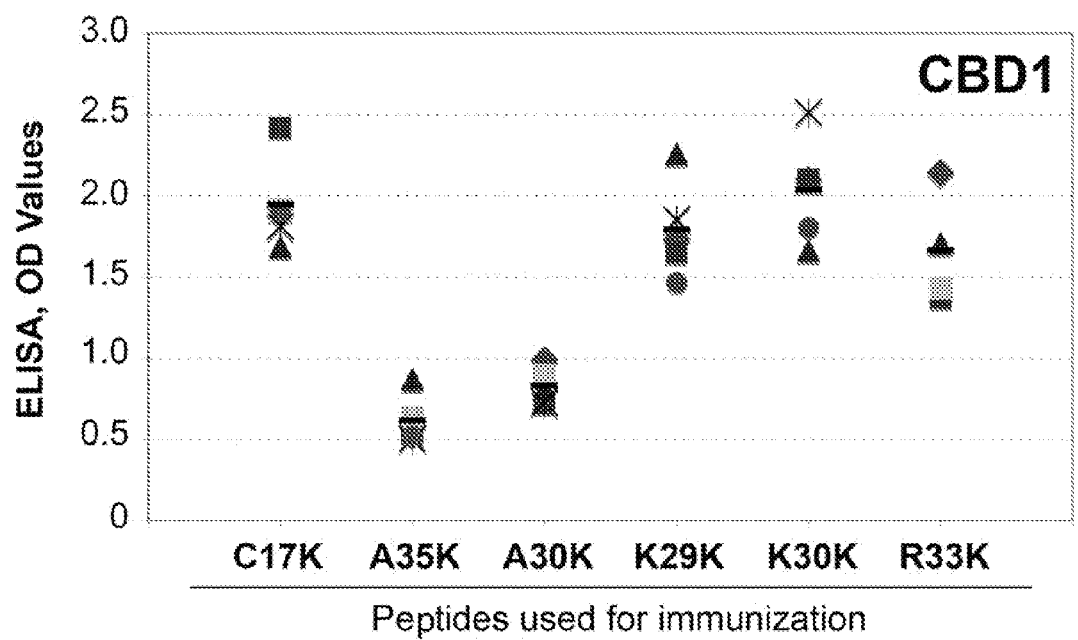
FIG. 4 is a graph showing the results of anti-CBD1 chimeric peptide antibodies in immunized mice using CFA as an adjuvant ten days after the fifth immunization. The immune sera were titrated in ELISA against the CBD1 (C17K) and C13K peptide. The ordinate is the O.D. values observed at a 16,000 fold dilution of the immune sera against the CBD1 (C17K) peptides. The abscissa indicates the groups of mice immunized with the various peptides.
Figure 5:
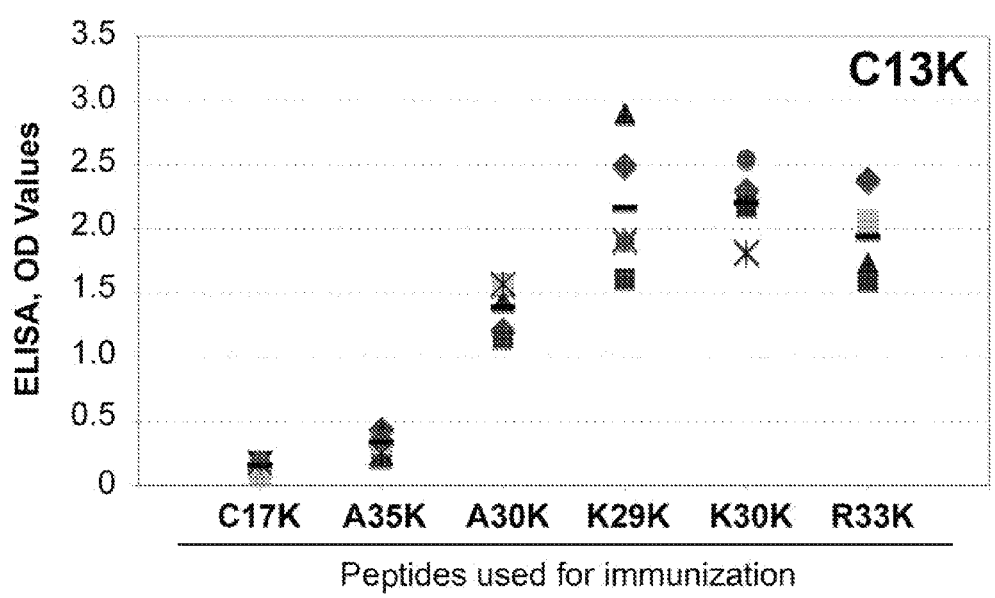
FIG. 5 is a graph showing the results of anti-C13K chimeric peptide antibodies in immunized mice using CFA as an adjuvant ten days after the fifth immunization. The immune sera were titrated in ELISA against the C13K peptides. The ordinate is the O.D. values observed at a 16,000 fold dilution of the immune sera against the C13K peptides. The abscissa indicates the groups of mice immunized with the various peptides.

The first set of experiments using $Tet_{A830}$, $gp120_{421-436}$, and $Gag_{298-312}$ T helper peptides fused to the CBD1 peptide as summarized in Table 5 and FIGS. 4 and 5.

Groups of 6 mice were immunized subcutaneously using Complete Freund's adjuvant with various peptides: 75 µg for C17K, C18K and chimeric peptides of C13K: 150 µg for A36K, A35K, K36K, K35K, A30K, K29K, K30K, and R33K peptides. Ten days after the 5th immunization, the immune sera at 16,000-fold dilution were tested by ELISA against the CBD1 peptide (C17K). The $OD_{450nm}$ values±s.d. correspond to the mean of 6 sera samples in each group. The proportion of IgG1 and IgG2 subclass antibodies was monitored by specific antibodies. The pooled sera from each group were assayed by ELISA against the CBD1 peptide and for their capacity to inhibit HIV-1 BZ 167 infection of primary $CD4^+$ T lymphocytes. HIV-1 production was monitored by measuring the concentration of p24 in the culture supernatants at 5 days post infection as described before (Hovanessian et al., 2004b). The neutralizing activity is expressed as $ID_{50}$ (Inhibitory dilution$_{50}$), which refers to the dilution of the immune serum resulting 50% inhibition of HIV1 infection. The % inhibition of HIV-1 production in the culture medium at 200-fold dilution of respective pooled sera is also presented. The results are shown in Table 5 below.

TABLE 5

The immunogenicity and HIV-1 neutralizing activity of CBD1 and CBD1-based peptides fused with various T helper epitopes.

| Peptide immunogen | ELISA titer against C17K | IgG2/IgG1 ratio | Neutralizing activity $ID_{50}$ | % inhibition of HIV-1 at 200-fold dilution |
|---|---|---|---|---|
| control | 0.02 ± 0.01 | — | None | None |
| C18K | 1.75 ± 0.60 | — | 250-fold | 65% |
| C17K | 1.94 ± 0.45 | 1.08 | 250-fold | 75% |
| A36K | 0.58 ± 0.46 | — | 100-fold | 30% |
| K36K | 1.07 ± 0.33 | — | 150-fold | 45% |
| K35K | 1.72 ± 0.46 | — | 200-fold | 51% |
| A35K | 0.61 ± 0.35 | 1.56 | 150-fold | 42% |
| C13K | 0.03 ± 0.02 | — | None | None |
| A30K | 0.83 ± 0.44 | 3.24 | 150-fold | 45% |
| K29K | 1.80 ± 0.62 | 4.95 | 250-fold | 62% |
| K30K | 2.02 ± 0.41 | 6.66 | 200-fold | 61% |
| R33K | 1.66 ± 0.37 | 4.05 | 200-fold | 64% |

The results show that the presence of these various peptides containing the T helper epitope $Tet_{4830}$, $gp120_{421-426}$ and $Gag_{298-312}$ are still immunogenic and elicit the production of HIV neutralizing antibodies with 50% inhibitory effect on HIV production at immune sera dilutions ranging from 100- to 350-fold (Table 5). The C13K peptide by itself is not immunogenic, however when fused with the T helper epitopes (peptides A30K, K29K, K30K, R33K), it elicits the production of high titer antibodies that react with both the C13K peptide as well as the original CBD1 peptide (see FIGS. 4 and 5). The reactivity of the immune sera with the CBD1 peptide is specific, since they do not react with the CBD2 peptide. It should be noted that the various T helper epitopes were not immunogenic as illustrated by the low and non-specific reactivity of the immune sera with the T helper epitope peptides, $Tet_{4830}$, $gp120_{421-426}$ and $Gag_{298-312}$ (data not shown).

The production of anti-CBD1 peptide antibodies in mice immunized with the A35K peptide (composed of $Tet_{4830}$-KK-CBD1 peptide) was at least 3-fold lower compared to that of the CBD1 peptide alone (Table 5), whereas the difference in the degree of neutralization of HIV-1 infection was less than 2 fold between the two immune sera (Table 5). In general, no strict correlation was apparent between the anti-CBD1 antibody titer and the HIV-1 neutralizing activity, thus pointing out that neutralizing activity corresponds to a small proportion of the total anti-CBD1 antibodies. This latter is most probably due to the fact that the ELISA assay monitors reactivity with a given peptide that might have a specific confirmation, which might be slightly different from the conformation of the CBD1 epitope in the native gp41 molecule.

Anti-CBD1 antibodies raised in rabbits and guinea pigs react strongly with the C13K peptide (Table 3 in reference Rey-Cuillé et al., 2006). However, anti-CBD1 antibodies raised in mice react very poorly with the C13K peptide although they exert a potent anti-HIV inhibitory effect (Table 3, FIGS. 4 and 5). These differences between mice and rabbits/guinea pigs are most probably due to the intrinsic immune response of these animals to the C17K peptide, and the process by which the intrinsic N-terminal T helper epitope in the CBD1 peptide functions in these animals. In accord with this, fine epitope mapping of various immune sera from rabbits, guinea pigs and mice using overlapping peptides revealed significant differences between these animals in respect to a given CBD1 or CBD1-based peptide immunogens (FIG. 8).

Example 8B

Groups of 5 mice were immunized subcutaneously using various chimeric peptides composed of the $Gag_{298-312}$ T helper peptide fused to different size fragments of CBM IWNNMTWMQW for K27W, K24W, K23M, K30W(G) and K27W(G) constructs, whereas for K27W-2 the motif was IWDNMTWMEW corresponding to a secondary consensus sequence. The only exemption was the K27M chimeric peptide composed of the $Gag_{298-312}$ peptide linked with the C10M peptide (C-S-L-E-Q-I-W-N-N-M), which corresponds to the first 9 amino acid residues of the CBD1 peptide (C17K). The peptides for this example are shown in Table 6 below.

TABLE 6

| Peptide | Sequence | SEQ ID |
|---|---|---|
| K27W | K-R-W-I-I-L-G-L-N-K-I-V-R-M-Y-K-K-I-W-N-N-M-T-W-M-Q-W | 12 |
| K24W | K-R-W-I-I-L-G-L-N-K-I-V-R-M-Y-K-K-I-W-N-N-M-T-W | 35 |
| K23M | K-R-W-I-I-L-G-L-N-K-I-V-R-M-Y-K-K-I-W-N-N-M | 36 |
| K27W-2 | K-R-W-I-I-L-G-L-N-K-I-V-R-M-Y-K-K-I-W-D-N-M-T-W-M-E-W | 19 |
| K30W(G) | K-R-W-I-I-L-G-L-N-K-I-V-R-M-Y-G-P-G-P-G-I-W-N-N-M-T-W-M-Q-W | 16 |
| K27W(G) | K-R-W-I-I-L-G-L-N-K-I-V-R-M-Y-G-P-G-P-G-I-W-N-N-M-T-W | 38 |
| K27M | K-R-W-I-I-L-G-L-N-K-I-V-R-M-Y-K-K-C-S-L-E-Q-I-W-N-N-M | 14 |
| C10M | C-S-L-E-Q-I-W-N-N-M | 32 |
| C17K | C-S-L-E-Q-I-W-N-N-M-T-W-M-Q-W-D-K | 31 |

Two weeks after the 4th immunization, the immune sera were tested by ELISA against the respective peptides and assayed for their capacity to inhibit HIV-1 BZ 167 infection of primary $CD4^+$ T lymphocytes (Table 6, Table 7). The immune sera from the immunized mice are described in Table 6. Bleeds S4 were titrated by ELISA against various peptides. The $OD_{450\ nm}$ values±s.d. correspond to the mean of 5 sera samples in each group at 6,000-fold dilution. The reactivity of the immune sera raised against the K27W peptide is higher with the homologous K30W(G) peptide; the only difference between the two peptides is the linker. The anti-K27W immune sera react strongly with its respective immunogen (with the K-K linker) and its homologous K30W(G) peptide with the G-P-G-P-G linker. Similarly, the anti-K24W immune sera react strongly with its respective immunogen (with the K-K linker) and its homologous K27W(G) peptide with the G-P-G-P-G linker.

The K23M peptide was found to be a poor immunogen, since only 1 out of the five immunized mice developed peptide specific antibodies. All other peptides were highly immunogenic as illustrated by the production of peptide-immunogen specific antibodies (Table 7).

Peptide chimeras K27W and K24W are homologous to K30W(G) and K27W(G), respectively. The difference between them is simply the peptide linker K-K or G-P-G-P-G. The sequence W-N-N-M-T-W-M-Q-W and I-W-N-N-M-T-W appears to be better presented in the chimera with the G-P-G-P-G linker compared to the K-K linker. Accordingly, the reactivity of anti-K27W and -K24W immune sera with the G-P-G-P-G linked K30W(G) and K27W(G) peptides is consistently higher, respectively, compared to that of K27W and K24W peptide. On the other hand, the anti-K30W(G) and K27W(G) do no react with the homologous K27W and K24W peptide, thus revealing important conformational differences raised by the K-K and G-P-G-P-G linker (Table 7). Besides to their homologous G-P-G-P-G linked K30W(G) and K27W(G) peptides, K27W and K24W cross-reacted with the other peptides, including with the K27W-2 peptide that contains the secondary consensus caveolin-1 binding motif, W-D-N-M-T-W-M-E-W, in which the N and Q are changed into D and E respectively. This latter is consistent with the reactivity of such antibodies with a conformational epitope.

(Table 8). HIV-1 production was monitored by measuring the concentration of p24 in the culture supernatants at 5 days post infection as described before (Hovanessian et al., 2004b). The neutralizing activity is expressed as $ID_{50}$ (Inhibitory dilution$_{50}$), which refers to the dilution of the immune serum resulting 50% inhibition of HIV1 infection. The % inhibition of HIV-1 production in the culture medium at 200-fold dilution of respective pooled sera is also presented. The mix represents pooled serum from mice immunized with C17K/K27W/K30W(G)/K24W (1/1/1/1) designated by the asterisk.

TABLE 8

The immunogenicity and HIV-1 neutralizing activity of CBD1 and CBM-derived peptide chimeras.

| Peptide | ELISA against the Immunogen (OD) | Neutralizing activity ID50 Fold-Dilution | % Inhibition of HIV-1 infection at 200-fold dilution |
|---|---|---|---|
| C17K* | 1.22 | 300-fold | 59% |
| C10M | <0.10 | No Effect | No Effect |
| K27M | 1.38 | 250-fold | 65% |
| K27W* | 1.64 | 300-fold | 65% |
| K24W* | 1.55 | 450-fold | 88% |
| K23M[a] | 0.66 | 100-fold | 11% |
| K27W-2 | 2.01 | 100-fold | <10% |
| K30W(G)* | 1.45 | 450-fold | 81% |
| K27W(G) | 0.73 | 100-fold | 16% |
| *Mix: C17K/K27W/K30W(G)/K24W | | >800-fold | >98% |

[a]Only 1 out of five mice immunized with the K23M peptide developed anti-K23M specific antibodies.

The C10M peptide was not immunogenic. However, when coupled to the Gag T helper epitope, K27M, then high titer antibodies were generated in the immunized mice. Anti-K27M antibodies reacted strongly with the C10M peptide

TABLE 7

The cross reactivity of immune sera raised in mice against the CBM-based peptide chimeras: K27W, K24W, K23M, K30W(G), K27W(G), K27M and the CBD1 peptide (C17K).

| Immunogen | ELISA K27W | ELISA K24W | ELISA K23M | ELISA K27W(G) | ELISA K30W(G) | ELISA C17K | ELISA K27M | ELISA p6362 |
|---|---|---|---|---|---|---|---|---|
| K27W | 1.49 ± 0.75 (4.55)* | <0.20 | <0.20 | <0.20 | 2.25 ± 0.20 | 0.24 ± 0.12 | <0.20 | <0.20 |
| K24W | 0.21 ± 0.15 | 1.41 ± 0.55 (4.88)* | 0.45 ± 0.40 | 1.88 ± 0.66 | <0.20 | <0.20 | 0.87 ± 0.15 | <0.20 |
| K23M | <0.20 | <0.20 | 0.53 (4.00)* | <0.20 | <0.20 | <0.20 | <0.20 | <0.20 |
| K27W(G) | <0.20 | <0.20 | <0.20 | 0.66 ± 0.22 (4.26)* | <0.20 | <0.20 | <0.20 | <0.20 |
| K30W(G) | <0.20 | <0.20 | <0.20 | <0.20 | 1.23 ± 0.55 (3.54)* | <0.20 | <0.20 | <0.20 |
| C17K | <0.20 | <0.20 | <0.20 | <0.20 | <0.20 | 1.94 ± 0.28 (0.88)* | 2.91 ± 0.26 | 1.78 ± 0.22 |
| K27W-2 | 0.22 ± 0.08 | <0.02 | <0.02 | 2.01 ± 0.73 | <0.20 | <0.20 | <0.20 | <0.20 |

Groups of 5 mice were immunized subcutaneously using Complete Freund's adjuvant with various peptides: 75 µg for C17K; 150 µg for K27W, K27W-2, K30W(G), K24W, K27W (G), K27M and K23M. For the C10M group, the immunogen mix was 75 µg of the C10M peptide (C-S-L-E-Q-I-W-N-N-M) with 75 µg of the $Gag_{298-312}$ peptide (K-R-W-I-I-L-G-N-K-I-V-R-M-Y). Two weeks after the $5^{th}$ immunization, the immune sera were tested by ELISA against the respective peptide. The $OD_{450nm}$ values correspond to the mean of 5 sera samples in each group at 6,000-fold dilution. The pooled sera from each group were assayed for their capacity to inhibit HIV-1 BZ 167 infection of primary $CD4^+$ T lymphocytes (not shown). Immune sera raised against K27W-2, K30(G), K27W(G) and C17K did not cross react significantly with other peptides thus revealing the existence of multi-determinants within the 10 amino acid residues of the CBM. The smallest sequence that was highly immunogenic is the I-W-N-N-M-T-W sequence as presented by the K24W chimera (Table 6).

Most of the immune sera manifested HIV-1 neutralizing activity with 50% inhibitory effect on HIV production at immune sera dilutions ranging from 100- to 450-fold (Table 8). The highest ID50 values were observed for the K24W and K27W-2, followed by K27W and C17K. Interestingly, the mixture of immune sera from mice immunized with K27W, K24W, K30W(G) and C17K (1/1/1/1; designated by the asterisk) resulted in a synergistic neutralizing activity against HIV-1 infection with an ID50 value >800-fold dilution of the pooled sera, At 200-fold dilution of the pooled sera, the inhibitory effect on HIV-1 infection was >98%.

Figure 16:
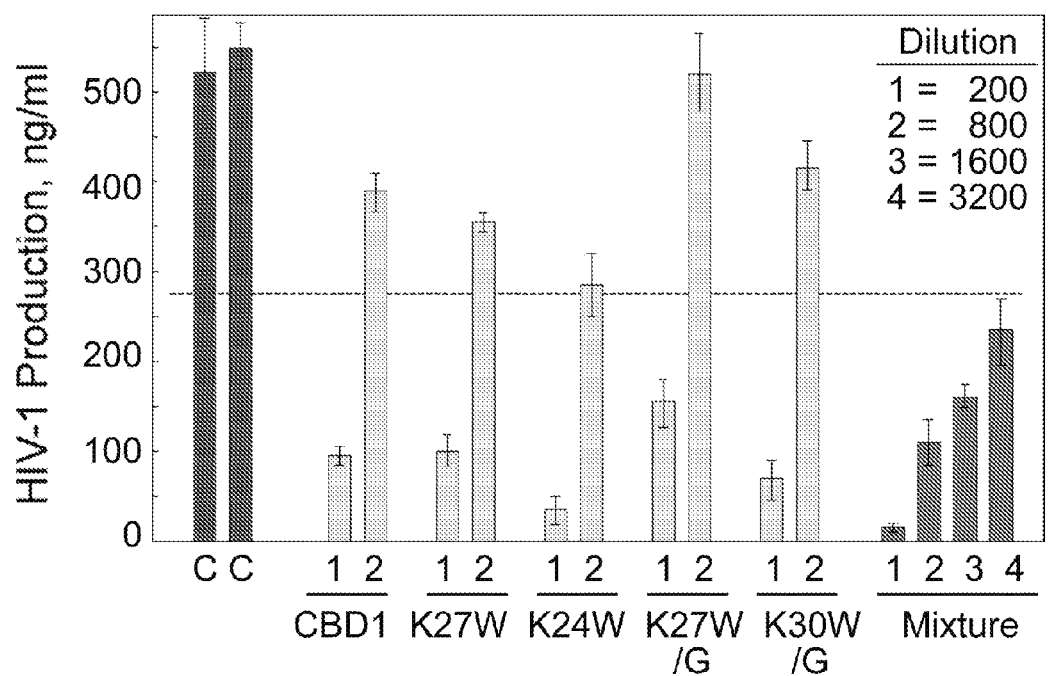
FIG. 16 is a graph showing the inhibition of HIV-1 infection by the immune sera raised against the CBD1 (C17K) peptide and CBD1-based peptides. Immune sera (bleeds 5) from individual mouse immunized with various peptides (CBD1 (C17K), K27W, K24W, K27W(G), K30W(G); abscissa) as described in the legend of Table 4 were tested for their capacity to inhibit HIV-1 infection. HIV-1 BZ 167 was incubated at 200- and 800-fold dilutions of each immune serum (histograms 1 and 2, respectively) for 45 minutes at 37° C. before infection of primary $CD4^+$ T lymphocytes. Histograms C stand for control infections in which two pre-immune sera were used at a 200-fold dilution. The mixture represents pooled sera from mouse immunized with either CBD1 (C17K), K27W, K24W, K27W(G), and K30W(G) peptide at 1/1/1/1/1 ratio. The mixture of immune sera was tested at 200-, 800-, 1600-, and 3200-fold dilution (histograms 1, 2, 3, and 4 respectively). The dash-line represents 50% inhibition of HIV-1 infection.

Similar experiments were performed using individual immune sera from each group of mice immunized with the CBD1, K27W, K24W, K27W(G) and K30W(G) peptide. The results of a typical experiment is presented in FIG. 16 showing that the $ID_{50}$ inhibitory effect of various immune sera is increased by at least 4-fold by the mixture of five immune sera raised against different peptides. At 200- and 800-fold dilution of individual immune sera the inhibitory effect on HIV-1 infection is 70-90% and less than 50%, respectively, whereas the $ID_{50}$ value for the mixture of such sera is observed at a dilution less than 3200-fold (FIG. 16).

Figure 17:
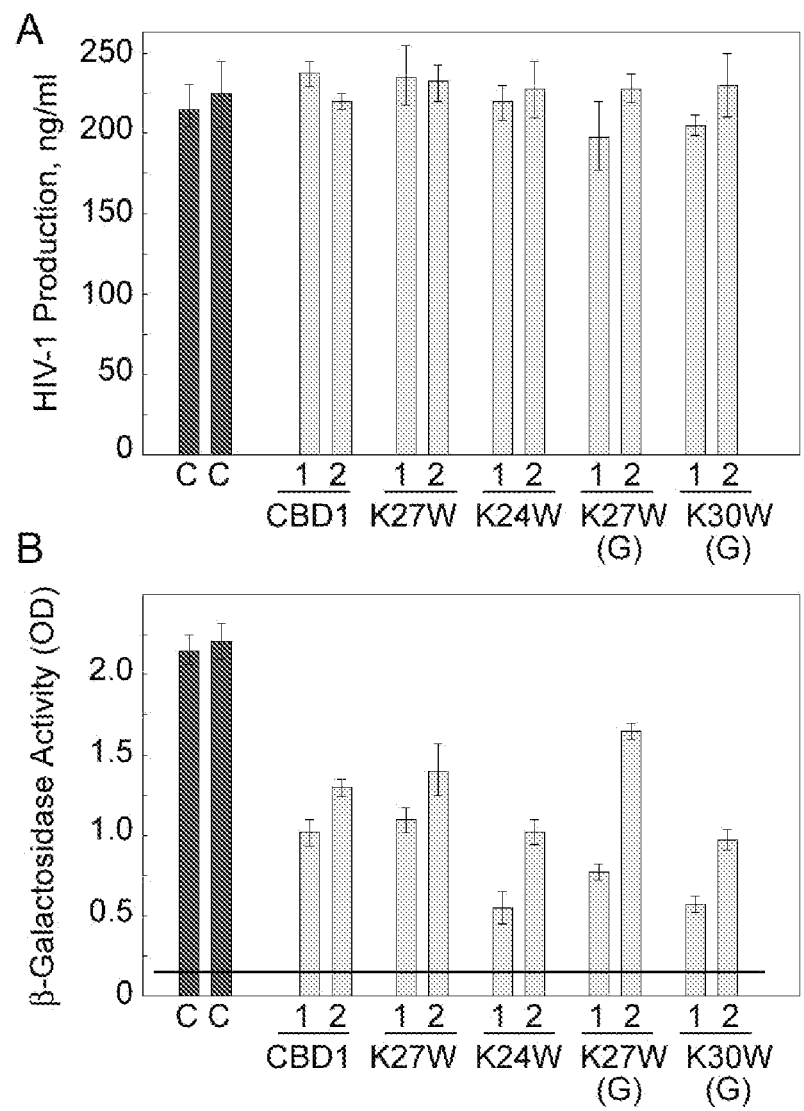
FIG. 17 is a graph showing the production of virus particles with reduced infectivity in HIV-1 infected cultures treated with mice immune sera raised against CBD1 (C17K) or CBM-based peptides. (A) HIV-1 production measured by the concentration of p24 in culture supernatants. $CD4^+$ T lymphocytes were infected with HIV-1 BZ 167, and after 2 days they were treated with immune sera (bleeds S5) from individual mouse immunized with various peptides: CBD1 (C17K), K27W, K24W, K27W(G), K30W(G) (at 200- and 800-fold dilution as shown in histograms 1 and 2, respectively). At 5 days post-infection, production of HIV-1 was monitored by measuring the concentration of virion p24 (ng/ml, ordinate). (B) HIV-1 particles produced in the presence of immune sera are less infectious. Culture supernatants from infected $CD4^+$ T lymphocytes were recovered from the cultures at 5 days post-infection (as described in section A), diluted 10-fold and tested for virion infectivity in a single-round infectivity assay by using HeLa P4C5 cells. The line in the figure over the histograms shows the background levels occurring in the absence of virus infection. The mean of ±SD of triplicate samples is sh which a pre-immune serum was used at a 100-fold dilution. Cocktail A and cocktail B pooled-serum dilution that gave 50% inhibition ($ID_{50}$) of HIV-1 BZ167 infection was estimated to be a 300- and 400-fold dilution, respectively. Infection of $CD4^+$ T lymphocytes derived from human peripheral mononuclear cells (PBMC) was as described in 2.3 of the paragraph "methods."

The addition of anti-CBD1 antibodies in HIV-1 producing cultures of T lymphocytes causes the production of defective virus particles, since anti-CBD1 antibodies cause aggregation of gp41 in the plasma membrane resulting in the production of virus particles deficient in the gp120-gp41 complex. Consequently, such virus particles are less infectious (Hovanessian et al., 2004). FIG. 17 demonstrates that this is also the case with antibodies raised against the CBM-derived chimeric peptides. For this purpose, the action of immune sera on HIV-1 production was tested when added 2 days after virus infection of $CD4^+$ T lymphocytes. Under these experimental conditions, there is no apparent effect on virus production monitored by the HIV-1 major core protein p24 at 5 days post-infection (FIG. 17A). Culture supernatants of such infected cells were diluted 10-fold and tested for virion infectivity in a single-round infectivity assay by using HeLa P4C5 cells (FIG. 17B). The results show that HIV-1 particles produced in the presence of the immune sera at 200-fold dilution, are at least 50% less infectious compared to the corresponding virions recovered from cultures treated with preimmune sera.

In addition to the inhibition of virus infection therefore, mice immune sera raised against various CBM-based chimeric peptides have the capacity to act on HIV-1 producing cells leading to the production of virus particles with reduced infectivity.

The Significance of these Results:

The observation that anti-CBM antibodies could cause the production of deficient virus particles when added in HIV-1 producing cell cultures (FIG. 17), points out that such antibodies directed against distinct neutralizing determinants can also react with gp41 expressed on the surface of HIV-1 producing cells. Consequently, such antibodies might trigger elimination of HIV-infected cells in vivo by Fc-mediated effector systems, such as antibody-dependent cellular and complement-mediated cytotoxicity (Parren and Burton, 2001). On the other hand, defective HIV particles could be engaged by the host immune system for the generation of humoral and cellular immune responses against viral proteins, as it has been reported recently in response to HIV pseudovirion particles (Chen et al., 2005).

The conclusions that can be drawn from the above experiments are the following. Peptide vaccines able to induce high affinity and protective neutralizing antibodies must rely in part on the design of antigenic epitopes that mimic the three-dimensional structure of the corresponding region in the native protein. Here, it was shown that the CBD1 peptide and the CBD1-derived peptides as such or fused with T helper epitopes generates conformational epitopes that have the capacity to induce antibodies capable of neutralizing HIV-1 infection. The CBM-derived peptides are immunogenic only after fusion with a T helper epitope.

By its capacity to bind caveolin-1 in the plasma membrane, the CBD1 peptide can be taken up by the endosome pathway and processed by proteolytic enzymes into distinct overlapping fragments (or determinants) that interact with HLA class II molecules during their transport to the plasma membrane of antigen-presenting cells. Such processed peptides could then be identified by T-cell receptors present on the plasma membrane of $CD4^+$ T helper cells. This latter could account for the generation of overlapping determinants.

The lack of cross reactivity of various immune sera while they exert neutralizing activity against HIV-1 infection (Tables 6 and 7), and the isolation of neutralizing monoclonal antibodies that do not cross-react with distinct CBD1- and CBM-based peptides (Table 10), it is plausible to suggest that the CBD1 epitope has several related conformations, which are mimicked by specific CBD1- and CBM-based peptides. Consequently, such peptides could induce antibodies that are directed towards a specific conformation of the CBM.

The synergism in HIV-neutralization observed by the mixture of the immune sera reacting with specific determinants suggests that a cocktail of CBD1- and CBM-derived peptides with various T helper peptides should be considered for a candidate vaccine preparation in order to obtain an efficient humoral immune response against the CBD1 epitope.

Example 9

The CBD1 Peptide Elicits Neutralizing Antibodies in Rhesus Macaques

Adult male cynomolgus macaques (*Macaca fascicularis*) weighing 4-6 kg, imported from the Mauritius breeding colony, were maintained and handled in accordance with European guidelines for non-human primate care (EEC Directive N 86-609, 24 Nov. 1986). The animals were sedated with ketamine chlorhydrate (10-15 mg/kg) for immunizations and blood sample collections. In the first set of immunizations, animals were immunized with the cysteinyl CBD1 peptide (200 μg) via the intradermal (I.D.) or intramuscular (I.M.) route using as adjuvant [MF59+MDP-Lys(L18)]. The control macaques were injected with the adjuvant alone. In this example, CBD1 refers to the C18K peptide CKSLEQIWNNMTWMQWDK, as defined in SEQ ID NO:42.

In the second set of immunization, animals were immunized subcutaneously with Tet-KK-CBD1 (400 μg) or with CBD1+$Tet_{A830}$ peptide (200 μg+150 μg) using as adjuvant the mixture composed of [CpG+Montanide ISA 51]. For each immunization, 500 μl consisting of one volume of immunogen with one volume of adjuvant mixture were administered. In general, animals were bled 15 days after each immunization in order to monitor the immune response.

The immune sera were titrated by ELISA using 96 well plates (Maxisorp, Dynatech) coated with 2 μM of the various peptides (as indicated) and incubated for 60 min at 37° C. The immune sera were added in serial dilutions and incubated for 60 min at 37° C. After washing, sheep anti-human IgG conjugated with horseradish peroxidase (GE Healthcare, UK Limited) was added. (It should be noted that the detection of monkey IgG with anti-monkey antibodies give higher background levels compared to anti-human antibodies.) Following incubation and washing, o-Phenylenediamine dihydrochloride (OPD) substrate was added to the wells as described (Hovanessian et al., 2004; Rey-Cuillé et al., 2006). Following color development the reaction was quantitated at 450 nm.

The antibody titers correspond to the reciprocal dilution of the respective rabbit serum giving an OD value equal to 0.1 (measured at 450 nm).

The Immunogenicity of the CBD1 Peptide in Macaques

A total of eight animals were used in this study. Two groups of three animals were injected via intramuscular or intradermal route with the CBD1 peptide (200 µg) formulated in [MDP-Lys+MF-59] adjuvant at week 0, 4, 8, 12 and 16. As control, two macaques were injected either intramuscularly or intradermally with the adjuvant formulation alone. Sera and PBMC were collected at week 0, 2, 4, 6, 8, 10, 12, 14, 16, 18, 20 and 22, to test the titer of antibodies by ELISA, and also to monitor cellular immune response by performing IFN-γ ELISpot specific for the CBD1 peptide.

Figure 10:
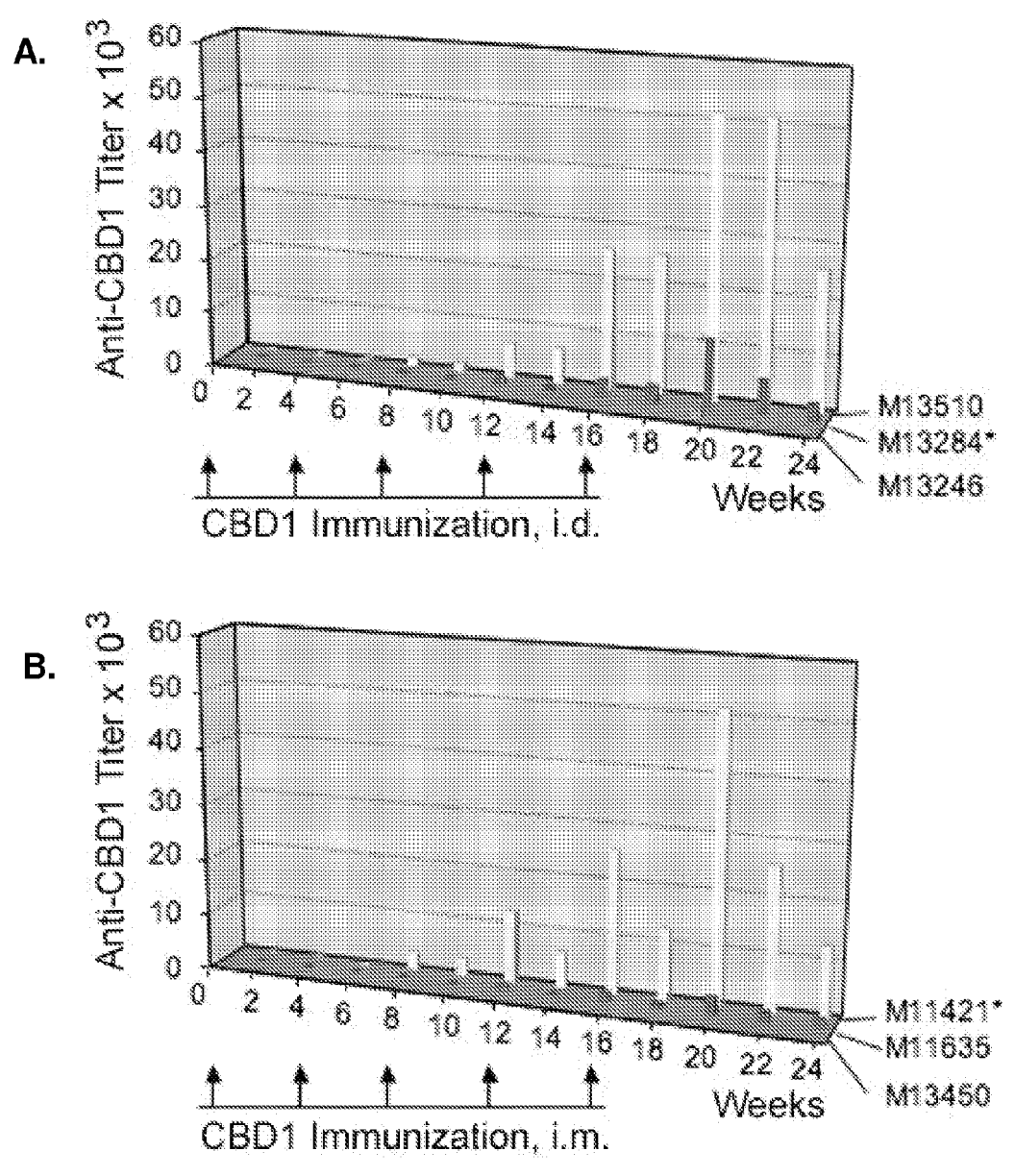

No significant level of anti-CBD1 humoral response was generated in the immunized animals until the third immunization with the CBD1 peptide (FIG. 10 A, 10 B). After five immunizations, two out of the three intradermally injected macaques developed high antibody titers (macaques M13510 and M13284), compared to one out of the three intramuscularly injected animals (macaque M11421). It might therefore be possible that the intradermal injection is a more efficient route of injection compared to the intramuscular one. In each group there were poor responders among the immunized animals: macaque M13246 in the intradermally injected group developed a weak humoral response, while macaque M11635 and M11450 in the intramuscularly injected group developed a weak and no response, respectively. This weak or lack of immune responses in animals suggested that there should be MHC restriction in primates for the development of an optimal humoral response against the CBD1 peptide immunogen. Indeed, CBD1 peptide may not be able to be bind by all the MHC molecules of the macaque population used in this experiment. The deficiency in CBD1 peptide presentation to T cells may reflect the absence of an efficient T helper response.

Figure 9:
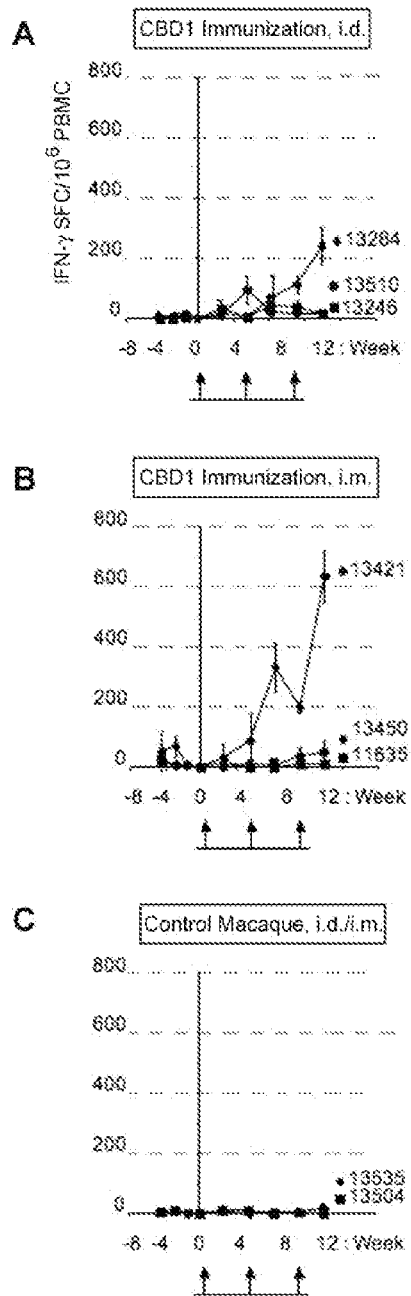
FIGS. 9A, 9B and 9C are graphs showing the cellular immune against the CBD1 peptide in macaques immunized either intradermally (i.d.) or intramuscularly (i.m.). Macaques were immunized with the CBD1 (C18K) peptide using [MF59+MDP-Lys(L18)] as described in Example 9. The responses were obtained by stimulating the PBMC, sampled at the indicated week (abscissa), with CBD1 (C18K) peptide in IFN-γ ELISpot assays. The results are expressed as the number of spot forming cells (SFC) per million of PBMC from the animals included in the study. 13504 and 13535 are control animals injected with the adjuvant [MF59+MDP-Lys (L18)] alone (without peptide) by the i.d. and i.m. route, respectively. Vertical arrows indicate the weeks of vaccination.
Figure 11:
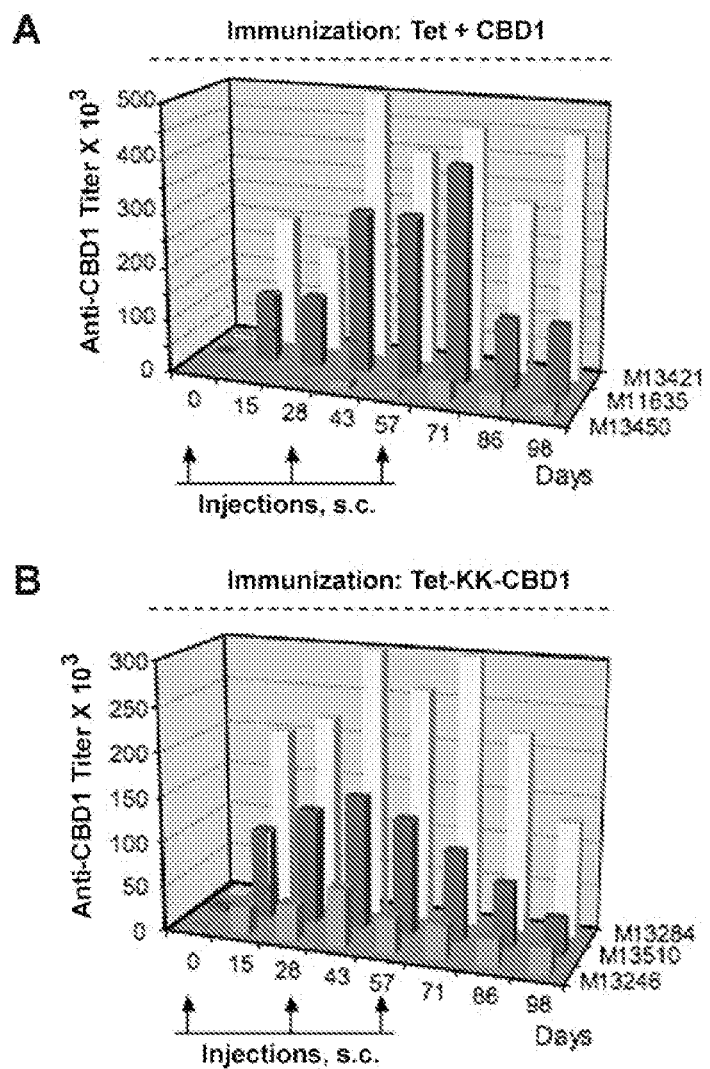

Concerning the cellular immune response against the CBD1 peptide, only one out of the three immunized animals in each group developed a significant level of T-cell response against the CBD1 epitope (FIG. 9). This latter was observed after the third immunization in the intradermally immunized macaque M13284, and after the second immunization in the intramuscularly immunized macaque M13421. Although the development of the T-cell response was correlated with the production of anti-CBD1 antibodies in these two animals, macaque M13510 that produced high antibody titer manifested no significant T cell response. After the fourth immunization, all the immunized animals developed a non-specific T cell response that might be mediated by the adjuvant mix, since a similar non-specific T cell response was generated also in the control macaques (M13535 and M13504) injected with the adjuvant mix alone (not shown). The mechanism by which [MDP-Lys(L18)+MF-59] adjuvant causes development of a non-specific T cell response remains to be investigated. On the other hand, it should be noted that the humoral response developed in these same macaques was specific to the CBD1 immunogen all along the 24 weeks study period (FIG. 10). Indeed, macaque immune sera that reacted with the CBD1 peptide did not cross-react with the homologous CBD2 peptide (CSLTPIWNNMTWQEWER), corresponding to the potential caveolin-1 binding domain in the trans-membrane envelope glycoprotein of HIV-2 (data not shown).

The Immunogenicity of the CBD1 Peptide in Association with a Promiscuous T Helper Epitope from Tetanus Toxin In order to overcome the potential MHC-restriction against the CBD1 peptide in macaques, the 'promiscuous' T cell epitope from the tetanus toxin ($Tet_{4830}$; AQYIKANSKFIGI-TEL), which associates with a large number of MHC class II molecules was used (Jackson et al., 2002). The Tet-KK-CBD1 co-linear chimera composed of the $Tet_{4830}$, the helper epitope, fused with the CBD1 peptide via the dilysine linker (KK), which is the target sequence of the lysosomal protease cathepsin B involved in antigen processing in the context of MHC-II antigen presentation was constructed (Lennon-Duménill et al., 2002; Yano et al., 2005). The dilysine motif can also be responsible for retention in the endoplasmic reticulum and prolonged half-life of an immunogen (Steinhilb et al., 2002).

In several immunization experiments, it was first shown that the Tet-KK-CBD1 chimera is immunogenic by eliciting the production of anti-CBD1 antibodies in mice, guinea pigs and rabbits (not shown). The effect of the Tet T helper epitope on the immunogenicity of the CBD1 peptide in the two groups of macaques that were previously immunized with the CBD1 peptide alone was tested. This second set of immunization started four months after the fifth injection of macaques described in the first study. Interestingly, significant levels of anti-CBD1 antibodies were still present after four months in those macaques that were considered as responders (Table 9). This persistence of anti-CBD1 antibodies suggests that immunization with the CBD1 peptide could elicit a B cell memory response.

The two groups of macaques were immunized subcutaneously with the CBD1 peptide in association with tetanus T helper epitope peptide, either fused (Tet-KK-CBD1) or free (CBD1+Tet) peptides using as adjuvant the mixture [CpG+Montanide ISA 51]. The choice of CpG and Montanide was based on their efficacy as adjuvants and clinical safety in variety of phase II and phase III human vaccination trials (Kleinman et al., 1991; Kreig, 2007; Peek et al., 2008). Macaques were immunized three times at day 0, 28, and 57, and sera were collected at day 0, 15, 28, 43, 57, 71, 86 and 98 in order to titrate by ELISA against the CBD1 and the Tet peptide (Table 9, FIG. 11). Administration of the Tet T helper epitope with the CBD1 peptide, either free or fused, enhanced markedly the anti-CBD1 antibody response among all macaques as soon as 15 days after the first immunization and seemed to reach a plateau after the second immunization. Strikingly, the weak and non-responder macaques in the first set of immunization study, macaques M13246, M11635 and M11450, generated a very strong CBD1 specific humoral response in the presence of the T helper peptide.

In contrast to the CBD1 peptide, only one out of three immunized macaques in each group developed high levels of anti-Tet peptide antibodies (Table 9). Moreover, there was no direct correlation in the antibody titer against the Tet and CBD1 peptide in a given immune sera. For example, macaques M13246, M11635 and M13450 that developed a strong response against the CBD1 peptide, generated rather low or no humoral response against the Tet peptide The HIV Neutralizing Activity of Macaque Immune Sera The capacity of macaque immune sera to inhibit infection of primary $CD4^+$ T lymphocytes by a primary HIV-1 isolate was tested. Consistently, we observed that HIV-1 infection in such cultures is enhanced by 30-50% in the presence of dilutions of control macaque sera <200-fold, either pre-immune or from macaques injected with adjuvant alone. This enhancing effect on virus production might be due to the stimulatory effect of macaque sera on the proliferation of the primary human T lymphocytes cells in culture. For this reason, the inhibitory effect of macaque immune sera on HIV infection was assayed at 200- and 400-fold dilution.

Figure 12:
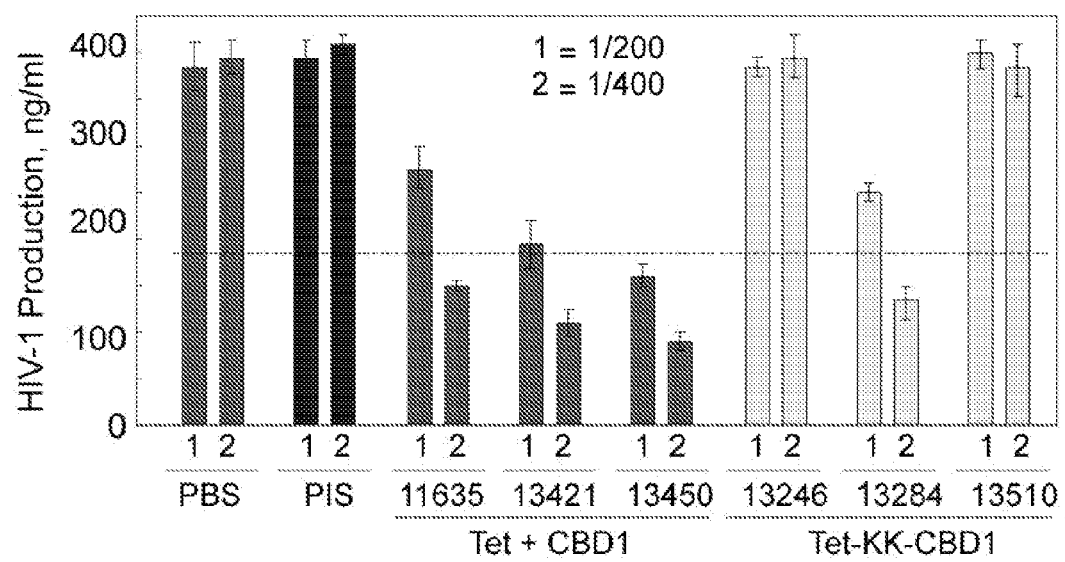
FIG. 12 is a graph showing the neutralization of HIV-1 infection by the macaque immune sera. The immune sera (bleeds at day 86) from macaques immunized with free CBD1 (C18K) and Tet peptide [Tet+CBD1] or the covalently linked Tet-KK-CBD1(C18K) peptide were tested for their capacity to inhibit HIV-1 infection of primary $CD4^+$ T lymphocytes at 200- and 400-fold dilution (histograms 1 and 2, respectively). The ordinate gives the production of HIV-1 (ng/ml) monitored by measuring the concentration of the major viral core protein p24 by ELISA at 5 days post-infection. PIS stands for pre-immune serum of macaque 13450. PBS stands for the control infection in which phosphate buffered saline was added instead of diluted serum. The dash-line represents 50% inhibition of HIV-1 production.
Figure 13:
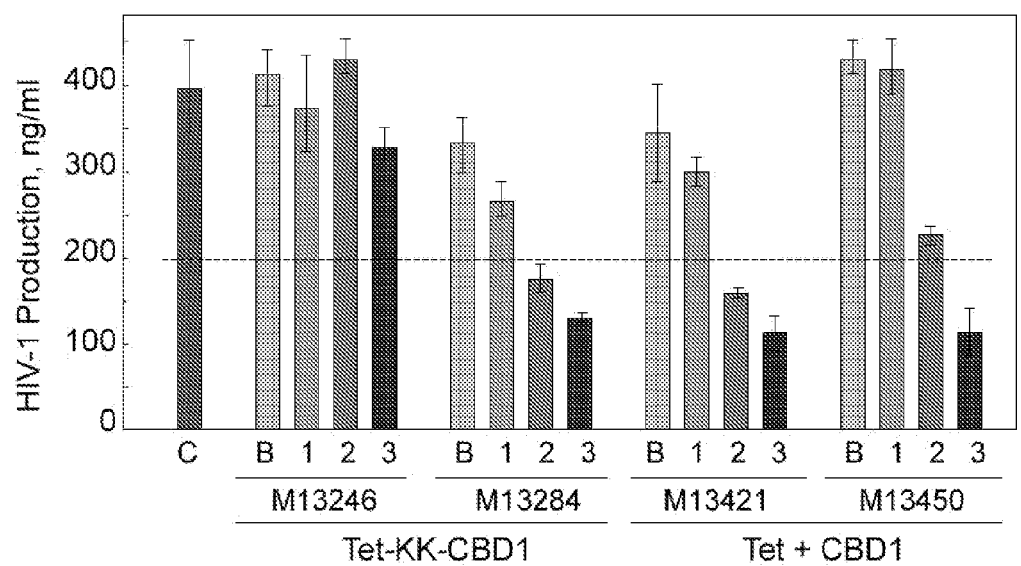
FIG. 13 is a graph showing anti-HIV activity of successive bleeds from macaques after immunization with the free CBD1 (C18K) and Tet peptide or fused Tet-KK-CBD1 (C18K) peptide. Bleedings at day 15, 43, and 71 corresponding to 2 weeks after the first, second, and third immunization (histograms 1, 2, and 3, respectively), were tested for their capacity to inhibit HIV-1 infection of primary $CD4^+$ T lymphocytes at serum dilution of 400-fold. Histogram C stands for the control infection, whereas histograms B stand for serum samples before immunization (day 0).

FIG. 12 shows the results of a typical virus neutralization experiment in which HIV-1 infection of T lymphocytes was carried out in the absence or presence of macaque immune sera obtained 4 weeks after the third immunization. Virus production was then monitored by measuring the concentration of HIV major core protein p24 in the culture medium at 5 days post infection. Unexpectedly, immune sera from only one out of the three macaques immunized with the Tet-KK-CBD1 chimeric peptide manifested HIV-1 neutralizing activity in contrast to all of the three macaques immunized with the free CBD1 and Tet peptide. The HIV-1 inhibitory effect was more pronounced at 400-fold compared to 200-fold dilution, which might be due to a complete loss of the intrinsic enhancing effect at higher dilutions of macaque sera. The degree of inhibition of HIV-1 infection was 60-75% at 400-fold dilution of the immune sera of macaques that manifested neutralizing activity (FIG. 13).

The lack of HIV-1 neutralizing activity of macaque M13246 and M13510 immune sera (FIG. 12) in spite of the presence of anti-CBD1 antibodies (FIG. 11, Table 9) suggest that neutralizing antibodies correspond to a small proportion of the total anti-CBD1 antibodies. In accord with this, no neutralization was observed with M13284, M13421, and M13450 immune sera after the first immunization although high titered anti-CBD1 antibodies were produced. Similarly, although the anti-CBD1 titer in macaques M13284 and M13241 reached a plateau after the second immunization, the respective neutralizing activity was higher after the third compared to the second immunization (FIG. 13 Table 9).

Fine Epitope Mapping of Macaque Immune Sera

Figure 14:
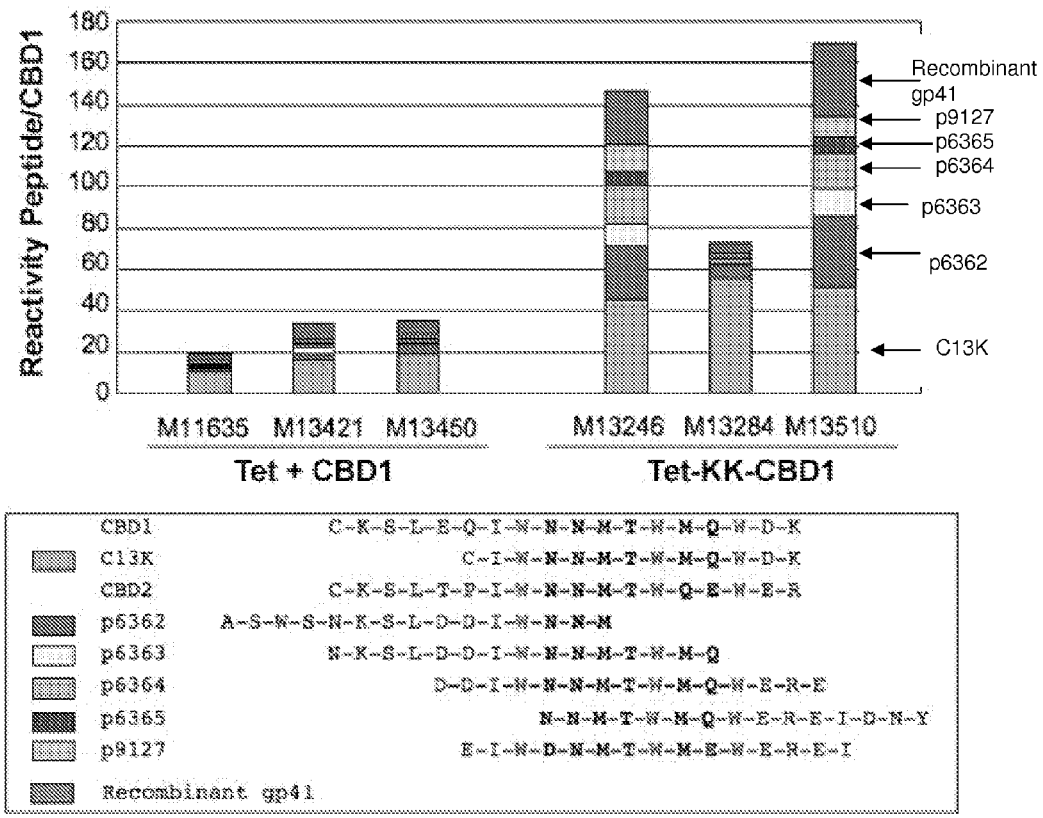
FIG. 14 is a graph showing the cross-reactivity profile of immune sera raised in macaques against the CBD1 (C18K) peptide, either free or fused to a T helper epitope. Immune sera from the immunized macaques four weeks after the third immunization (day 86) were tested by ELISA against CBD1 (amino acid residues 618-633 in gp41), C13K, CBD2, p6362, p6363, p6364, p6365, p9127, and recombinant gp41 (amino acid residues 586-682). The O.D. values observed at 8,000-fold dilution of the immune sera against the various peptides were used to estimate the cross-reactivity, obtained by the ratio that was calculated by dividing the reactivity of each peptide by the reactivity with the CBD1 peptide X 100. None of the immune sera cross-reacted with the CBD2 peptide.

In order to characterize the immune humoral response induced in macaques immunized with the free CBD1 and Tet peptide compared to the chimeric Tet-KK-CBD1 peptide, the reactivity of immune sera was tested against various CBD1-related peptides: the C13K peptide corresponding to the C-terminal portion of the CBD1 peptide, the CBD2 peptide that is the CBD1 peptide homologue in HIV-2, a series of peptides with amino acid sequences overlapping the caveolin-1 binding motif within N- and C-terminally modified amino acid residues, and a recombinant preparation of gp41 (FIG. 14). These studies revealed major differences in the cross-reactivity profile of neutralizing and non-neutralizing macaque immune sera. Indeed, non-neutralizing immune sera (macaques M13246 and M13510) was distinguished from neutralizing immune sera (macaques M11635, M13421, M13450 and M13284) by a strong cross-reactivity with various overlapping peptides p6362, p6363, p6364, p6365 and p9127, as well as with the recombinant gp41. This wide spectrum of cross-reactivity was specific, since none of the immune sera reacted with the CBD2 peptide. These results illustrate that co-immunization of free CBD1 and Tet peptide, rather than the fused Tet-KK-CBD1 peptide, favors the development of neutralizing antibodies.

Figure 15:
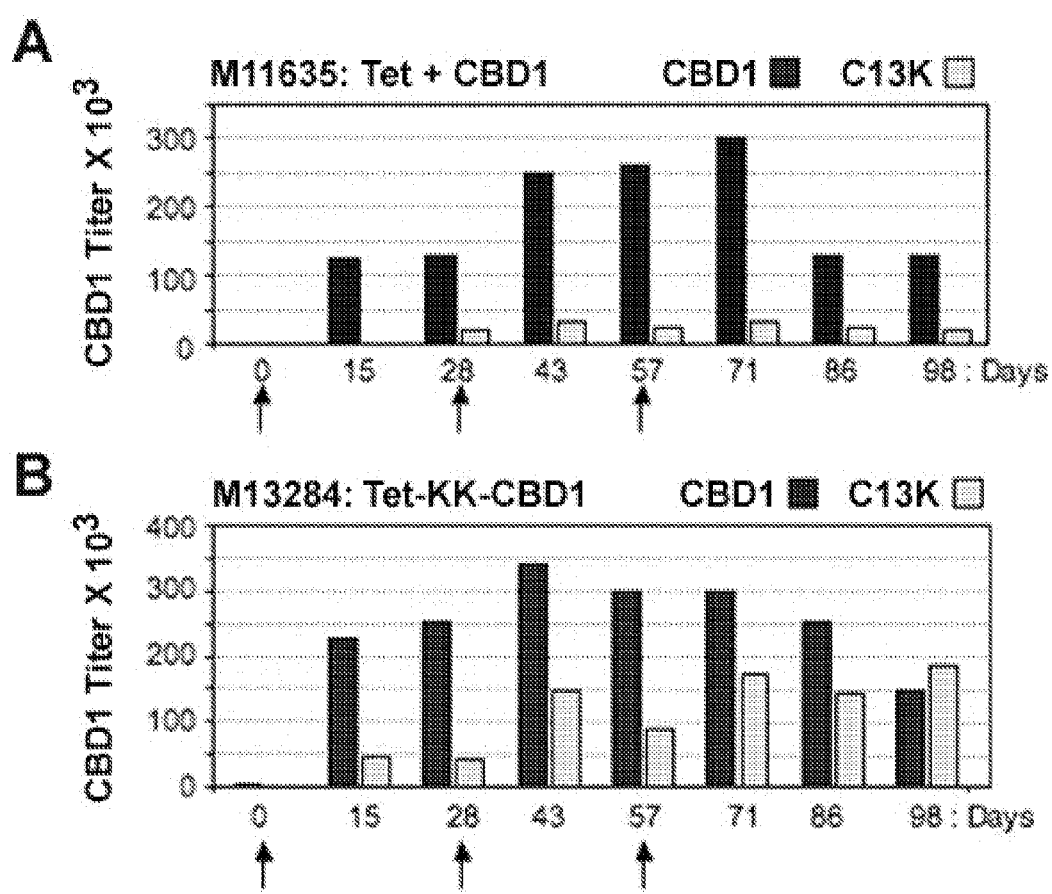

A notable difference in ELISA of immune sera raised against the CBD1 or Tet-KK-CBD1 immunogens is the cross-reactivity with the C13K peptide, which has an amino acid sequence identical to the last 12 residues of the CBD1 peptide. FIG. 15 shows the kinetics of the production of anti-CBD1 and anti-C13K antibodies in macaque M11635 and M13284 immunized with free and fused CBD1 peptide, respectively. Consistently, antibodies induced by Tet-KK-CBD1 cross-reacted strongly with the C13K peptide. These anti-C13K reactive antibodies were generated later in time during the immunization period compared to the production of anti-CBD1 reactive antibodies (FIG. 15). As both immune sera manifested neutralizing activity against HIV-1 infection, the significance of cross-reactivity with the C13K remains to be further investigated. Interestingly, high titered C13K reactive antibodies were also generated in rabbits, guinea pigs and mice immunized with Tet-KK-CBD1 (unpublished results). Therefore, the presence of the N-terminal T helper epitope significantly affects the eventual immune response against the CBD1 peptide. This latter could be accounted by the generation of alternative HLA class II agretopes in the CBD1 sequence when presented in the context of the chimeric Tet-KK-CBD1 peptide.

TABLE 9

The humoral immune response against the CBD1 and Tet peptide in the sera of macaques immunized with the CBD1 peptide and the tetanus T helper epitope peptide, either as free peptides or a chimera linked with the dilysine linker.

| | | CBD1-ELISA: 15 days after $1^{st}$, $2^{nd}$ and $3^{rd}$ injections | | | | Tet-ELISA: 15 days after $1^{st}$, $2^{nd}$ and $3^{rd}$ injections | | | |
|---|---|---|---|---|---|---|---|---|---|
| Macaque | Antigen | Before | First | Second | Third | Before | First | Second | Third |
| M13246 | Tet-KK-CBD1 | <200 | 32,000 | 65,000 | 40,000 | <200 | 1,000 | 3,000 | 5,000 |
| M13284 | Tet-KK-CBD1 | 2,000 | 200,000 | 300,000 | 300,000 | <200 | 200 | 10,000 | 20,000 |
| M13510 | Tet-KK-CBD1 | 5,000 | 100,000 | 150,000 | 100,000 | <200 | 200 | 1,500 | 3,000 |
| M11635 | Tet + CBD1 | 1,000 | 130,000 | 250,000 | 400,000 | <200 | <200 | 200 | 400 |
| M13421 | Tet + CBD1 | 4,000 | 250,000 | 500,000 | 450,000 | <200 | 200 | 1,000 | 100,000 |
| M13450 | Tet + CBD1 | <100 | 2,000 | 16,000 | 40,000 | <200 | 200 | 600 | 400 |

Four months after the last immunization (fifth injection) of macaques described in FIG. 10, animals were bled to assay the level of antibody titers (Before).
The macaques in two groups were immunized subcutaneously with Tet-KK-CBD1 (Tet fused to CBD1, 350 µg) or with CBD1 + Tet (free CBD1 and Tet peptide, 200 µg + 150 µg) using as adjuvant the mixture composed of [CpG + Montanide ISA 51].
Bleedings at day 15, 43 and 71 (corresponding to 2 weeks after the first, second, and third immunizations, respectively) were assayed by ELISA against the CBD1 or Tet peptide.
The titers correspond to the dilution of anti-CBD1 peptide antibodies giving OD value ≥0.1 in ELISA.

Example 10

Confirmation of the Existence of Multiple Overlapping Neutralizing Determinants in the CBD1 Epitope by Generating Specific Monoclonal Antibodies (mAbs)

Peptide vaccines able to induce neutralizing antibodies must rely in part on the design of antigenic epitopes that mimic the three-dimensional structure of the corresponding region in the native protein.

The demonstration that the CBD1 peptide and the CBM-derived peptides fused with T helper epitopes elicit HIV-neutralizing antibodies, which do not cross-react with related CBM-derived peptides indicates the existence of distinct and overlapping neutralizing determinants, which are probably the reflection of the dynamic conformational feature of the CBD1 epitope. Therefore, the CBD1 peptide and the CBM-derived peptides have the capacity to mimic the distinct flexible conformations generated by the dynamic structure of the CBD1 epitope in the native HIV-gp41 protein. In accord with this, the mixture of neutralizing immune sera raised against the CBD1 peptide and different CBM-derived peptides results in a synergistic neutralizing activity against HIV-1 infection (Tables 7 and 8). Consequently the reactivity of antibodies against several distinct conformational determinants simultaneously, results in a strong neutralizing activity.

The presence of overlapping conformational determinants in the CBD1 epitope is confirmed by the generation of monoclonal antibodies (mAbs) by using as immunogens the The CBD1 peptide and the various CBD1- and CBM-derived peptides. Altogether, 19 mAbs were isolated with different degrees of HIV-1 neutralizing activity. These mAbs were characterized into 11 subgroups by virtue of their cross-reactivity with the various CBD1- and the CBM-based peptides, thus illustrating the existence of distinct conformational determinants in the CBD1 epitope.

Four series of immunizations of mice were carried out using the CBD1 peptide, and CBD1 and CBM derived peptides. Several monoclonal antibodies were isolated and characterized for their reactivity with various peptides containing various overlapping segments of the caveolin-1 binding domain in gp41. The isolated mAbs can be grouped into 11 main sub-groups according to their reactivity with the CBD1 peptide and various CBD1- and CBM-based peptides: CBD1 (C17K), C13K, CBD2, p62, C10M, K27M, K29K, K24W, K27W(G), K30W(G) and K27W (Table 10).

TABLE 10

The monoclonal antibodies against the CBD1 can be characterized into 11 groups according to their reactivity with CBD1- and CBM-based peptides.

| Group and | ELISA against the CBD1 peptide and CBD- or CBM-based peptides | | | | | | | | | | |
|---|---|---|---|---|---|---|---|---|---|---|---|
| Immunogen | C17K | C13K | CBD2 | P6362 | C10M | K27M | K29K | K24W | K27W | K27W(G) | K30W(G) |
| 1. C17K | +++ | ++ | ++++ | - | - | - | +++ | - | + | - | +++ |
| 2. A36K | ++++ | ++++ | ++++ | - | - | - | +++++ | - | ++++ | - | +++++ |
| 3. C17K, K29K | ++++ | ++++ | - | - | - | - | ++++ | - | - | - | - |
| 4. C17K | ++++ | +++ | - | + | ++++ | +++++ | +++ | - | - | - | - |
| 5. A36K | ++++ | - | - | +++++ | +++++ | +++++ | - | - | - | ++++ | + |
| 6. K27M | - | - | - | - | +++++ | +++++ | - | - | - | - | - |
| 7. K27M | - | - | - | - | - | +++++ | - | - | - | - | - |
| 8. C17K | ++++ | - | - | + | +++ | +++++ | - | - | - | - | - |
| 9. K24W | - | - | - | - | - | - | - | +++++ | - | ++++ | - |
| 10. K30W(G) | - | - | - | - | - | - | - | ++ | ++ | ++ | ++ |
| 11. K29K | ++++ | +++ | - | - | - | - | +++ | - | ++++ | - | +++++ |

The minus sign represents lack or poor reactivity in ELISA with the peptides as indicated. The immunogen peptide represents the peptide that was used to immunize the mouse from which the spleen cells were used for the preparation of the specific mAb. The + signs stand for reactivity: + = 10,000-50,000; ++ = 50,000-100,000; +++ = 500,000-1,000,000; ++++ = 1,000,000-2,000,000; +++++ = 3,000,000-4,000,000.

* C17K: C-SLEQIWNNMTWMQWDK
* C13K: C-IWNNMTWMQWDK
* CBD2: C-SLTPDWNNMTWQEWER
* p6362: ASWSNKSLDDIWNNM
* C10M: C-SLEQIWNNM
* K27M: Gag-KK-C-SLEQIWNNM
* K29K: Gag-KK-IWNNMTWMQWDK
* K24W: Gag-KK-IWNNMTW
* K27W(G): Gag-GPGPG-IWNNMTW
* K27W: Gag-KK-IWNNMTWMQW
* K30W(G): Gag-GPGPG-IWNNMTWMQW
* A36K: Tet-KK-C-KSLEQIWNNMTWMQWDK

On the basis of the reactivity of each mAb in ELISA with the various peptides CBD1 (C17K), C13K, CBD2, p6362, C10M, K27M, K29K, K24W, K27W, K27W(G) and K30W (G), the peptide-sequence of the determinants were defined (Table 11). The capacity of different mAbs to react with a given sequence but in different peptides, indicates reactivity with distinct conformational determinant of the same sequence (Table 11). These 11 overlapping determinants are the following: IWNNMTWMQWDK (in 3 conformations), IWNNM (in 2 conformations), SLEQIWNNM (in 3 conformations), IWNNMTW (in 2 conformations), and IWNNMTWMQW.

TABLE 11

The monoclonal antibodies (mAb) against the CBD1 epitope react with distinct but overlapping determinants.

| Group | Immuno-gen | mAb | Determinant |
|---|---|---|---|
| 1 | C17K | 81.4 | IWNNMTWMQWDK |
| 2 | A36K | U.13 | IWNNMTWMQWDK |
| 3 | C17K/K29K | E.5.4, H18.4/1.1.1, 1.1.2 | IWNNMTWMQWDK |
| 4 | C17K | E5.1 | IWNNM (SEQ ID No 48) |
| 5 | A36K | 5B15, 6B9 | IWNNM |
| 6 | K27M | 16.2 | SLEQIWNNM (SEQ ID No 49) |
| 7 | K27M | 4.1 | SLEQIWNNM |
| 8 | C17K | H21.3 | SLEQIWNNM |
| 9 | K24W | F1.1, F1.3, F6.4, H3.1 | IWNNMTW (SEQ ID No 50) |
| 10 | K30W(G) | N1.1, N1.3 | IWNNMTW |
| 11 | K29K | 9.1 | IWNNMTWMQW (SEQ ID No 51) |

Table 11 presents the 11 subgroups (numbers 1-11) of mAbs according to their cross-reactivity with various peptides as described in Table 10. On the basis of such cross-reactivity, the different determinants were identified. The peptide that was used as immunogen for the generation of each mAb is given. The column mAb gives the names of different mAbs in each subgroup. The tryptophan residues of the CBM are underlined.

The mAbs 1.1.1, 1.1.2, E5.4, H18.1, 81.4 and U.13 react with 3 distinct conformations of the determinant, IWNNMTWMQWDK, as deduced from their reactivity with 2, 3 and 4 peptides among C13K, CBD2, K29K, K27W, respectively.

The mAbs 4.1, 16.2 and H21.3 react with 3 distinct conformations of the determinant, SLEQIWNNM, as deduced from their reactivity with 1, 2 and 3 peptides among C17K, K27M and C10M, respectively.

The mAb 5B15, 6B9 and E5.1 react with 2 distinct conformations of the determinant, IWNNM, as deduced from their reactivity with 2 and 4 peptides among C17K, C13K, C10M and K27W(G), respectively.

The mAb N.1.1, N1.3 and F1.1, F1.3, F6.4 and H3.1 react with 2 distinct conformations of the determinant, IWN-NMTW, as deduced from their reactivity with either one or both of the peptides, K27W(G) and K30W(G).

The mAb 9.1 reacts with a distinct determinant, IWN-NMTWMQW, as deduced from its strong reactivity with the K27W or K30W(G) peptide.

The isolation of HIV-neutralizing mAbs raised against the CBD1 peptide and CBD1- and CBM-based chimeric-peptide points out the importance of the CBD1 epitope as an efficient B-cell epitope for an AIDS vaccine preparation.

Figure 6:
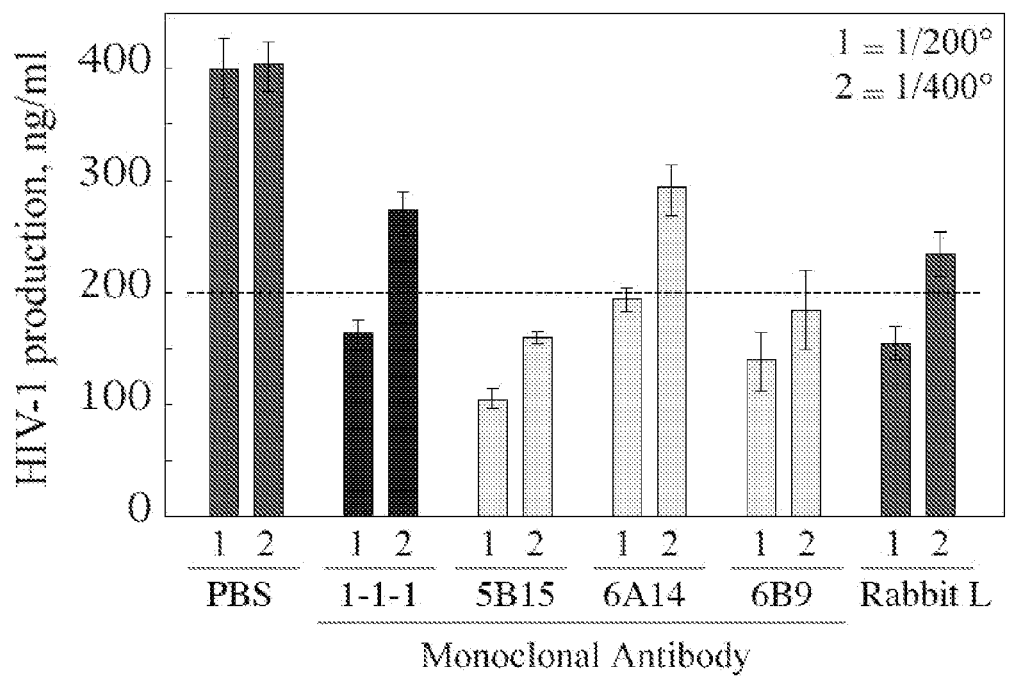
FIG. 6 is a graph showing the neutralization of HIV-1 infection by monoclonal antibodies raised against the CBD1 (C17K) peptide and CBD1-based peptides. HIV-1 BZ 167 was incubated with various dilutions (in PBS) of each monoclonal antibody preparation for 45 minutes at 37° C. before infection of primary CD4$^+$ T lymphocytes. The results are presented for monoclonal antibodies 1.1.1, 5B15, 6A14 (also referred to as F6.4) and 6B9, at 200- and 400-fold dilutions. Rabbit L serum was raised against the CBD1 peptide. HIV-1 production was monitored by monitoring the p24 concentration in the culture medium at 5 days post-infection.

Most of the mAbs have the capacity to inhibit HIV-1 BZ 167 infection in the primary $CD4^+$ T lymphocyte culture, with $ID_{50}$ values ranging from 100- to 500-fold dilutions. FIG. 6 shows representative results obtained for mAb 1.1.1, 5B15, 6A14 (also referred as F6.4) and 6B9.

Figure 7A:
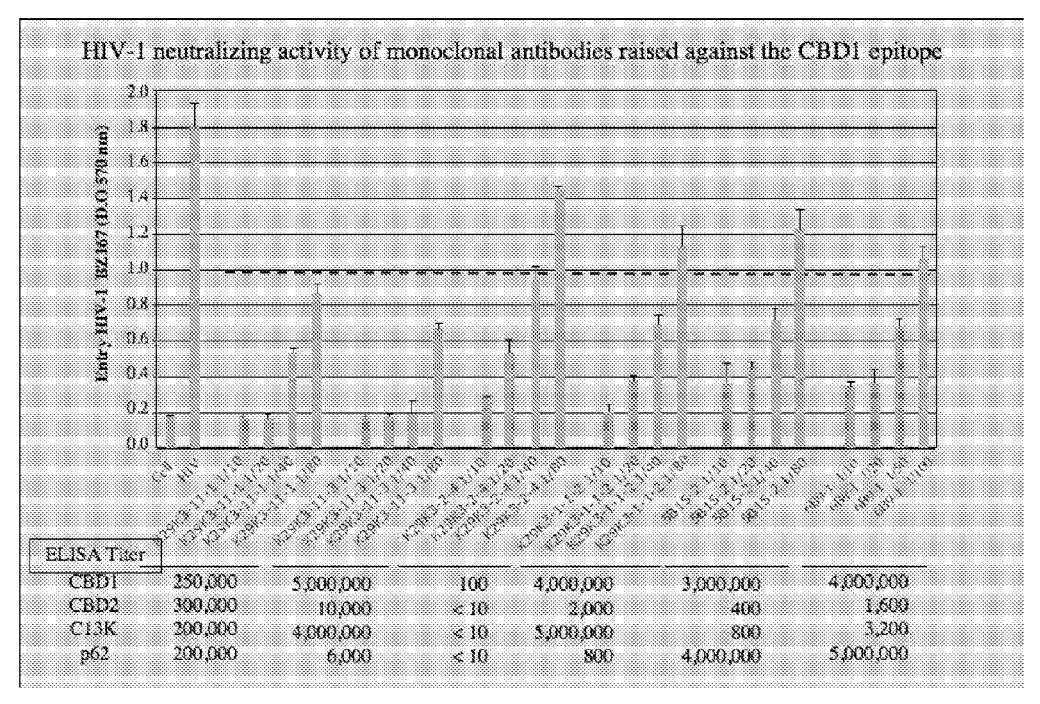
Figure 7B:
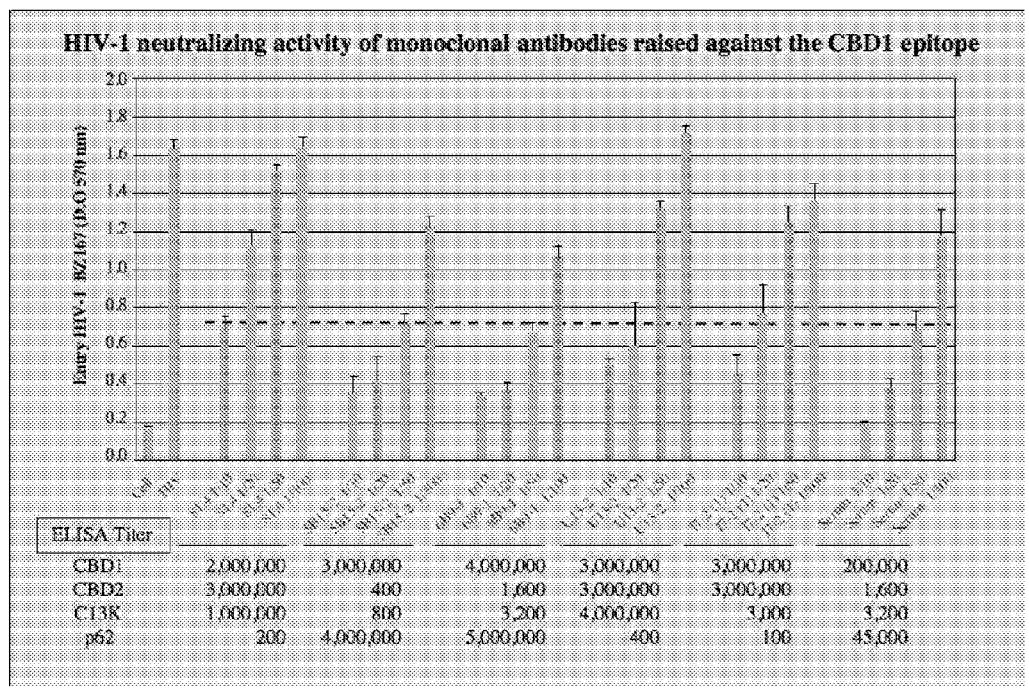
FIGS. 7 A and 7B are graphs showing the HIV-1 neutralizing activity of monoclonal antibodies raised against the CBD1 (C17K) epitope. HIV-1 BZ 167 was incubated with various dilutions of each monoclonal antibody preparation for 45 minutes at 37° C. before infection of HeLa P4 cells. The activity of β-galactosidase was measured 48 hours post-infection. The dashed line gives the OD of the 50% inhibitory effect. The titer of each monoclonal antibody preparation in ELISA against the CBD1, CBD2, C13K, and p62 peptide is given below each graph.

Interestingly, the mAbs directed against the CBD1 epitope have the capacity to inhibit the single cycle HIV-infection of HeLa-CD4-LTR-lacZ cells that contain the bacterial lacZ gene under the control of HIV-1 LTR (Nisole et al., 1999). In this experimental model of HIV entry, the neutralizing activity of mAbs is observed at 10- to 100-fold dilution (FIG. 7). It should be noted that under similar experimental conditions, the human mAb 2F5 had no effect, although mAb 2F5 inhibits the same HIV-1 isolate in the $CD4^+$ T lymphocytes. This difference in the inhibition of HIV entry into HeLa P4 cells by anti-CBD1 mAbs compared to mAb 2F5 remains to be determined.

The titer of each mAb preparation against the CBD1, CBD2, C13K, and p6362 peptide is given below the graphs in FIG. 7. As we had observed with various immune sera, the titers of the antibody of the various mAbs are not strictly correlated to the degree of inhibition of HIV infection. This latter is most probably due to the fact that the ELISA assay monitors reactivity with a given peptide that might have a specific confirmation, which might be slightly different from the conformation of the CBD1 epitope in the native gp41 molecule. Whatever is the case, the lack of reactivity with the CBD2 peptide is often correlated with a lower inhibitory activity on HIV infection. The hybridoma producing mAb K29K3-2-4 was selected because of its specific but very low titer against the CBD1 peptide. This mAb inhibits HIV-1 entry in the HeLa P4 model at 40-fold dilution, whereas it inhibits HIV infection in T lymphocytes at 75-fold dilution.

Example 11

Application of the CBD1 Peptide, or CBD1- and CBM-Based Peptides as a Therapeutic Vaccine in AIDS Patients It was previously shown that only a very small proportion HIV-1 infected individuals have antibodies against the CBD1 peptide with low ELISA titers (Hovanessian et al., 2004b). For this purpose, the presence of IgG antibodies against the immunogenic epitope in gp41 containing the disulfide loop (Peptide 600-612) and the caveolin-1 binding domain in gp41, i.e., the CBD1 epitope (Peptide 618-633) were tested by ELISA. Human HIV-1 positive and negative sera were tested at a 1000-fold dilution. The mean of OD values measured at 450 nm±S.D. (in parenthesis) is given for each group (n=the number of sera tested). The cut-off points of each assay were determined with the sera from 30 non-HIV-infected individuals from each country (Hovanessian et al., 2004b).

The results indicated that only a very small proportion of sera from HIV-1-infected individuals react weakly with the CBD1 peptide, whereas the reactivity of these same sera with the immunodominant epitope, peptide 600-602, is highly elevated (Table 12).

TABLE 12

The rare presence of anti-CBD1 antibodies in HIV-1 infected individuals

| Serum HIV-1 positive | Origin | ELISA/peptide 600-612 | ELISA/CBD1 peptide 618-633 |
|---|---|---|---|
| n = 81 | France | 81/81 (2.25 ± 0.58) | 4/81 (0.33 ± 0.05) |
| n = 24 | Chili | 24/24 (2.02 ± 0.53) | 1/24 (0.30) |
| n = 22 | Brazil | 22/22 (1.50 ± 0.66) | 1/22 (0.75) |

In another cohort of 75 HIV-1-positive individuals whose sera were all highly positive for the gp41 immunodominant peptide (peptide 600-612), only two sera were found to be positive for the CBD1 peptide (C17K) in ELISA. Fine epitope mapping of these 2 sera was carried out by ELISA using various overlapping CBD1- or CBM-based peptides (Table 13).

These two sera were tested by ELISA for the presence of IgG antibodies against the CBD1, CBD2, p62 and C10M peptide, and the CBD1-based peptides: C13K, K29K, K27W, K24W, K23M and K27M. The titer of anti-CBD1 peptide antibodies of these two sera was 6,400 and 12,800, respectively. The titer of each serum corresponded to the dilution of serum giving OD value of 0.2 in ELISA. The results are shown in Table 13.

TABLE 13

Fine epitope mapping of the 2 CBD1 positive sera out of 75 HIV-1 infected individuals.

| Peptide | Sequence of peptides in ELISA | Reactivity of anti-CBD1 positive sera from 2 HIV-1 seropositive individuals |
|---|---|---|
| C17K | SLEQIWNNMTWMQWDK | +/+ |
| C13K | CIWNNMTWMQWDK | -/- |
| CBD2 | SLTPDWNNMTWQEWER | -/- |
| p62 | ASWSNKSLDDIWNNM | -/- |
| K29K | Gag-KK-IWNNMTWMQWDK | -/- |
| K27W | Gag-KK-IWNNMTWMQW | -/- |
| K24W | Gag-KK-IWNNMTW | -/- |
| K23M | Gag-KK-IWNNM | -/- |
| K27M | Gag-KK-C-SLEQIWNNM | +/+ |
| C10M | C-SLEQIWNNM | +/+ |

The results indicated that the 2 sera positive for the CBD1 peptide in fact react with its the N-terminal portion. No reactivity was observed with peptides corresponding to various segments of the conserved caveolin-binding motif.

These results therefore indicate that HIV-1 infected individuals do not produce antibodies against the conserved caveolin-1 binding motif (CBM), which is the determinant in the CBD1 epitope for the action of neutralizing antibodies. The lack of production of natural antibodies against the CBD1 epitope in HIV-1 infected individuals could be due to N-linked glycosylation of the $N^{625}$ (Johnson et al., 2001), which could hinder the development of an immune response (Rudd et al., 2001).

The fact CBD1 and CBD1-based peptides are immunogenic in macaques and produce neutralizing antibodies, and the lack of antibodies against the CBD1 epitope in HIV-1 infected individuals from several geographic origins, CBD1-based vaccines could have applications as a therapeutic vaccine in AIDS patients.

Example 12

The Immunogenicity and Efficacy of a Mixture of Overlapping CBD1-Based Peptides as a Vaccine Candidate for HIV/AIDS In example 8 (above), it was shown that the CBM-based peptides IWNNMTWMQW and IWNNMTW when fused to a T helper epitope are immunogenic by inducing high titer CBM-specific antibodies capable of neutralizing HIV-1 infection in primary T lymphocyte cultures. Neutralizing immune sera raised against a given peptide do not cross-react with related CBM-derived peptides, thus suggesting the existence of distinct neutralizing conformational epitopes in CBD1 (Table 7). The existence of several distinct overlapping epitopes in CBD1 was confirmed by murine monoclonal antibodies that were generated against the CBM-derived chimeric peptides.

These results pointed out that CBD1 contains several overlapping B-cell epitopes that represent the target of potential neutralizing antibodies against HIV-1. In accord with this, the mixture of neutralizing immune sera raised against various peptides resulted in a synergistic neutralizing activity against HIV-1 infection (Table 8). It might be possible that specific antibodies in the mixture of the immune sera could exert a strong HIV-1 neutralization by reacting simultaneously with distinct epitopes within the CBM, which are probably generated by the dynamic structure of CBD1 in the native HIV-gp41 protein.

Therefore CBD1- and CBM (caveolin-1 binding motif)-based peptides mimic distinct dynamic conformations of CBD1 in gp41 of HIV-1, and thus mediate the induction of neutralizing antibodies. This and the synergism in HIV-neutralization observed by the mixture of the immune sera reacting with distinct epitopes in CBD1, suggest that a cocktail of CBM-derived peptide-chimeras should be considered for a candidate vaccine preparation in order to elicit an efficient humoral immune response against HIV-AIDS infection.

In the present example, the immunogenicity of such a cocktail-vaccine preparation in mice has been undertaken, while the immunogenicity and efficacy studies are currently being evaluated in cynomolgus macaques using adjuvants that are acceptable for human use.

A. Immunogenicity of CBD1-Based Cocktail Peptides in Mice.

Two groups of 8 BALB/C mice (6-8 week-old) were immunized with Cocktail A and Cocktail B peptides (as defined below), using complete Freund's adjuvant (CFA). Four subcutaneous injections were administered at one-month interval.

```
Cocktail A peptides: C17K + K27W + K24W + K30W/G + K27W/G
(Each peptide in the cocktail was at 80 ug/mouse/injection)

C17K:          C -S-L-E-Q-I-W-N-N-M-T-W-M-Q-W-D-K    SEQ ID NO: 31

K27W:          Gag298-312-K-K-I-W-N-N-M-T-W-M-Q-W    SEQ ID NO: 12

K24W:          Gag298-312-K-K-I-W-N-N-M-T-W          SEQ ID NO: 35

K30W(G): Gag298-312-G-P-G-P-G-I-W-N-N-M-T-W-M-Q-W    SEQ ID NO: 16

K27W(G): Gag298-312-G-P-G-P-G-I-W-N-N-M-T-W          SEQ ID NO: 38

Cocktail B peptides: K27W + K24W + K30W/G + K27W/G
(Each peptide in the cocktail was at 80 ug/mouse/injection)

K27W:          Gag298-312-K-K-I-W-N-N-M-T-W-M-Q-W    SEQ ID NO: 12

K24W:          Gag298-312-K-K-I-W-N-N-M-T-W          SEQ ID NO: 35

K30W(G): Gag298-312-G-P-G-P-G-I-W-N-N-M-T-W-M-Q-W    SEQ ID NO: 16

K27W(G): Gag298-312-G-P-G-P-G-I-W-N-N-M-T-W          SEQ ID NO: 38
``` with the sequence of $Gag_{298-312}$ is: K-R-W-I-I-L-G-L-N-K-I-V-R-M-Y (SEQ ID NO:4).

A.1. The Humoral Response in Mice Immunized with the Cocktail A and Cocktail B Peptides.

Two weeks after the 4th immunization, the immune sera were tested by ELISA against the cocktail A and cocktail B peptides. The titer of the anti-cocktail A and anti-cocktail B antibody corresponds to the reciprocal dilution of the immune serum giving an $OD_{450nm}$ value equal to 0.1. Experimental conditions for ELISA were as described in point 2.1 of methods above. Results are presented in Table 14. The immunogenicity of individual peptides in mice has been described in Example 8B and Table 8.

TABLE 14

Antibody titer of the immune sera (S4) from mice immunized with the cocktail A and cocktail B peptides against the respective cocktail

| Mouse immunized with Cocktail A | ELISA titer against Cocktail A | Mouse immunized with Cocktail B | ELISA titer against Cocktail B |
|---|---|---|---|
| 1 | 1,000,000 | 1 | 100,000 |
| 2 | 400,000 | 2 | 1,000,000 |
| 3 | 600,000 | 3 | 200,000 |
| 4 | 200,000 | 4 | 300,000 |
| 5 | 300,000 | 5 | 100,000 |
| 6 | 150,000 | 6 | 2,000,000 |
| 7 | 400,000 | 7 | 200,000 |
| 8 | 500,000 | 8 | 300,000 |

The proportion of IgG1 and IgG2a subclass antibodies in the immune sera of mice was determined using goat anti-mouse IgG1 and IgG2a antibodies (Sigma). The IgG2/IgG1 ratio estimated by ELISA against the respective cocktail immunogen in individual mice was <0.04.

Although there was some variability in the degree of antibody titer among individual mice of each group, the antibody titers were quite elevated ranging between 100,000 to 2,000,000. Studies on the proportion of IgG1 and IgG2a subclass antibodies in the immune sera of mice indicated that the antibody subtype in the immune sera generated against cocktail A and cocktail B peptides was predominantly of the IgG1 type, the proportion of which was >96% in various individual immune serum. It should also be noted that the Gag T helper epitope is not immunogenic as illustrated by the lack of reactivity of the immune sera with the T helper epitope peptide $Gag_{298-312}$ (not shown).

The immunogenicity of individual peptides, when administered together in either cocktail A or cocktail B, was next investigated. For this purpose, two weeks after the 4th immunization, the immune serum in each group of mice was tested by ELISA against individual peptides, i.e. C17K, K27W, K24W, K30W/G, and K27W/G peptide (Table 15 for cocktail A and Table 16 for cocktail B). The antibody titers against each peptide correspond to the reciprocal dilution of the immune serum giving an $OD_{450nm}$ value equal to 0.1. Experimental conditions for ELISA were as described in point 2.1 of methods above

TABLE 15

The immunogenicity of individual peptides when administered together in cocktail A; Antibody titer of the immune sera from mice immunized with the cocktail A peptides against individual peptides: C17K, K27W, K24W, K30W(G) and K27W(G).

| | ELISA titer × 1,000 against CBD1 epitope based peptides | | | | |
|---|---|---|---|---|---|
| Mouse | C17K | K27W | K24W | K30W(G) | K27W(G) |
| 1 | 150 | 40 | 2,000 | 650 | 2,000 |
| 2 | 300 | 100 | 400 | 75 | 4 |
| 3 | 200 | 100 | 700 | 800 | 1,000 |
| 4 | 150 | 30 | 250 | 150 | 150 |
| 5 | 400 | 70 | 40 | 250 | 75 |
| 6 | 100 | 5 | 75 | 4 | 30 |
| 7 | 300 | 350 | 100 | 50 | 4 |
| 8 | 500 | 250 | 1,200 | 70 | 64 |

TABLE 16

The immunogenicity of individual peptides when administered together in cocktail B; Antibody titer of the immune sera from mice immunized with the cocktail B peptides against individual peptides: C17K, K27W, K24W, K30W(G) and K27W(G).

| | ELISA titer × 1,000 against CBD1 epitope based peptides | | | | |
|---|---|---|---|---|---|
| Mouse | C17K | K27W | K24W | K30W(G) | K27W(G) |
| 1 | <1 | 30 | 30 | 10 | <1 |
| 2 | 50 | 150 | 400 | 500 | 300 |
| 3 | <1 | 100 | 150 | 2 | <1 |
| 4 | <1 | 2 | 300 | <1 | <1 |
| 5 | <1 | 15 | 60 | <1 | <1 |
| 6 | <1 | 2,000 | 2,000 | <1 | <1 |
| 7 | <1 | 150 | 75 | 75 | <1 |
| 8 | <1 | 5 | 200 | 7 | 200 |

When mice were immunized with cocktail A peptides, they all developed high titered anti-C17K antibodies, while the production of antibodies against the K27W, K24W, K30W/G, and K27W/G peptide was variable among different individuals (Table 15). Among these four latter peptides, the capacity of a given mouse to produce high titered antibodies against one peptide did not systematically correlate with the capacity to generate a humoral immune response against the other three peptides, thus indicating that the processing of individual peptides could be slightly different between individual mice. In mice immunized with cocktail B peptides, the immune serum of mouse number 2 that generated high titered antibodies against the individual peptides of cocktail B (K27W, K24W, K30W/G, K27W/G) cross-reacted with the C17K peptide (Table 16). In general, the K27W and K24W peptides seemed to be better immunogens than the K30W/G and K27W/G peptides when administered together in cocktail B. Nevertheless, it should be noted that the low reactivity of the immune sera with the K30W/G and K27W/G peptides could be the consequence of the conformation of these peptides. Finally, the antibody titers presented in Tables 14 and 15 show that in the absence of C17K peptide, the immune response raised by the administration of cocktail B against the K30W(G) and K27W(G) peptide is relatively poor, whereas the K24W and K27W peptides remain strong immunogens. Therefore, the presence of the C17K peptide in the cocktail immunogen might favor antibody responses against the K30W(G) and K27W(G) peptide.

A.2. HIV-1 Neutralizing Activity of the Pooled Immune Sera from the Two Groups of Mice Immunized Respectively with Cocktail A and Cocktail B Peptides.

Figure 18:
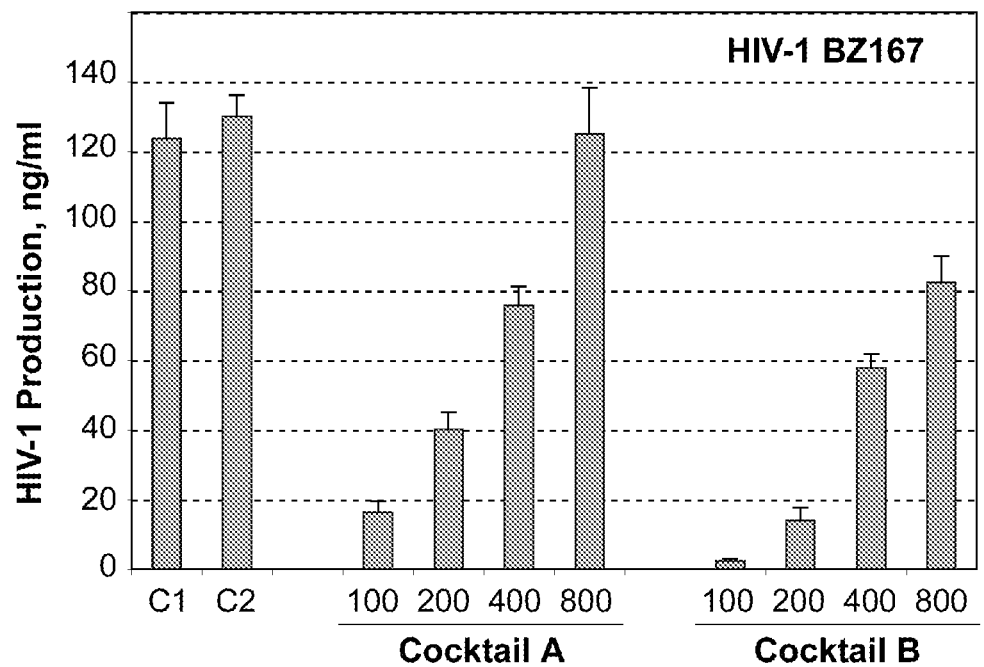

Two weeks after the 4th immunization, the immune sera of each group were pooled and assayed for their capacity to inhibit the primary HIV-1 BZ167 (Clade B) infection of CD4⁺ T lymphocytes. The production of HIV-1 was monitored by measuring the concentration of HIV-1 major core protein p24 in the culture supernatants at 5 days post infection (FIG. 18). Consistent with their strong reactivity with the cocktail A and cocktail B peptides (Table 14), immune sera raised against either cocktail peptides elicited neutralizing antibodies, which inhibited HIV-1 infection in a dose-dependent manner (FIG. 18). Cocktail A and cocktail B pooled-serum dilution that gives 50% inhibition ($ID_{50}$) of HIV-1 BZ167 infection was estimated to be 300- and 400-fold dilutions, respectively.

Figure 19:
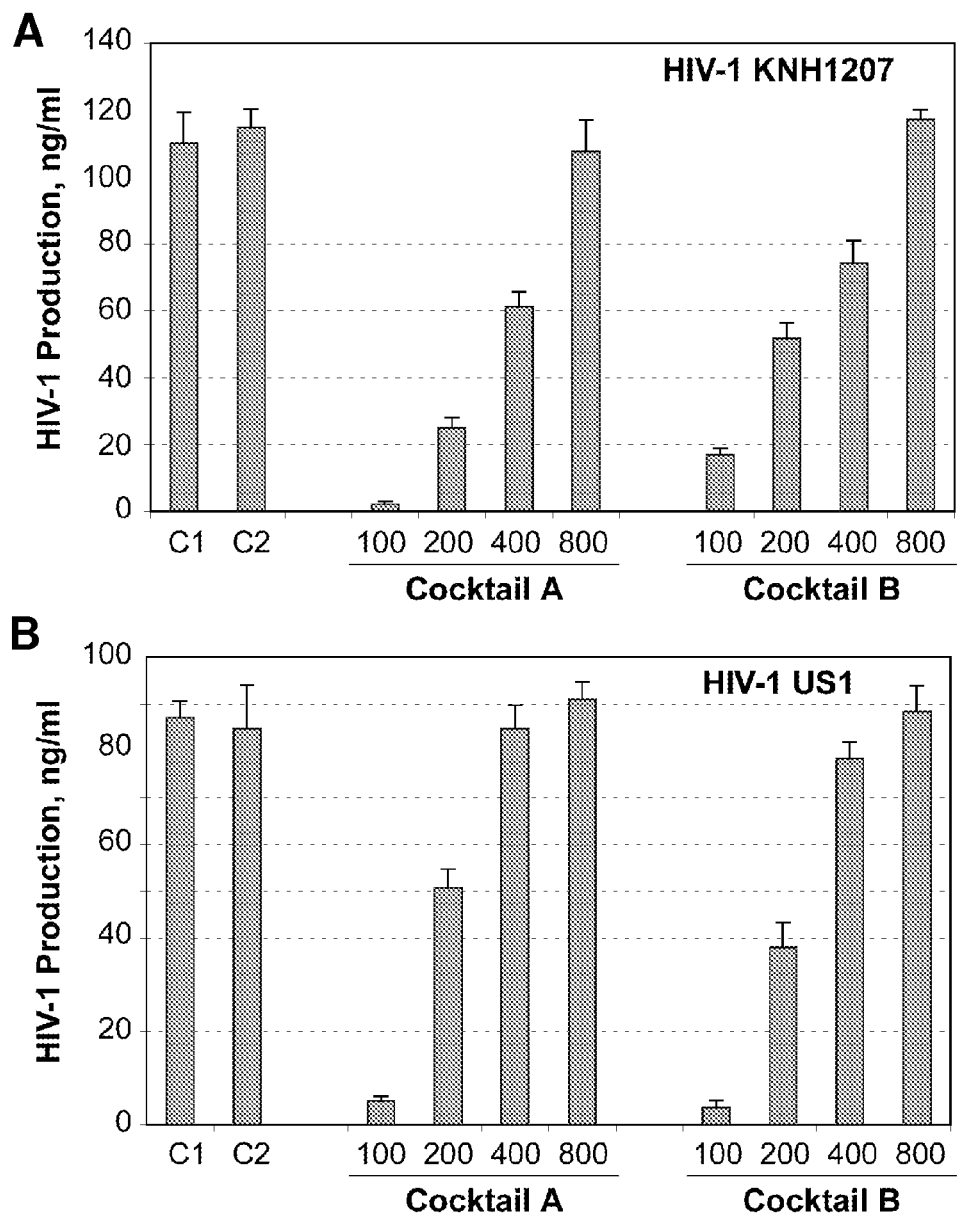
FIG. 19 is a graph showing the neutralizing activity of the pooled immune sera from the two groups of mice immunized respectively with cocktail A and cocktail B peptides against HIV-1 KNH1207 and HIV-1 US1. Two groups of 8 mice were immunized with Cocktail A and Cocktail B peptides as described in the text and in the legend of FIG. 18. The pooled sera from mice immunized with cocktail A and cocktail B peptides were assayed for their capacity to inhibit infection of $CD4^+$ T lymphocytes by two of the international panel of HIV-1 isolates [obtained from AIDS Research and Reference Program, Division of AIDS, NIAID, NIH] that are currently used to test HIV-1 vaccine candidates: HIV-1 KNH1207 (Clade A) (A) and HIV-1 US1 (Clade B) (B). Virus infection was at 50 ng/ml of p24 antigen equivalents, and the pooled sera were used at 100, 200, 400 and 800-fold dilutions. The production of HIV-1 was monitored by measuring the concentration of HIV-1 major core protein (ng/ml, the ordinate) in the culture supernatants at 7 days post infection. Infection of $CD4^+$ T lymphocytes derived from human peripheral mononuclear cells (PBMC) was as described in 2.3 of the paragraph "methods."

The neutralization effect of the pooled sera from cocktail A and cocktail B immunized mice was further studied using several HIV-1 isolates from the international panel of HIV-1 isolates that are currently used to test HIV-1 vaccine candidates: HIV-1 KNH1207 (Clade A), HIV-1Ba-L (Clade B), HIV-1 US1 (GS 004; Clade B), HIV-1 56313 (98US-PSC5016; Clade C), HIV-1 98UG-57128 (Clade D). The pooled immune serum from Cocktail A and cocktail B immunized mice inhibited virus infection of CD4+ T lymphocytes by these different HIV-1 isolates with $ID_{50}$ values ranging from 150 to 350-fold dilution. An example of virus neutralization is presented against HIV-1 KNH1207 and HIV-1 US1 infection of CD4⁺ T lymphocytes in FIGS. 19A and 19B.

B. Immunogenicity and Efficacy of the CBD1-Based Peptide-Cocktail Vaccine-Formulation in Cynomolgus Macaques.

The immunogenicity and efficacy of the CBD1-based peptide-cocktail vaccine-formulation was evaluated in cynomolgus macaques in two phases:

1. by monitoring humoral and cellular immune responses to the cocktail vaccine formulation in immunized animals; and 2. by challenging the immunized animals with a replication competent chimera simian/human immunodeficiency virus (SHIV) that expresses HIV-1 envelope glycoproteins.

A total of 12 macaques were used in this study:
6 macaques immunized with the immunogen and adjuvant;
6 control macaques injected with control-PBS and adjuvant;

Adult male cynomolgus macaques (*Macaca fascicularis*) weighing 4-6 kg, imported from the Mauritius breeding colony, were maintained and handled in accordance with European guidelines for non-human primate care (EEC Directive N 86-609, 24 Nov. 1986). The animals were sedated with ketamine chlorhydrate (10-15 mg/kg) for immunizations and blood sample collections. Immunizations were by subcutaneous injections of the immunogen cocktail using as adjuvant the mixture composed of [CpG+Montanide ISA 51]. For each immunization, 500 µl consisting of one volume of immunogen with one volume of adjuvant mixture were administered.

The cocktail of peptides for the immunogen mix was the following:

| | |
|---|---|
| C17K (150 µg/macaque/injection) | SEQ ID NO: 31 |
| K27W (150 µg/macaque/injection) | SEQ ID NO: 12 |
| K24W (150 µg/macaque/injection) | SEQ ID NO: 35 |
| K30W(G) (150 µg/macaque/injection) | SEQ ID NO: 16 |
| K27W(G) (150 µg/macaque/injection) | SEQ ID NO: 38 |
| $Tet_{A830}$ (A-Q-Y-I-K-A-N-S-K-F-I-G-I-T-E-L) (100 µg/macaque/injection) | SEQ ID NO: 2 |

The peptides were prepared as 4 mg/ml in distilled water (first solubilized with DMSO 10% of the final volume). Then peptides were pooled to give the correct amount of each peptide in the CBD1 cocktail immunogen to inject subcutaneously 6 macaques (for 5 immunizations). The adjuvant used was a mixture composed of a delivery system [Montanide ISA 50 VG, used at 50%] with an immune potentiator [CpG ODN 10103, used at 500 µg/macaque].

The Two Phases of the Study:

In phase I, macaques received five subcutaneous injections on week 0, 4, 10, 16, and 22-26, and the plasma or sera, and PBMC were collected at 2 and 4 weeks after immunization (and 6 weeks when applicable) to test the titer of antibodies by ELISA and also to monitor CBD1 epitope specific IFN-γ production using ELIspot assays.

In phase II, the 6 vaccinated and the 6 control macaques are challenged by the intrarectal route with SHIV162P4, expressing the HIV-1 R5 envelope glycoproteins, 8-10 weeks after the last vaccine boost.

The post-challenge follow-up of the monkeys includes testing seroconversion to viral antigens, monitoring of plasma (by quantitative RT-PCR) and cellular (quantitative PCR-DNA in PBMC) viral load, full hematology including counting circulating CD4⁺ and CD8⁺ T lymphocytes. The post challenge T cell immunity will be monitored by studying the IFN-γ and IL-4 secretion in response to specific stimulation of PBMC with CBD1 peptide and with SIV Gag p27 antigen.

IFN-γ ELISpot Assays:

Cellular immune response against the CBD1-based peptide in the immunized macaques are monitored by stimulating the PBMC, sampled at the indicated day, with CBD1-based peptides (in the cocktail immunogen) in IFN-γ ELISpot assays as described before (point 2.5 of methods above). Peptides that are tested for the IFN-γ ELISpot assay are the following: C17K, K27W, K24W, $Gag_{298-312}$: K-R-W-I-I-L-G-L-N-K-I-V-R-M-Y (SEQ ID NO:4), $Tet_{4830}$: A-Q-Y-I-K-A-N-S-K-F-I-G-I-T-E-L (SEQ ID NO:2) and $gp120_{421-436}$: K-Q-I-I-N-M-W-Q-V-V-G-K-A-M-Y-A (SEQ ID NO:3), as a control peptide.

C. Cocktail of CBM-Derived Peptides Using Various T Helper Epitopes.

The C13K peptide (CIWNNMTWMQWDK) (SEQ ID NO: 33), which is a shorter version of the C17K peptide, is not immunogenic by itself in various animals. However, when fused with T helper epitope peptides using the di-lysine linker, this C13K peptide is immunogenic. Accordingly, A30K, K29K, and K30K chimeric peptides composed of the T helper epitope peptides $Tet_{4830}$, $gp120_{421-436}$, and $Gag_{298-312}$, respectively, fused to the IWNNMTWMQWDK sequence (SEQ ID NO:23) induce high titered HIV-1 neutralizing antibodies (example 8A and Table 5).

The amino acid sequence of the T helper epitope peptides are the following:

```
1) tetanus toxin Tet4830 peptide,
AQYIKANSKFIGITEL;          (SEQ ID NO: 2)

2) HIV-1 gp120421-436 peptide,
KQIINMWQVVGKAMYA;          (SEQ ID NO: 3)
and

3) HIV-1 Gag298-312 peptide,
KRWIILGLNKIVRMY.           (SEQ ID NO: 4)
```

Moreover, when CBM-based peptides IWNNMTWMQW (SEQ ID NO:51) and IWNNMTW (SEQ ID NO:50) are fused to the $Gag_{298-312}$ T helper epitope induce high titer CBM-specific antibodies capable of neutralizing HIV-1 infection in primary T lymphocyte cultures (Example 8). Consequently, such CBM-based peptides IWNNMTWMQW and IWNNMTW could also be used to construct chimeric peptides with the $Tet_{4830}$ and HIV-1 $gp120_{421-436}$ T helper epitopes in order to generate immunogens that could overcome eventual MHC restriction. The use of several T helper epitopes in the chimeric CBM-based peptides is an important parameter to consider in order to covering up most of the MHC class II molecules in human subjects.

The following complementary peptides are examples of peptides that could be included in HIV vaccine cocktail preparations. The co-linear T helper epitope with the CBM-based peptides could be synthesized using the di-lysine (-KK-) linker and the GPGPG spacer as described above:

| Peptide | SEQ ID |
|---|---|
| $Tet_{4830}$-K-K-I-W-N-N-M-T-W-M-Q-W | 52 |
| $Tet_{4830}$-K-K-I-W-N-N-M-T-W | 53 |
| $Tet_{4830}$-G-P-G-P-G-I-W-N-N-M-T-W-M-Q-W | 54 |
| $Tet_{4830}$-G-P-G-P-G-I-W-N-N-M-T-W | 55 |
| $gp120_{421-436}$-K-K-I-W-N-N-M-T-W-M-Q-W | 56 |
| $gp120_{421-436}$-K-K-I-W-N-N-M-T-W | 57 |
| $gp120_{421-436}$-G-P-G-P-G-I-W-N-N-M-T-W-M-Q-W | 58 |
| $gp120_{421-436}$-G-P-G-P-G-I-W-N-N-M-T-W | 59 | with $Tet_{4830}$ consists of sequence AQYIKANSKFIGITEL (SEQ ID NO: 2), and $gp120_{421-436}$ consists of KQIINMWQVVGKAMYA (SEQ ID NO: 3).

REFERENCES (1) Aucouturier, J., Dupuis, L, Deville, S., Ascarateil, S., and Ganne, V. (2002). Montanide ISA 720 and 51: a new generation of water in oil emulsions as adjuvants for human vaccines. Expert Rev, Vaccines/, 111-118.

(2) Belyakov, I. M., and Berzofsky, J. A. (2004). Immunobiology of mucosal HIV infection and the basis for development of a New generation of mucosal AIDS vaccines. Immunity 20, 247-253.

(3) Benferhat, R., Sanchez-Martinez, S, Nieva, J. L., Briand, J. P., and Hovanessian, A. G. (2008). The immunogenic CBDI peptide corresponding to the caveolin-1 binding domain in HIV-1 envelope gp41 has the capacity to penetrate the cell membrane and bind caveolin-1. Molecular Immunology 45, 1963-1975.

(4) Cooper, C. L., Davis, H. L., Morris, M. L., Efler, S. M., Al Adhami, M., Krieg, A. M., Cameron, D. W., and Heathcote, J. (2004). CpG 7909, an immunostimulatory TLR9 against oligodeoxynucleotide, as adjuvant to Engerix-B HBV vaccine in healthy adults: a double-blind phase I/II study. J. Clin. Invest. 24, 693-701.

Chen, X., Rock, M. T., Hammonds, J., Tartaglia, J., Shintani, A., Currier, J., Slike, B., Crowe, J. E. J., Marovich, M., and Spearman, P. (2005). Pseudovirion particles by live poxvirus human immunodeficiency virus vector enhances humoral and cellular immune response. J. Virol; 79, 5537-5547.

(5) Couet, J., Li, S., Okamoto, T, Ikezu, T, and Lisanti, M. P. (1997). Identification of peptide and protein ligands for the caveolin-scaffolding domain. J. Biol. Chem. 272, 6525-6533. Dong, X. N., Yi, X., Dierich, M. P., and Chen, B. K. (2001). N- and C-domains of HIV-1 gp41: mutation, structure and functions. Immunology Letters 75, 215-220.

(6) Egan, M. A., Chong, S. Y., Hagen, M., Megali, S., Schadeck, E. B., Piacente, P., Ma, B. J., Montefiori, C D., Haynes, B. F., Israel, Z. R., et al. (2004). A comparative evaluation of nasal and parental vaccine adjuvants to elicit systemic and mucosal HIV-1 peptide-specific humoral immune responses in cynomolgus macaques. Vaccine 22.

(7) Hirunpetcharat, C, Wipasa, J., Sakkhachornphop, S., Nitkumhan, T. (Sheng, Y. Z., Pichyangkul, S., Krieg, A. M., Walsh, D. S., Heppner, D. G., and Good, M. F. (2003). CpG oliigonucleotide enhances immuunity against blood-stage malaria infection in mice parenterally immunized with a yeat-expressed 19 kDa carboxyl-terminal fragment of Plasmodium yoelii merozoite surface protein-1 (MSP19) formulated in oil-based Montanides, Vaccine 21, 2923-2932.

(8) Hovanessian, A. G. (2003). The Caveolin-Binding Domain in the transmembrane envelope glycoprotein of HIV as a synthetic peptide epitope vaccines for AIDS. Declaration d'Invention 2003-24, Feb. 26, 2003, Institut Pasteur/CNRS, Paris.

(9) Hovanessian, A. G., Briand, J. P., Muller, S., Krust, B., Svab, J., and Said, E. A. (2002), A novel synthetic peptide vaccine for HIV infection: antibodies against the caveolin-binding motif in the transmembrane envelope glycoprotein of HIV block virus entry and budding. Declaration d'Invention 2002-111, Dec. 11, 2002, Institut Pasteur/CNRS, Paris.

(10) Hovanessian, A. G., Briand, J. P., Muller, S., Krust, B., Svab, J., and Said, E. A. (2003). Novel synthetic peptide vaccines for HIV: The CBD epitope as an effective immunogen to elicit broadly neutralizing antibodies against HIV infection. European Patent Deposit, April 2003, Institut Pasteur/CNRS, Paris.

(11) Hovanessian, A. G., Briand, J. P., Muller, S., Krust, B., Svab, J., and Said, E. A. (2004a). The caveolin-1 binding domain of HIV-1 glycoprotein gp41 is an efficient B-cell epitope vaccine candidate against virus infection. United States/Canada Patent Deposit, April 2004, Institut Pasteur/CNRS, Paris.

(12) Hovanessian, A. G., Briand, J. P., Said, A. S., Svab, J., Ferris, S., Dali, H., Muller, S., Desgranges, C, and Krust, B. (2004b). The caveolin-1 binding domain of HIV-1 glycoprotein gp41 is an efficient B-cell epitope vaccine candidate against virus infection. Immunity 21, 617-627.

(13) Jackson, D. C., Purcell, A. W., Fitzmaurice, C. J., Zeng, W., and Hart, D. N. J. (2002). The central role played by peptides in the immune response and the design of peptide-based vaccines against infectious diseases and cancer. Current Drug Targets 3, 175-196.

(14) Johnson, W. E., Sauvron, J. M., and Desrosiers, R. C. (2001). Conserved, N-linked carbohydrates of human immunodeficiency virus type 1 gp41 are largely dispensable for viral replication. J. Virol. 75, 11426-11436.

(15) Kumar, S., Jones, T. R., Oakley, M. S., Zheng, H., Kuppusamy, S. P., Taye, A., Krieg, A. M., Stowers, A. W., kaslow, D. C., and Hoffman, S. L. (2004). CpG oligonucleotide and montanide ISA 51 adjuvant combination enhanced the protective efficacy of a subunit vaccine. Infect. Immun. 72, 949-957.

(16) Lennon-Dumenill, A. M., Bakker, A. H., Wolf-Bryant, P., Ploegh, H. L., and Lagaudriere-Gesbertr, C. A. (2002). A close look at proteolysis and MHC-class-II-restricted antigen presentation. Curr. Opin, Immunol. 14, 15-21.

(17) Lin, G., and Nara, P. L. (2007). Designing immunogens to elicit broadly neutralizing antibodies to the HIV-1 envelope glycoprotein. Curr. HIV Res. 5, 514-541.

(18) Liu, P., Rudick, M., and Anderson, R. G. W. (2002). Multiple functions of caveolin-1. J. Biol. Chem. 277, 41295-41298.

(19) Liu, W., Crockker, E., Zhang, W., Elliott, J. I., Burkhard, L, Li, H., Aimoto, S., and Smith, S. O. (2005). Structural role of glycine in amyloid fibrils formed from transmembrane alpha-helices. Biochemistry 44, 3591-3597.

(20) Livingston, B. D., Crimi, C, Newman, M, Higashimoto, Y., Appella, E., Sidney, J., and Sette, A. (2002). A rational strategy to design multiepitope immunogens based on multiple Th lymphocyte epitope. J. Immunol. 168, 5499-5506.

(21) McMichael, A. J. (2006). HIV Vaccines. Annu. Rev. Immunol. 24, 227-255. (22) McMichael, A. J., and Hanke, T. (2003). HIV vaccines 1983-2003. Nat. Med. 9, 874-880. Morris, K. (2005). B-cell epitope booster for HIV vaccine hope. The Lancet Infectious Diseases. 5, 11.

(22) Nisole, S., Krust, B., Callebaut, C, Guichard, G., Muller, S., Briand, J. P., and Hovanessian, A. G. (1999). The anti-HIV pseudopeptide HB-19 forms a complex with the cell-surface expressed nucleolin independent of heparan sulfate proteoglycans. J. Biol. Chem. 274, 27875-27884.

(23) O'Hagan, D. T., and Rappuoli, R. (2004). Novel approaches to vaccine delivery. Pharmaceutical Research 21, 1519-1530.

(24) Olivtera, G. A., Wetzel, K., Calvo-Calle, M., Nussenzweig, R., Schmidt, A., Birkett, A., Dubovsky, F., Tierney, E., Gleiter, C. H., Boehmer, G., et al. (2005). Safety and enhanced immunogenicity of a hepatitis B core particle *Plasmodium falciparum* malaria vaccine formulated in adjuvant Montanide ISA 720 in a phase I trial. Infect. Immun. 73, 3387-3397. Parren, P. W., and Burton, D. R. (2001). The antiviral activity of antibodies in vitro and in vivo. *Adv. Immunol.* 77, 195-262.

(25) Pashine, A., Valiante, N. M., and Ulmer, J. B. (2005). Targeting the innate immune response with improved vaccine adjuvants. Nat. Med. 11, S63-S68.

(26) Rey-Cuille, M. A., Svab, J., R., B., Krust, B., Briand, J. P., Muller, S., and Hovanessian, A. G. (2006). The CBD1 epitope is an efficient B-cell epitope vaccine candidate that elicits broadly neutralizing antibodies specific to HIV-1. J. Pharmacy and Pharmacology 58, 759-767.

(27) Rudd, P. M., Elliot, T., Cresswell, P., Wilson, L A., and Dwek, R. A. (2001). Glycosylation and the immune system. Science 291, 2370-2376.

(28) Slingluff, C. L. J., Yamshchikov, G., Neese, P., Galavotti, H., Eastham, S., Engelhard, V. H., Kittlesen, D., Deacon, D., Hibbitts, S., Grosh, W. W., et al. (2001). Phase I trial of a melanomma vaccine with gp 100(280-288) peptide and tetanuus helper peptide in adjuvant; immunologic and clinical outcomes. Clin. Cancer Res. 7, 3012-3024.

(29) Speiser, D. E., Lienard, D., Rufer, N., Rubio-Godoy, V., Rimoldi, D., Lejeune, F., Krieg, A. M., Cerottini, J. C., and Romero, P. (2005). Rapid and strong human CD8+ T cell responses to vaccination with peptide, IFA, and CpG oligodeoxynucleotide 7909. J. Clin. Virol. 115, 739-746.

(30) Wilson, C. C., Palmer, B., Southwoood, S., Sidney, J., Higashimoto, Y., Apella, E., Chestnut, R, Sette, A., and Livingston, B. D. (2001). Identification and antigenicity of broadly cross-reactive and conserved human immunodeficiency virus type-1 derived heler T-lymphocyyte epitopes. J. Virol. 75, 4195-4207.

(31) Wyatt, R, and Sodroski, J. (1998). The HIV-1 envelope glycoproteins: fusogens, antigens, and immunogens, Science 280, 1884-1888.

(32) Yano, A., Onozuka, A., Asahi-Ozaki, Y, Imai, S., Hanada, N., Miwa, Y., and Nisizawa, T. (2005). An ingenious design for peptide vaccines. Vaccine 23, 2322-2326. Zwick, M. B., and Burton, D. R. (2007). HIV-1 neutralization: mechanisms and relevance to vaccine design. Curr. HIV Res. 5, 608-624.

The invention claimed is:

1. A method to induce neutralizing antibodies against HIV-1 comprising administering to a mammal a chimeric peptide comprising a caveolin-1 binding domain (CBD1) of an HIV-1 gp41 peptide fused to a T helper epitope or at least two chimeric peptides comprising a caveolin-1 binding domain (CBD1) of an HIV-1 gp41 peptide fused to a T helper epitope, wherein:
   a. said caveolin-1 binding domain (CBD1) of an HIV-1 gp41 peptide consists of a peptide selected from the group consisting of:
      (a) $X_n$WNNMTW (SEQ ID No: 28), wherein X is any amino acid and n is a number from 1 to 3;
      (b) $X_n$WNNMTWMQWZ$_p$ (SEQ ID No: 29), wherein X and Z are any amino acid or Z is DK, n is 1, 2 or 3 and p is a number from 1 to 3;
      (c) IWNNMTW (SEQ ID NO:50); and
      (d) IWNNMTWMQW (SEQ ID NO:51);
   and,
   b. said T helper epitope is from a peptide selected from the group consisting of a tetanus toxin peptide, an HIV-1 Gag 24 peptide and an HIV-1 Env-gp120 peptide.

2. A method to treat HIV-1 or AIDS or HIV-1 infection comprising administering to a mammal a chimeric peptide comprising a caveolin-1 binding domain (CBD1) of an HIV-1 gp41 peptide fused to a T helper epitope or at least two chimeric peptides comprising a caveolin-1 binding domain (CBD1) of an HIV-1 gp41 peptide fused to a T helper epitope, wherein:
   a. said caveolin-1 binding domain (CBD1) of an HIV-1 gp41 peptide consists of a peptide selected from the group consisting of:
      (a) $X_n$WNNMTW (SEQ ID No: 28), wherein X is any amino acid and n is a number from 1 to 3;
      (b) $X_n$WNNMTWMQWZ$_p$ (SEQ ID No: 29), wherein X and Z are any amino acid or Z is DK, n is 1, 2 or 3 and P is a number from 1 to 3;
      (c) IWNNMTW(SEQ ID NO:50); and
      (d) IWNNMTWMQW(SEQ ID NO:51);
   and,
   b. said T helper epitope is from a peptide selected from the group consisting of a tetanus toxin peptide, an HIV-1 Gag 24 peptide and an HIV-1 Env-gp120 peptide.

3. The method according to claim 1, wherein the caveolin-1 binding domain (CBD1) of said peptide is: IWNNMTW (SEQ ID No: 50) or IWNNMTWMQW (SEQ ID NO: 51).

4. The method according to claim 2, wherein the caveolin-1 binding domain (CBD1) of said peptide is: IWNNMTW (SEQ ID No: 50) or IWNNMTWMQW (SEQ ID NO: 51).

5. The method according to claim 1, wherein the T helper epitope of the chimeric peptide is a tetanus toxin Tet$_{830}$ peptide consisting essentially of the sequence AQYIKAN-SKFIGITEL (SEQ ID No: 2), or an HIV-1 Gag$_{298-312}$ peptide consisting essentially of the sequence KRWI-ILGLNKIVRMY (SEQ ID No: 4).

6. The method according to claim 2, wherein the T helper epitope of the chimeric peptide is a tetanus toxin Tet$_{830}$ peptide consisting essentially of the sequence AQYIKAN-SKFIGITEL (SEQ ID No: 2), or an HIV-1 Gag$_{298-312}$ peptide consisting essentially of the sequence KRWI-ILGLNKIVRMY (SEQ ID No: 4).

7. The method according to claim 1, wherein the caveolin-1 binding domain gp41 and the T helper epitope are linked by a peptide linker, selected from a dilysine linker (KK) and a glycine proline linker.

8. The method according to claim 2, wherein the caveolin-1 binding domain gp41 and the T helper epitope are linked by a peptide linker, selected from a dilysine linker (KK) and a glycine proline linker.

9. The method according to claim 1, wherein said chimeric peptide is selected from the group consisting of:
   a. A-Q-Y-I-K-A-N-S-K-F-I-G-I-T-E-L-K-K-I-W-N-N-M-T-W-M-Q-W-D-K (SEQ ID No: 9),
   b. K-R-W-I-I-L-G-L-N-K-I-V-R-M-Y-K-K-I-W-N-N-M-T-W-M-Q-W-D-K (SEQ ID No: 10),
   c. K-Q-M-N-M-W-Q-V-V-G-K-A-M-Y-A-K-K-I-W-N-N-M-T-W-M-Q-W-D-K (SEQ ID No: 11),
   d. K-R-W-I-I-L-G-L-N-K-I-V-R-M-Y-K-K-I-W-N-N-M-T-W-M-Q-W (SEQ ID No: 12),
   e. K-R-W-I-I-L-G-L-N-K-I-V-R-M-Y-G-P-G-P-G-I-W-N-N-M-T-W-M-Q-W (SEQ ID No: 16),
   f. R-G-D-A-Q-Y-I-K-A-N-S-K-F-I-G-I-T-E-L-K-K-I-W-N-N-M-T-W-M-Q-W-D-K (SEQ ID No: 20),
   g. R-G-D-K-R-W-I-I-L-G-L-N-K-I-V-R-M-Y-K-K-I-W-N-N-M-T-W-M-Q-W-D-K (SEQ ID No: 21),
   h. R-G-D-K-R-W-I-I-L-G-L-N-K-I-V-R-M-Y-K-K-I-W-N-N-M-T-W-M-Q-W (SEQ ID No: 22),
   i. K-R-W-I-I-L-G-L-N-K-I-V-R-M-Y-K-K-I-W-N-N-M-T-W (SEQ ID No: 35),
   j. K-R-W-I-I-L-G-L-N-K-I-V-R-M-Y-G-P-G-P-G-I-W-N-N-M-T-W (SEQ ID No: 38),
   k. A-Q-Y-I-K-A-N-S-K-F-I-G-I-T-E-L-K-K-I-W-N-N-M-T-W-M-Q-W (SEQ ID NO:52),
   l. A-Q-Y-I-K-A-N-S-K-F-I-G-I-T-E-L-K-K-I-W-N-N-M-T-W (SEQ ID NO:53),
   m. A-Q-Y-I-K-A-N-S-K-F-I-G-I-T-E-L-G-P-G-P-G-I-W-N-N-M-T-W-M-Q-W (SEQ ID NO:54),
   n. A-Q-Y-I-K-A-N-S-K-F-I-G-I-T-E-L-G-P-G-P-G-I-W-N-N-M-T-W (SEQ ID NO:55),
   o. K-Q-I-I-N-M-W-Q-V-V-G-K-A-M-Y-A-K-K-I-W-N-N-M-T-W-M-Q-W (SEQ ID NO:56),
   p. K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58), and
   q. K-Q-I-I-N-M-W-Q-V-V-G-K-A-M-Y-A-G-P-G-P-G-I-W-N-N-M-T-W (SEQ ID NO:59),
   and mixtures thereof.

10. The method according to claim 2, wherein said chimeric peptide is selected from the group consisting of:
   a. A-Q-Y-I-K-A-N-S-K-F-I-G-I-T-E-L-K-K-I-W-N-N-M-T-W-M-Q-W-D-K (SEQ ID No: 9),
   b. K-R-W-I-I-L-G-L-N-K-I-V-R-M-Y-K-K-I-W-N-N-M-T-W-M-Q-W-D-K (SEQ ID No: 10),
   c. K-Q-M-N-M-W-Q-V-V-G-K-A-M-Y-A-K-K-I-W-N-N-M-T-W-M-Q-W-D-K (SEQ ID No: 11),
   d. K-R-W-I-I-L-G-L-N-K-I-V-R-M-Y-K-K-I-W-N-N-M-T-W-M-Q-W (SEQ ID No: 12),
   e. K-R-W-I-I-L-G-L-N-K-I-V-R-M-Y-G-P-G-P-G-I-W-N-N-M-T-W-M-Q-W (SEQ ID No: 16),
   f. R-G-D-A-Q-Y-I-K-A-N-S-K-F-I-G-I-T-E-L-K-K-I-W-N-N-M-T-W-M-Q-W-D-K (SEQ ID No: 20),
   g. R-G-D-K-R-W-I-I-L-G-L-N-K-I-V-R-M-Y-K-K-I-W-N-N-M-T-W-M-Q-W-D-K (SEQ ID No: 21),
   h. R-G-D-K-R-W-I-I-L-G-L-N-K-I-V-R-M-Y-K-K-I-W-N-N-M-T-W-M-Q-W (SEQ ID No: 22),
   i. K-R-W-I-I-L-G-L-N-K-I-V-R-M-Y-K-K-I-W-N-N-M-T-W (SEQ ID No: 35),
   j. K-R-W-I-I-L-G-L-N-K-I-V-R-M-Y-G-P-G-P-G-I-W-N-N-M-T-W (SEQ ID No: 38),
   k. A-Q-Y-I-K-A-N-S-K-F-I-G-I-T-E-L-K-K-I-W-N-N-M-T-W-M-Q-W (SEQ ID NO:52),
   l. A-Q-Y-I-K-A-N-S-K-F-I-G-I-T-E-L-K-K-I-W-N-N-M-T-W (SEQ ID NO:53),
   m. A-Q-Y-I-K-A-N-S-K-F-I-G-I-T-E-L-G-P-G-P-G-I-W-N-N-M-T-W-M-Q-W (SEQ ID NO:54),
   n. A-Q-Y-I-K-A-N-S-K-F-I-G-I-T-E-L-G-P-G-P-G-I-W-N-N-M-T-W (SEQ ID NO:55),
   o. K-Q-I-I-N-M-W-Q-V-V-G-K-A-M-Y-A-K-K-I-W-N-N-M-T-W-M-Q-W (SEQ ID NO:56),
   p. K-Q-I-I-N-M-W-Q-V-V-G-K-A-M-Y-A-K-K-I-W-N-N-M-T-W (SEQ ID NO:57), K-Q-I-I-N-M-W-Q-V-V-G-K-A-M-Y-A-G-P-G-P-G-I-W-N-N-M-T-W-M-Q-W (SEQ ID NO:58), and
   q. K-Q-I-I-N-M-W-Q-V-V-G-K-A-M-Y-A-G-P-G-P-G-I-W-N-N-M-T-W (SEQ ID NO:59),
   and mixtures thereof.

11. The method according to claim 1, wherein the at least two chimeric peptides administered consist of SEQ ID NO: 12 (K27W), SEQ ID NO:35 (K24W), SEQ ID NO:16 (K30W (G)) SEQ ID NO:38 (K27W(G)) and SEQ ID No: 31 (C17K).

12. The method according to claim 2, wherein the at least two chimeric peptides administered consist of SEQ ID NO: 12 (K27W), SEQ ID NO:35 (K24W), SEQ ID NO:16 (K30W (G)) SEQ ID NO:38 (K27W(G)) and SEQ ID No: 31 (C17K).

* * * * *

SEQUENCE LISTING

<160> NUMBER OF SEQ ID NOS: 59

<210> SEQ ID NO 1
<211> LENGTH: 16
<212> TYPE: PRT
<213> ORGANISM: Artificial

-continued

```
<220> FEATURE:
<223> OTHER INFORMATION: CBD1

<400> SEQUENCE: 1

Ser Leu Glu Gln Ile Trp Asn Asn Met Thr Trp Met Gln Trp Asp Lys
1               5                   10                  15

<210> SEQ ID NO 2
<211> LENGTH: 16
<212> TYPE: PRT
<213> ORGANISM: Artificial
<220> FEATURE:
<223> OTHER INFORMATION: Tet 830

<400> SEQUENCE: 2

Ala Gln Tyr Ile Lys Ala Asn Ser Lys Phe Ile Gly Ile Thr Glu Leu
1               5                   10                  15

<210> SEQ ID NO 3
<211> LENGTH: 16
<212> TYPE: PRT
<213> ORGANISM: Artificial
<220> FEATURE:
<223> OTHER INFORMATION: gp120 421-436

<400> SEQUENCE: 3

Lys Gln Ile Ile Asn Met Trp Gln Val Val Gly Lys Ala Met Tyr Ala
1               5                   10                  15

<210> SEQ ID NO 4
<211> LENGTH: 15
<212> TYPE: PRT
<213> ORGANISM: Artificial
<220> FEATURE:
<223> OTHER INFORMATION: Gag 298-312

<400> SEQUENCE: 4

Lys Arg Trp Ile Ile Leu Gly Leu Asn Lys Ile Val Arg Met Tyr
1               5                   10                  15

<210> SEQ ID NO 5
<211> LENGTH: 36
<212> TYPE: PRT
<213> ORGANISM: Artificial
<220> FEATURE:
<223> OTHER INFORMATION: A36K - chimeric peptide: T cell epitope of
      tetanus toxin fused to a caveolin-1 binding domain from HIV-1 gp41
      protein

<400> SEQUENCE: 5

Ala Gln Tyr Ile Lys Ala Asn Ser Lys Phe Ile Gly Ile Thr Glu Leu
1               5                   10                  15

Lys Lys Cys Lys Ser Leu Glu Gln Ile Trp Asn Asn Met Thr Trp Met
            20                  25                  30

Gln Trp Asp Lys
        35

<210> SEQ ID NO 6
<211> LENGTH: 35
<212> TYPE: PRT
<213> ORGANISM: Artificial
<220> FEATURE:
<223> OTHER INFORMATION: A35K - chimeric peptide: T cell epitope of
      tetanus toxin fused to a caveolin-1 binding domain from HIV-1 gp41
      protein
```

```
<400> SEQUENCE: 6

Ala Gln Tyr Ile Lys Ala Asn Ser Lys Phe Ile Gly Ile Thr Glu Leu
1               5                   10                  15

Lys Lys Cys Ser Leu Glu Gln Ile Trp Asn Asn Met Thr Trp Met Gln
            20                  25                  30

Trp Asp Lys
        35

<210> SEQ ID NO 7
<211> LENGTH: 36
<212> TYPE: PRT
<213> ORGANISM: Artificial
<220> FEATURE:
<223> OTHER INFORMATION: K36K - chimeric peptide: T helper epitope from
      HIV-1 gp 120 421-436 fused to a caveolin-1 binding domain from
      HIV-1 gp41 protein

<400> SEQUENCE: 7

Lys Gln Ile Ile Asn Met Trp Gln Val Val Gly Lys Ala Met Tyr Ala
1               5                   10                  15

Lys Lys Cys Lys Ser Leu Glu Gln Ile Trp Asn Asn Met Thr Trp Met
            20                  25                  30

Gln Trp Asp Lys
        35

<210> SEQ ID NO 8
<211> LENGTH: 35
<212> TYPE: PRT
<213> ORGANISM: Artificial
<220> FEATURE:
<223> OTHER INFORMATION: K35K - chimeric peptide: HIV-gag tumor DR super
      motif GAG 298-312 fused to a caveolin-1 binding domain from HIV-1
      gp41 protein

<400> SEQUENCE: 8

Lys Arg Trp Ile Ile Leu Gly Leu Asn Lys Ile Val Arg Met Tyr Lys
1               5                   10                  15

Lys Cys Lys Ser Leu Glu Gln Ile Trp Asn Asn Met Thr Trp Met Gln
            20                  25                  30

Trp Asp Lys
        35

<210> SEQ ID NO 9
<211> LENGTH: 30
<212> TYPE: PRT
<213> ORGANISM: Artificial
<220> FEATURE:
<223> OTHER INFORMATION: A30K - chimeric peptide: T cell epitope from
      tetanus toxin fused to a caveolin-1 binding domain from HIV-1 gp41
      protein

<400> SEQUENCE: 9

Ala Gln Tyr Ile Lys Ala Asn Ser Lys Phe Ile Gly Ile Thr Glu Leu
1               5                   10                  15

Lys Lys Ile Trp Asn Asn Met Thr Trp Met Gln Trp Asp Lys
            20                  25                  30

<210> SEQ ID NO 10
<211> LENGTH: 29
<212> TYPE: PRT
<213> ORGANISM: Artificial
```

```
<220> FEATURE:
<223> OTHER INFORMATION: K29K - chimeric peptide: HIV GAG human DR super
      motif GAG 298-312 fused to a caveolin-1 binding domain from HIV-1
      gp41 protein

<400> SEQUENCE: 10

Lys Arg Trp Ile Ile Leu Gly Leu Asn Lys Ile Val Arg Met Tyr Lys
1               5                   10                  15

Lys Ile Trp Asn Asn Met Thr Trp Met Gln Trp Asp Lys
            20                  25

<210> SEQ ID NO 11
<211> LENGTH: 29
<212> TYPE: PRT
<213> ORGANISM: Artificial
<220> FEATURE:
<223> OTHER INFORMATION: K30K - chimeric peptide: T cell epitope from
      HIV-1 gp 120 421-438 fused to a caveolin-1 binding domain from
      HIV-1 gp41 protein

<400> SEQUENCE: 11

Lys Gln Met Asn Met Trp Gln Val Val Gly Lys Ala Met Tyr Ala Lys
1               5                   10                  15

Lys Ile Trp Asn Asn Met Thr Trp Met Gln Trp Asp Lys
            20                  25

<210> SEQ ID NO 12
<211> LENGTH: 27
<212> TYPE: PRT
<213> ORGANISM: Artificial
<220> FEATURE:
<223> OTHER INFORMATION: K27W - chimeric peptide: HIV-1 GAG DR super
      motif GAG 298-312 fused to a caveolin-1 binding domain from HIV-1
      gp41 protein

<400> SEQUENCE: 12

Lys Arg Trp Ile Ile Leu Gly Leu Asn Lys Ile Val Arg Met Tyr Lys
1               5                   10                  15

Lys Ile Trp Asn Asn Met Thr Trp Met Gln Trp
            20                  25

<210> SEQ ID NO 13
<211> LENGTH: 23
<212> TYPE: PRT
<213> ORGANISM: Artificial
<220> FEATURE:
<223> OTHER INFORMATION: Peptide from a caveolin-1 binding domain from
      HIV-1 gp41 protein

<400> SEQUENCE: 13

Lys Arg Trp Met Leu Gly Leu Asn Lys Ile Val Arg Met Tyr Lys Lys
1               5                   10                  15

Ile Trp Asn Asn Met Thr Trp
            20

<210> SEQ ID NO 14
<211> LENGTH: 27
<212> TYPE: PRT
<213> ORGANISM: Artificial
<220> FEATURE:
<223> OTHER INFORMATION: K27M - chimeric peptide: HIV-GAG human DR super
      motif GAG 296-312 fused to a caveolin-1 binding domain from HIV-1
      gp41 protein
```

```
<400> SEQUENCE: 14

Lys Arg Trp Ile Ile Leu Gly Leu Asn Lys Ile Val Arg Met Tyr Lys
1               5                   10                  15

Lys Cys Ser Leu Glu Gln Ile Trp Asn Asn Met
            20                  25

<210> SEQ ID NO 15
<211> LENGTH: 23
<212> TYPE: PRT
<213> ORGANISM: Artificial
<220> FEATURE:
<223> OTHER INFORMATION: Peptide from a caveolin-1 binding domain from
      HN-1 gp41 protein

<400> SEQUENCE: 15

Lys Arg Trp Ile Ile Leu Gly Leu Asn Lys Ile Val Arg Met Tyr Lys
1               5                   10                  15

Lys Cys Ile Trp Asn Asn Met
            20

<210> SEQ ID NO 16
<211> LENGTH: 30
<212> TYPE: PRT
<213> ORGANISM: Artificial
<220> FEATURE:
<223> OTHER INFORMATION: K30W(G) - chimeric peptide: HIV-GAG human DR
      super motif GAG 298-312  fused to a caveolin-1 binding domain from
      HIV-1 gp41 protein

<400> SEQUENCE: 16

Lys Arg Trp Ile Ile Leu Gly Leu Asn Lys Ile Val Arg Met Tyr Gly
1               5                   10                  15

Pro Gly Pro Gly Ile Trp Asn Asn Met Thr Trp Met Gln Trp
            20                  25                  30

<210> SEQ ID NO 17
<211> LENGTH: 28
<212> TYPE: PRT
<213> ORGANISM: Artificial
<220> FEATURE:
<223> OTHER INFORMATION: Peptide from a caveolin-1 binding domain from
      HIV-1 gp41 protein

<400> SEQUENCE: 17

Lys Arg Val Val Ile Ile Leu Gly Leu Asn Lys Ile Val Arg Met Tyr
1               5                   10                  15

Gly Pro Gly Pro Gly Ile Trp Asn Asn Met Thr Trp
            20                  25

<210> SEQ ID NO 18
<211> LENGTH: 29
<212> TYPE: PRT
<213> ORGANISM: Artificial
<220> FEATURE:
<223> OTHER INFORMATION: K29R-2 - chimeric peptide: HIV-GAG human DR
      super motif GAG 298-312 fused to the secondary consensus caveolin-
      1 binding motif

<400> SEQUENCE: 18

Lys Arg Trp Ile Ile Leu Gly Leu Asn Lys Ile Val Arg Met Tyr Lys
1               5                   10                  15

Lys Ile Trp Asp Asn Met Thr Trp Met Glu Trp Glu Arg
            20                  25
```

```
<210> SEQ ID NO 19
<211> LENGTH: 27
<212> TYPE: PRT
<213> ORGANISM: Artificial
<220> FEATURE:
<223> OTHER INFORMATION: K27W-2 - chimeric peptide: HIV-GAG human DR
      super motif GAG 298-312 fused to the secondary consensus caveolin-
      1 binding motif

<400> SEQUENCE: 19

Lys Arg Trp Ile Ile Leu Gly Leu Asn Lys Ile Val Arg Met Tyr Lys
1               5                   10                  15

Lys Ile Trp Asp Asn Met Thr Trp Met Glu Trp
            20                  25

<210> SEQ ID NO 20
<211> LENGTH: 33
<212> TYPE: PRT
<213> ORGANISM: Artificial
<220> FEATURE:
<223> OTHER INFORMATION: R33K - chimeric peptide: integrin binding motif
      RGD fused to T cell epitope of tetanus toxin fused to a caveolin-1
      binding domain from HIV-1 gp41 protein

<400> SEQUENCE: 20

Arg Gly Asp Ala Gln Tyr Ile Lys Ala Asn Ser Lys Phe Ile Gly Ile
1               5                   10                  15

Thr Glu Leu Lys Lys Ile Trp Asn Asn Met Thr Trp Met Gln Trp Asp
            20                  25                  30

Lys

<210> SEQ ID NO 21
<211> LENGTH: 32
<212> TYPE: PRT
<213> ORGANISM: Artificial
<220> FEATURE:
<223> OTHER INFORMATION: R32K - chimeric peptide: integrin binding motif
      RGD fused to HIV GAG human DR super motif GAG 298-312 fused to a
      caveolin-1 binding domain from HIV-1 gp41 protein

<400> SEQUENCE: 21

Arg Gly Asp Lys Arg Trp Ile Ile Leu Gly Leu Asn Lys Ile Val Arg
1               5                   10                  15

Met Tyr Lys Lys Ile Trp Asn Asn Met Thr Trp Met Gln Trp Asp Lys
            20                  25                  30

<210> SEQ ID NO 22
<211> LENGTH: 30
<212> TYPE: PRT
<213> ORGANISM: Artificial
<220> FEATURE:
<223> OTHER INFORMATION: R30W - chimeric peptide: integrin binding motif
      RGD fused to HIV GAG human DR super motif GAG 298-312  fused to
      a caveolin-1 binding domain from HIV-1 gp41 protein

<400> SEQUENCE: 22

Arg Gly Asp Lys Arg Trp Ile Ile Leu Gly Leu Asn Lys Ile Val Arg
1               5                   10                  15

Met Tyr Lys Lys Ile Trp Asn Asn Met Thr Trp Met Gln Trp
            20                  25                  30

<210> SEQ ID NO 23
<211> LENGTH: 12
<212> TYPE: PRT
<213> ORGANISM: Artificial
```

```
<220> FEATURE:
<223> OTHER INFORMATION: Determinant - caveolin binding domain of HIV-1

<400> SEQUENCE: 23

Ile Trp Asn Asn Met Thr Trp Met Gln Trp Asp Lys
1               5                   10

<210> SEQ ID NO 24
<211> LENGTH: 15
<212> TYPE: PRT
<213> ORGANISM: Artificial
<220> FEATURE:
<223> OTHER INFORMATION: Peptide p62 of HIV-1

<400> SEQUENCE: 24

Ala Ser Trp Ser Asn Lys Ser Leu Asp Asp Ile Trp Asn Asn Met
1               5                   10                  15

<210> SEQ ID NO 25
<211> LENGTH: 28
<212> TYPE: PRT
<213> ORGANISM: Artificial
<220> FEATURE:
<223> OTHER INFORMATION: CBD1 variant
<220> FEATURE:
<221> NAME/KEY: MISC_FEATURE
<222> LOCATION: (1)..(6)
<223> OTHER INFORMATION: Each Xaa is any amino acid or no amino acid
<220> FEATURE:
<221> NAME/KEY: MISC_FEATURE
<222> LOCATION: (23)..(28)
<223> OTHER INFORMATION: Each Xaa is any amino acid or no amino acid

<400> SEQUENCE: 25

Xaa Xaa Xaa Xaa Xaa Xaa Ser Leu Glu Gln Ile Trp Asn Asn Met Thr
1               5                   10                  15

Trp Met Gln Trp Asp Lys Xaa Xaa Xaa Xaa Xaa Xaa
            20                  25

<210> SEQ ID NO 26
<211> LENGTH: 9
<212> TYPE: PRT
<213> ORGANISM: Artificial
<220> FEATURE:
<223> OTHER INFORMATION: CBD1 variant

<400> SEQUENCE: 26

Trp Asn Asn Met Thr Trp Met Gln Trp
1               5

<210> SEQ ID NO 27
<211> LENGTH: 10
<212> TYPE: PRT
<213> ORGANISM: Artificial
<220> FEATURE:
<223> OTHER INFORMATION: CBD1 variant
<220> FEATURE:
<221> NAME/KEY: MISC_FEATURE
<222> LOCATION: (1)..(5)
<223> OTHER INFORMATION: Each Xaa is any amino acid or no amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 27

Xaa Xaa Xaa Xaa Xaa Xaa Trp Asn Asn Met
1               5                   10
```

```
<210> SEQ ID NO 28
<211> LENGTH: 9
<212> TYPE: PRT
<213> ORGANISM: Artificial
<220> FEATURE:
<223> OTHER INFORMATION: CBD1 variant
<220> FEATURE:
<221> NAME/KEY: MISC_FEATURE
<222> LOCATION: (1)..(2)
<223> OTHER INFORMATION: Each Xaa is any amino acid or no amino acid
<220> FEATURE:
<221> NAME/KEY: MISC_FEATURE
<222> LOCATION: (3)..(3)
<223> OTHER INFORMATION: Xaa is any amino acid

<400> SEQUENCE: 28

Xaa Xaa Xaa Trp Asn Asn Met Thr Trp
1               5

<210> SEQ ID NO 29
<211> LENGTH: 18
<212> TYPE: PRT
<213> ORGANISM: Artificial
<220> FEATURE:
<223> OTHER INFORMATION: CBD1 variant
<220> FEATURE:
<221> NAME/KEY: MISC_FEATURE
<222> LOCATION: (1)..(5)
<223> OTHER INFORMATION: Each Xaa is any amino acid or no amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (17)..(18)
<223> OTHER INFORMATION: Each Xaa is any amino acid or no amino acid

<400> SEQUENCE: 29

Xaa Xaa Xaa Xaa Xaa Xaa Trp Asn Asn Met Thr Trp Met Gln Trp Xaa
1               5                   10                  15

Xaa Xaa

<210> SEQ ID NO 30
<211> LENGTH: 17
<212> TYPE: PRT
<213> ORGANISM: Artificial
<220> FEATURE:
<223> OTHER INFORMATION: CBD1 variant
<220> FEATURE:
<221> NAME/KEY: MISC_FEATURE
<222> LOCATION: (1)..(5)
<223> OTHER INFORMATION: Each Xaa is any amino acid or no amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 30

Xaa Xaa Xaa Xaa Xaa Xaa Trp Asn Asn Met Thr Trp Met Gln Trp Asp
1               5                   10                  15

Lys

<210> SEQ ID NO 31
<211> LENGTH: 17
<212> TYPE: PRT
<213> ORGANISM: Artificial
```

```
<220> FEATURE:
<223> OTHER INFORMATION: C17K - cysteinyl-CBD1 peptide

<400> SEQUENCE: 31

Cys Ser Leu Glu Gln Ile Trp Asn Asn Met Thr Trp Met Gln Trp Asp
1               5                   10                  15
Lys

<210> SEQ ID NO 32
<211> LENGTH: 10
<212> TYPE: PRT
<213> ORGANISM: Artificial
<220> FEATURE:
<223> OTHER INFORMATION: C10M - CBD1 peptide

<400> SEQUENCE: 32

Cys Ser Leu Glu Gln Ile Trp Asn Asn Met
1               5                   10

<210> SEQ ID NO 33
<211> LENGTH: 13
<212> TYPE: PRT
<213> ORGANISM: Artificial
<220> FEATURE:
<223> OTHER INFORMATION: C13K - CBD1 peptide

<400> SEQUENCE: 33

Cys Ile Trp Asn Asn Met Thr Trp Met Gln Trp Asp Lys
1               5                   10

<210> SEQ ID NO 34
<211> LENGTH: 29
<212> TYPE: PRT
<213> ORGANISM: Artificial
<220> FEATURE:
<223> OTHER INFORMATION: K29K - chimeric peptide: HIV GAG human DR super
      motif GAG 298-312 fused to a caveolin-1 binding domain from HIV-1
      gp41 protein

<400> SEQUENCE: 34

Lys Arg Trp Ile Ile Leu Gly Leu Asn Lys Ile Val Arg Met Tyr Lys
1               5                   10                  15

Lys Ile Trp Asn Asn Met Thr Trp Met Gln Trp Asp Lys
            20                  25

<210> SEQ ID NO 35
<211> LENGTH: 24
<212> TYPE: PRT
<213> ORGANISM: Artificial
<220> FEATURE:
<223> OTHER INFORMATION: K24W - chimeric peptide: HIV GAG human DR super
      motif GAG 298-312 fused to a caveolin-1 binding domain from HIV-1
      gp41 protein

<400> SEQUENCE: 35

Lys Arg Trp Ile Ile Leu Gly Leu Asn Lys Ile Val Arg Met Tyr Lys
1               5                   10                  15

Lys Ile Trp Asn Asn Met Thr Trp
            20

<210> SEQ ID NO 36
<211> LENGTH: 22
<212> TYPE: PRT
<213> ORGANISM: Artificial
```

```
<220> FEATURE:
<223> OTHER INFORMATION: K23M - chimeric peptide: HIV GAG human DR super
      motif GAG 298-312 fused to a caveolin-1 binding domain from HIV-1
      gp41 protein

<400> SEQUENCE: 36

Lys Arg Trp Ile Ile Leu Gly Leu Asn Lys Ile Val Arg Met Tyr Lys
1               5                   10                  15

Lys Ile Trp Asn Asn Met
            20

<210> SEQ ID NO 37
<211> LENGTH: 30
<212> TYPE: PRT
<213> ORGANISM: Artificial
<220> FEATURE:
<223> OTHER INFORMATION: K30W(G) - chimeric peptide: HIV GAG human DR
      super motif GAG 298-312 fused to a caveolin-1 binding domain from
      HIV-1 gp41 protein

<400> SEQUENCE: 37

Lys Arg Trp Ile Ile Leu Gly Leu Asn Lys Ile Val Arg Met Tyr Gly
1               5                   10                  15

Pro Gly Pro Gly Ile Trp Asn Asn Met Thr Trp Met Gln Trp
            20                  25                  30

<210> SEQ ID NO 38
<211> LENGTH: 27
<212> TYPE: PRT
<213> ORGANISM: Artificial
<220> FEATURE:
<223> OTHER INFORMATION: K27W(G) - chimeric peptide: HIV GAG human DR
      super motif GAG 298-312 fused to a caveolin-1 binding domain
      from HIV-1 gp41 protein

<400> SEQUENCE: 38

Lys Arg Trp Ile Ile Leu Gly Leu Asn Lys Ile Val Arg Met Tyr Gly
1               5                   10                  15

Pro Gly Pro Gly Ile Trp Asn Asn Met Thr Trp
            20                  25

<210> SEQ ID NO 39
<211> LENGTH: 17
<212> TYPE: PRT
<213> ORGANISM: Artificial
<220> FEATURE:
<223> OTHER INFORMATION: CBD1/A peptide

<400> SEQUENCE: 39

Cys Ser Leu Glu Gln Ile Ala Asn Asn Met Thr Ala Met Gln Ala Asp
1               5                   10                  15

Lys

<210> SEQ ID NO 40
<211> LENGTH: 17
<212> TYPE: PRT
<213> ORGANISM: Artificial
<220> FEATURE:
<223> OTHER INFORMATION: CBD2 peptide; caveolin binding domain 2

<400> SEQUENCE: 40

Cys Ser Leu Thr Pro Asp Trp Asn Asn Met Thr Trp Gln Glu Trp Glu
1               5                   10                  15

Arg
```

```
<210> SEQ ID NO 41
<211> LENGTH: 9
<212> TYPE: PRT
<213> ORGANISM: Artificial
<220> FEATURE:
<223> OTHER INFORMATION: Peptide - conserved caveolin-binding motif
<220> FEATURE:
<221> NAME/KEY: MISC_FEATURE
<222> LOCATION: (2)..(5)
<223> OTHER INFORMATION: Xaa is any amino acid
<220> FEATURE:
<221> NAME/KEY: MISC_FEATURE
<222> LOCATION: (7)..(8)
<223> OTHER INFORMATION: Xaa is any amino acid

<400> SEQUENCE: 41

Trp Xaa Xaa Xaa Xaa Trp Xaa Xaa Trp
1               5

<210> SEQ ID NO 42
<211> LENGTH: 18
<212> TYPE: PRT
<213> ORGANISM: Artificial
<220> FEATURE:
<223> OTHER INFORMATION: C18K - Cysteinyl-CBD1 peptide

<400> SEQUENCE: 42

Cys Lys Ser Leu Glu Gln Ile Trp Asn Asn Met Thr Trp Met Gln Trp
1               5                   10                  15

Asp Lys

<210> SEQ ID NO 43
<211> LENGTH: 16
<212> TYPE: PRT
<213> ORGANISM: Artificial
<220> FEATURE:
<223> OTHER INFORMATION: CBD2 peptide; caveolin binding domain 2

<400> SEQUENCE: 43

Ser Leu Thr Pro Asp Trp Asn Asn Met Thr Trp Gln Glu Trp Glu Arg
1               5                   10                  15

<210> SEQ ID NO 44
<211> LENGTH: 15
<212> TYPE: PRT
<213> ORGANISM: Artificial
<220> FEATURE:
<223> OTHER INFORMATION: p6362 peptide: segment of CBD1

<400> SEQUENCE: 44

Asn Lys Ser Leu Asp Asp Ile Trp Asn Asn Met Thr Trp Met Gln
1               5                   10                  15

<210> SEQ ID NO 45
<211> LENGTH: 15
<212> TYPE: PRT
<213> ORGANISM: Artificial
<220> FEATURE:
<223> OTHER INFORMATION: p6364 peptide: segment of CBD1

<400> SEQUENCE: 45

Asp Asp Ile Trp Asn Asn Met Thr Trp Met Gln Trp Glu Arg Glu
1               5                   10                  15

<210> SEQ ID NO 46
<211> LENGTH: 15
<212> TYPE: PRT
<213> ORGANISM: Artificial
```

```
<220> FEATURE:
<223> OTHER INFORMATION: p6365 peptide: segment of CBD1

<400> SEQUENCE: 46

Asn Asn Met Thr Trp Met Gln Trp Glu Arg Glu Ile Asp Asn Tyr
1               5                   10                  15

<210> SEQ ID NO 47
<211> LENGTH: 15
<212> TYPE: PRT
<213> ORGANISM: Artificial
<220> FEATURE:
<223> OTHER INFORMATION: p9127 peptide: segment of CBD1

<400> SEQUENCE: 47

Glu Ile Trp Asp Asn Met Thr Trp Met Glu Trp Glu Arg Glu Ile
1               5                   10                  15

<210> SEQ ID NO 48
<211> LENGTH: 5
<212> TYPE: PRT
<213> ORGANISM: Artificial
<220> FEATURE:
<223> OTHER INFORMATION: Determinant - peptide CBD1 epitope

<400> SEQUENCE: 48

Ile Trp Asn Asn Met
1               5

<210> SEQ ID NO 49
<211> LENGTH: 9
<212> TYPE: PRT
<213> ORGANISM: Artificial
<220> FEATURE:
<223> OTHER INFORMATION: Determinant - peptide CBD1 epitope

<400> SEQUENCE: 49

Ser Leu Glu Gln Ile Trp Asn Asn Met
1               5

<210> SEQ ID NO 50
<211> LENGTH: 7
<212> TYPE: PRT
<213> ORGANISM: Artificial
<220> FEATURE:
<223> OTHER INFORMATION: Determinant - peptide CBD1 epitope

<400> SEQUENCE: 50

Ile Trp Asn Asn Met Thr Trp
1               5

<210> SEQ ID NO 51
<211> LENGTH: 10
<212> TYPE: PRT
<213> ORGANISM: Artificial
<220> FEATURE:
<223> OTHER INFORMATION: Determinant - peptide CBD1 epitope

<400> SEQUENCE: 51

Ile Trp Asn Asn Met Thr Trp Met Gln Trp
1               5                   10

<210> SEQ ID NO 52
<211> LENGTH: 28
<212> TYPE: PRT
<213> ORGANISM: Artificial
```

```
<220> FEATURE:
<223> OTHER INFORMATION: T cell epitope of tetanus toxin fused to CBM-
      based peptide

<400> SEQUENCE: 52

Ala Gln Tyr Ile Lys Ala Asn Ser Lys Phe Ile Gly Ile Thr Glu Leu
1               5                   10                  15

Lys Lys Ile Trp Asn Asn Met Thr Trp Met Gln Trp
            20                  25

<210> SEQ ID NO 53
<211> LENGTH: 25
<212> TYPE: PRT
<213> ORGANISM: Artificial
<220> FEATURE:
<223> OTHER INFORMATION: T cell epitope of tetanus toxin fused to CBM-
      based peptide

<400> SEQUENCE: 53

Ala Gln Tyr Ile Lys Ala Asn Ser Lys Phe Ile Gly Ile Thr Glu Leu
1               5                   10                  15

Lys Lys Ile Trp Asn Asn Met Thr Trp
            20                  25

<210> SEQ ID NO 54
<211> LENGTH: 31
<212> TYPE: PRT
<213> ORGANISM: Artificial
<220> FEATURE:
<223> OTHER INFORMATION: T cell epitope of tetanus toxin fused to CBM-
      based peptide

<400> SEQUENCE: 54

Ala Gln Tyr Ile Lys Ala Asn Ser Lys Phe Ile Gly Ile Thr Glu Leu
1               5                   10                  15

Gly Pro Gly Pro Gly Ile Trp Asn Asn Met Thr Trp Met Gln Trp
            20                  25                  30

<210> SEQ ID NO 55
<211> LENGTH: 28
<212> TYPE: PRT
<213> ORGANISM: Artificial
<220> FEATURE:
<223> OTHER INFORMATION: T cell epitope of tetanus toxin fused to CBM-
      based peptide

<400> SEQUENCE: 55

Ala Gln Tyr Ile Lys Ala Asn Ser Lys Phe Ile Gly Ile Thr Glu Leu
1               5                   10                  15

Gly Pro Gly Pro Gly Ile Trp Asn Asn Met Thr Trp
            20                  25

<210> SEQ ID NO 56
<211> LENGTH: 28
<212> TYPE: PRT
<213> ORGANISM: Artificial
<220> FEATURE:
<223> OTHER INFORMATION: T helper epitope from HIV gp120 421-436 fused
      to CBM-based peptide

<400> SEQUENCE: 56

Lys Gln Ile Ile Asn Met Trp Gln Val Val Gly Lys Ala Met Tyr Ala
1               5                   10                  15

Lys Lys Ile Trp Asn Asn Met Thr Trp Met Gln Trp
            20                  25
```

```
<210> SEQ ID NO 57
<211> LENGTH: 25
<212> TYPE: PRT
<213> ORGANISM: Artificial
<220> FEATURE:
<223> OTHER INFORMATION: T helper epitope from HIV gp120 421-436 fused
      to CBM-based peptide

<400> SEQUENCE: 57

Lys Gln Ile Ile Asn Met Trp Gln Val Val Gly Lys Ala Met Tyr Ala
1               5                   10                  15

Lys Lys Ile Trp Asn Asn Met Thr Trp
            20                  25

<210> SEQ ID NO 58
<211> LENGTH: 31
<212> TYPE: PRT
<213> ORGANISM: Artificial
<220> FEATURE:
<223> OTHER INFORMATION: T helper epitope from HIV gp120 421-436 fused
      to CBM-based peptide

<400> SEQUENCE: 58

Lys Gln Ile Ile Asn Met Trp Gln Val Val Gly Lys Ala Met Tyr Ala
1               5                   10                  15

Gly Pro Gly Pro Gly Ile Trp Asn Asn Met Thr Trp Met Gln Trp
            20                  25                  30

<210> SEQ ID NO 59
<211> LENGTH: 28
<212> TYPE: PRT
<213> ORGANISM: Artificial
<220> FEATURE:
<223> OTHER INFORMATION: T helper epitope from HIV gp120 421-436 fused
      to CBM-based peptide

<400> SEQUENCE: 59

Lys Gln Ile Ile Asn Met Trp Gln Val Val Gly Lys Ala Met Tyr Ala
1               5                   10                  15

Gly Pro Gly Pro Gly Ile Trp Asn Asn Met Thr Trp
            20                  25
```